(12) United States Patent
Dunn et al.

(10) Patent No.: US 11,186,839 B2
(45) Date of Patent: Nov. 30, 2021

(54) METHODS FOR PREVENTING TITRATION OF BIMOLECULAR TEMPLATED ASSEMBLY REACTIONS BY STRUCTURALLY-DETERMINED DIFFERENTIAL HYBRIDIZATIONS

(71) Applicant: TriBiotica LLC, Madison, WI (US)

(72) Inventors: Ian Dunn, Madison, WI (US); Matthew Lawler, Madison, WI (US)

(73) Assignee: TriBiotica LLC, Madison, WI (US)

( * ) Notice: Subject to any disclaimer, the term of this patent is extended or adjusted under 35 U.S.C. 154(b) by 109 days.

(21) Appl. No.: 16/462,324

(22) PCT Filed: Nov. 16, 2017

(86) PCT No.: PCT/US2017/062048
§ 371 (c)(1),
(2) Date: May 20, 2019

(87) PCT Pub. No.: WO2018/094070
PCT Pub. Date: May 24, 2018

(65) Prior Publication Data
US 2019/0316131 A1 Oct. 17, 2019

Related U.S. Application Data

(60) Provisional application No. 62/424,607, filed on Nov. 21, 2016.

(51) Int. Cl.
*C12N 15/113* (2010.01)
*C07H 21/00* (2006.01)

(52) U.S. Cl.
CPC ........ *C12N 15/113* (2013.01); *C12N 2310/14* (2013.01)

(58) Field of Classification Search
CPC ......... C12N 15/113; C12Q 1/68; C07H 21/00
See application file for complete search history.

(56) References Cited

U.S. PATENT DOCUMENTS

| | | | |
|---|---|---|---|
| 5,514,546 A | 5/1996 | Kool | |
| 5,858,731 A | 1/1999 | Sorge | |
| 5,925,517 A * | 7/1999 | Tyagi | C12Q 1/6816 435/6.1 |
| 2002/0172965 A1 | 11/2002 | Kamb et al. | |
| 2005/0026178 A1 | 2/2005 | Nilsen-Hamilton | |
| 2005/0048192 A1 | 3/2005 | Raines et al. | |
| 2005/0287548 A1 | 12/2005 | Bao | |
| 2006/0099592 A1 | 5/2006 | Freskgard | |
| 2006/0147963 A1 | 7/2006 | Barone et al. | |
| 2006/0223777 A1 | 10/2006 | Vermeulen et al. | |
| 2006/0292438 A1 * | 12/2006 | Greenfield | B82Y 10/00 429/63 |
| 2007/0099222 A1 | 5/2007 | Gee et al. | |
| 2007/0190597 A1 | 8/2007 | Agnew et al. | |
| 2008/0044834 A1 | 2/2008 | Heyduk et al. | |
| 2008/0050731 A1 | 2/2008 | Agnew et al. | |
| 2008/0071074 A1 | 3/2008 | Skrzypczynski et al. | |
| 2009/0124571 A1 | 5/2009 | Morvan et al. | |
| 2010/0048866 A1 | 2/2010 | Raines et al. | |
| 2010/0055728 A1 | 3/2010 | Yang | |
| 2012/0009566 A1 | 1/2012 | Soukka | |
| 2015/0203841 A1 | 7/2015 | Rasmussen | |
| 2016/0025726 A1 | 1/2016 | Altin et al. | |
| 2016/0106854 A1 | 4/2016 | Dunn et al. | |

FOREIGN PATENT DOCUMENTS

| | | |
|---|---|---|
| CN | 101538613 | 9/2009 |
| EP | 2796150 | 10/2014 |
| JP | H10512446 | 12/1998 |
| JP | 2009528988 | 8/2009 |
| JP | 2014055167 | 3/2014 |
| WO | 1997031899 | 9/1997 |
| WO | 0061775 | 10/2000 |
| WO | 2004011486 | 2/2004 |
| WO | 2006053571 | 5/2006 |
| WO | 2006058496 | 6/2006 |
| WO | 2009129281 | 10/2009 |
| WO | 2011089393 | 7/2011 |
| WO | 2012057689 | 5/2012 |
| WO | 2013012434 | 1/2013 |
| WO | 2014197547 | 11/2014 |
| WO | 2015122835 | 8/2015 |
| WO | 2015175747 | 11/2015 |
| WO | 2016089958 | 6/2016 |
| WO | 2016134232 | 8/2016 |
| WO | 2017049094 | 3/2017 |
| WO | 2017205277 | 11/2017 |
| WO | 2018093978 | 5/2018 |

OTHER PUBLICATIONS

Kaur et al., Chem Rev. 107 :4672 (Year: 2007).*
Pinheiro et al., Current Opinion in Chemical Biology 16 :245 (Year: 2012).*
El-Sagheer et al., "Click chemistry with DNA", Chemical Society Reviews, 2010, 39(4), pp. 1388.
Gu et al., "Protein tag-mediated conjugation of oligonucleotides to recombinant affinity binders for proximity ligation", New Biotechnology, 2012, 30(2), pp. 144-152.
He et al., "Visual detection of single-base mismatches in DNA using hairpin oligonucleotide with double-target DNA binding sequences and gold nanoparticles", Biosensors and Bioelectronics, 2012, 34(1), pp. 37-43.
Hu et al., "Simple and fast electrochemical detection of sequence-specific DNA via click chemistry-mediated labeling of hairpin DNA probes with ethylnylferrocene", Analyst, 2015, 140(12), pp. 4154-4161.

(Continued)

*Primary Examiner* — Ethan C Whisenant
(74) *Attorney, Agent, or Firm* — Stradley Ronon Stevens & Young, LLP

(57) ABSTRACT

The present disclosure provides nucleic acid molecules, and kits comprising the same, for producing templated assembly products for a cell.

11 Claims, 20 Drawing Sheets
Specification includes a Sequence Listing.

(56) References Cited

OTHER PUBLICATIONS

Lloyd et al., "Modulation of oligonucleotide duplex and triplex stability via hydrophobic interactions", Nucleic Acids Research, 1993, 21(5), pp. 5909-5915.
Mao et al., "Molecular beacon-functionalized gold nanoparticles as probes in dry-reagent strip biosensor for DNA analysis", Chemical Communications, 2009, 21, pp. 3065.
Nakagawa et al., "Targeted Intracellular Delivery of Antisense Oligonucleotides via Conjugation with Small-Molecule Ligands", JACS, 2010, 132(26), pp. 8848-8849.
Pyati et al., "Optimising expression of the recombinant fusion protein biopesticide [omega]-hexatoxin-Hv1a/GNA in Pichia pastoris: sequence modifications and a simple method for the generation of multi-copy strains", Journal of Industrial Microbiology & Biotechnology, 2014, 41(8), pp. 1237-1247.
Qian et al., "A novel signal-on electrochemical DNA sensor based on target catalyzed hairpin assembly strategy", Biosensors and Bioelectronics, 2014, 64, pp. 177-181.
Sonntag et al., "An intein-cassette integration approach used for the generation of a split TEV protease activated by conditional protein splicing", Molecular Biosystems, 2011, 7(6), pp. 2031.
Sun et al., "Electrochemical Detection of Peanut Allergan Ara h 1 Using a Sensitive DNA Biosensor Based on Stem-Loop Probe", Journal of Agricultural and Food Chemistry, 2012, 60(44), p. 10979-10984.
Xu et al., "Effect of location of the His-tag on the production of soluble and functional Buthus martensii Karsch insect toxin", Protein Expression and Purification, 2008, 59(1), pp. 103-109.
Yaqin et al., "Tenison promoted circular probe for highly selective microRNA detection and imaging", Biosensors and Bioelectronics, 2016, 85, pp. 151-156.
Zhou, "Synthesis of new tetrazines functionalized with photoactive and electroactive groups", 2012, PhD Thesis, Ecole normale superieure de Cachan-ENS Cachan.
Zimnik et al., "Mutually exclusive STAT1 modifications identified by Ubc9/substrate dimerization-dependent SUMOylation", Nucleic Acids Research, 2008, 37(4), pp. e30.
Final Official Action dated Jul. 28, 2020 in related U.S. Appl. No. 15/601,449.
Official Action dated Dec. 11, 2019 in related U.S. Appl. No. 15/601,449.
Official Action dated Dec. 6, 2019 in related U.S. Appl. No. 15/529,807.
Notice of Allowance dated Nov. 21, 2019 in related U.S. Appl. No. 14/895,398.
Niwayama et al., "A Pyrene Maleimide with a Flexible Linker for Sampling of Longer Inter-Thiol Distances by Excimer Formation", PLoS ONE, 2011, 6(10), e26691.
Bendifallah et al., "Evaluation of Cell-Penetrating Peptides (CPPs) as Vehicles for Intracellular Delivery of Antisense Peptide Nucleic Acid (PNA)", Bioconjugate Chem., 2006, 17:750-758.
Blanco-Canosa and Dawson, "An efficient Fmoc-SPPS approach for the generation of thioester peptide precursors for use in native chemical ligation", Angew Chem Int Ed Engl, 2008, 47(36):6851-6855.
Clackson et al., "Redesigning an FKBP-ligand interface to generate chemical dimerizers with novel specificity", PNAS USA, 1998, 95(18):10437-10442.
D.Y. Wu and B. Wallace "The Ligation Amplification Reaction (LAR)—Amplification of Specific DNA Sequences Using Sequential Rounds of Template-Dependent Ligation", Genomics, 1989, 4:560-569.
Imoto et al., "DNA-template click chemistry for creation of novel DNA binding molecules", Bioorganic & Medicinal Chem Lett, 2008, 18(20):5660-5663.
International Search Report and Written Opinion for PCT/US2015/063368.
Kalia et al., "Reactivity of Intein Thioesters: Appending a Functional Group to a Protein", ChemBioChem, 2006, 7:1375-1383.
Kazane et al., "Self-Assembled Antibody Multimers Through Peptide Nucleic Acid Conjugation", JACS, 2012, 135:340-346.
Knecht et al., "Oligohis-tags: mechanisms of binding to Ni2+ surfaces", J Mol Recognit, 2009, 22:270-279.
LeGall et al., "Protable flanking sequences modulate CTL epitope processing", J Clin Invest, 2007, 117(11):3563-3575.
Monroy-Contreras et al., "Molecular Beacons: Powerful Tools For Imaging RNA in Living Cells", J Nuc Acids, 2011, 5-6.
Official Action dated Aug. 6, 2018 in U.S. Appl. No. 14/895,398.
Official Action dated Jun. 11, 2019 in related U.S. Appl. No. 14/895,398.
Official Action dated Mar. 6, 2019 in related U.S. Appl. No. 15/529,807.
Official Action dated Nov. 15, 2017 in related U.S. Appl. No. 14/895,398.
Overkamp et al., "Benchmarking various green fluorescent protein variants in Bacillus subtilis, *Streptococcus pneumoniae*, and Lactococcus lactis for live cell imaging", Appl Environ Microbiol, 2013, 79(20):6481-6490.
Pai et al., "Using RNA aptamers and the proximity ligation assay for the detection of cell surface antigens", Methods Mol Biol, 2009, 504:385-398.
Paulmurugan et al., "Monitoring protein-protein interactions using split synthetic renilla luciferase protein-fragment-assisted complementation", Anal Chem, 2003, 75(7):1584-1589.
Ponomarenko et al., "Recent advances in self-assembled fluorescent DNA structures and probes", Curr Top Med Chem, 2015, 15(13):1162-1178.
Restriction Requirement dated Mar. 28, 2017, issued in related U.S. Appl. No. 14/895,398.
Roosild et al., "Structure of anti-FLAG M2 Fab domain and its use in the stabilization of engineered membrane proteins", Acta Crystallogr Sect F Struct Biol Cryst Commun, 2006, 62(9):835-839.
Sletten et al., "From mechanism to mouse: a tale of two bioorthogonal reactions", Acc Chem Res, 2011, 44(9):666-676.
Tam and Raines, "Coulombic effects on the traceless Staudinger ligation in water", Bioorg Med Chem, 2009, 17(3):1055-1063.
Tam et al., "Water-soluble phosphinothiols for traceless Staudinger ligation and integration with expressed protein ligation", J Am Chem Soc, 2007, 129(37):11421-11430.
Walder et al., "Complementary carrier peptide synthesis: general strategy and implications for prebiotic origin of peptide synthesis", PNAS, 1979, 76(1):51-55.
Weisbrod et al., "Synthesis of Water-Soluble Phosphinophenol for Traceless Staudinger Ligation", Synlett, 2010, 5:787-789.
Zhao et al., "Solid-phase synthesis and evaluation of TAR RNA targeted beta-carboline-nucleoside conjugates", Organic and Biomolecular Chemistry, 2008, 6(20):3741-3750.
Notice of Allowance dated Mar. 2, 2020 in related U.S. Appl. No. 15/529,807.
Riemer et al., "Matching of trastuzumab (Herceptin[158] (R)) epitope mimics onto the surface of Her-2/neu—a new method of epitope definition", Pergamon, 2005, 42(9), pp. 1121-1124.
Wu et al., "Aptmpers: Active Targeting Ligands for Cancer Diagnosis and Therapy", Theranostics, 2015, 5(4), pp. 322-344.

* cited by examiner

Model template
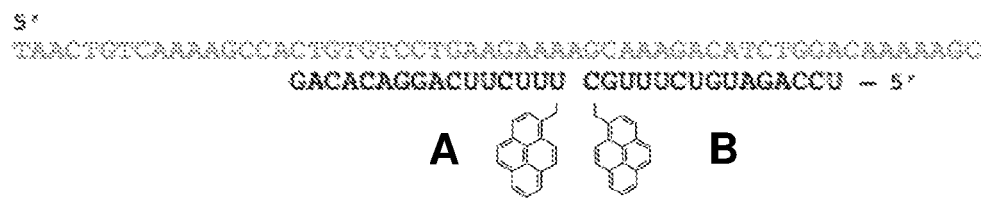
A, B = pyrene-labeled haplomers (pyrenes bound at 5'- and 3'- positions, respectively) complementary to model template
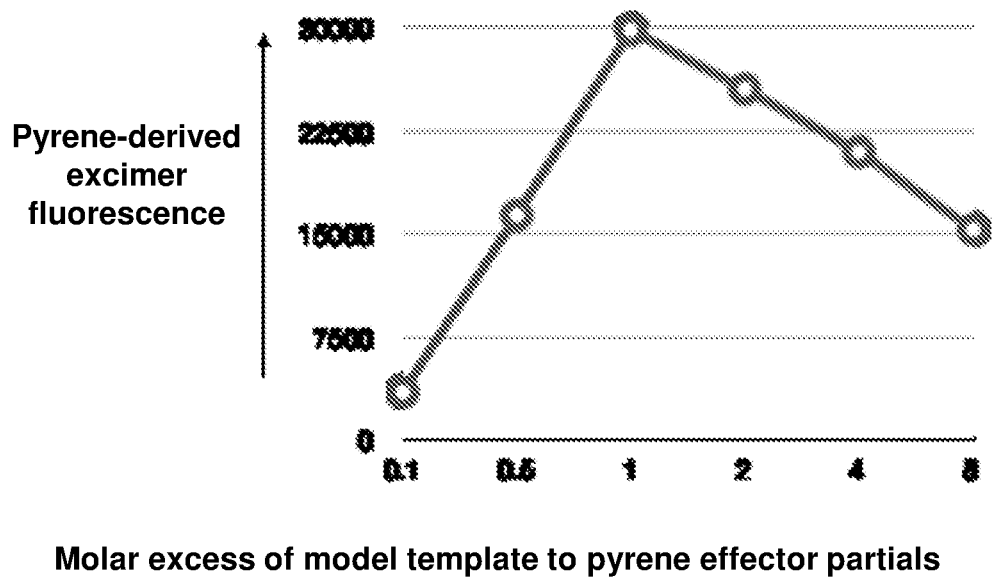
Molar excess of model template to pyrene effector partials
Figure 2

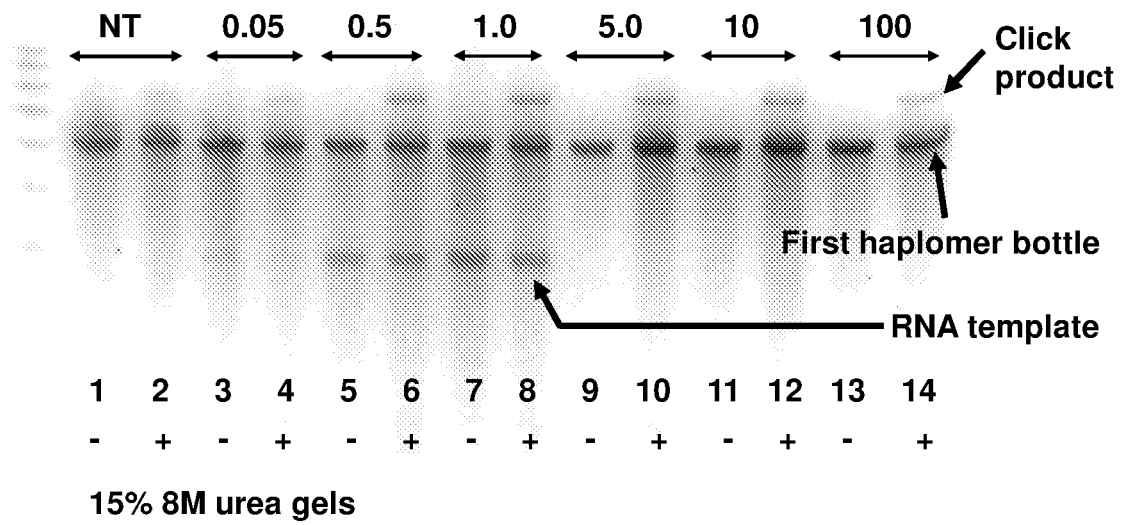
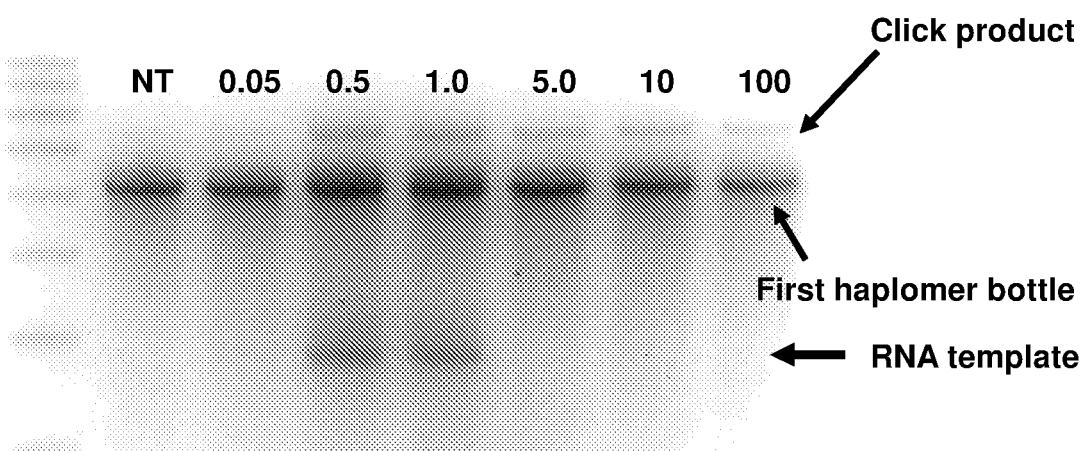
Figure 13

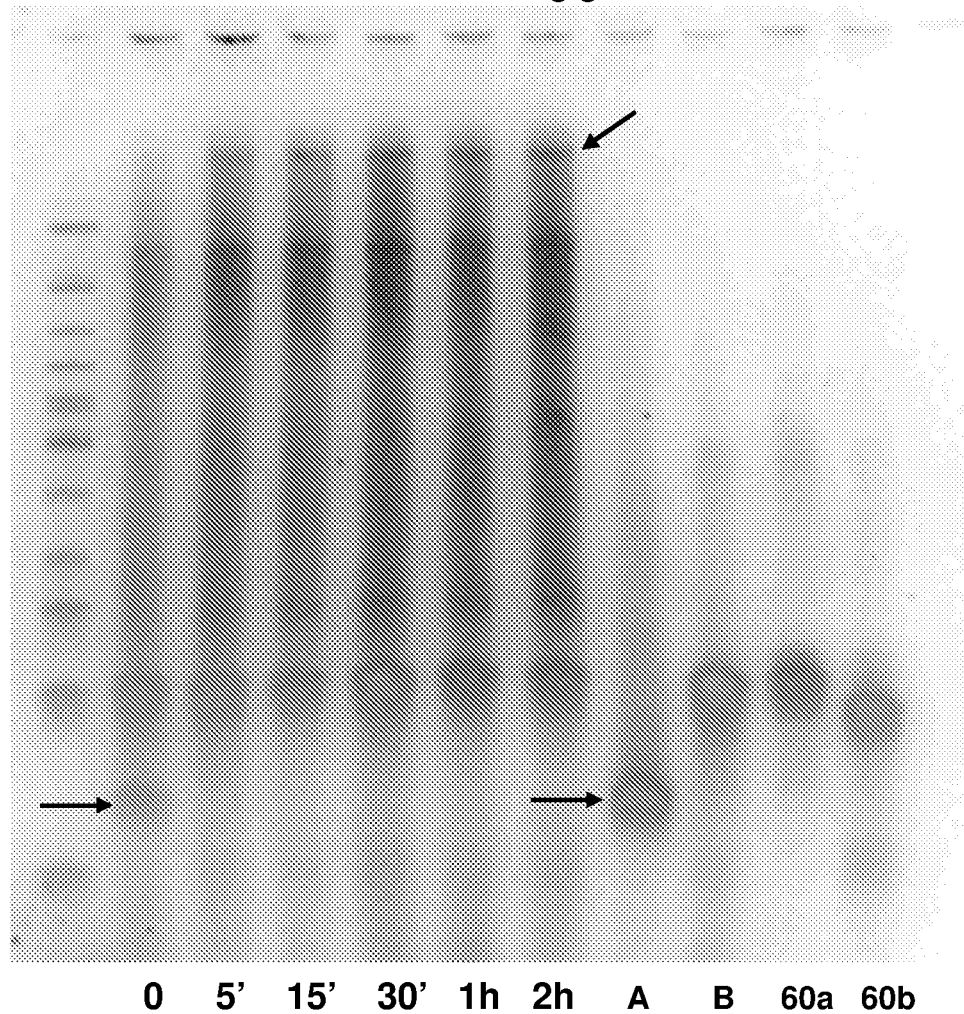

Locked Model Oligos - Hybridization Kinetics
10% non-denaturing gel 0  5'  15'  30'  1h  2h    A   B   60a 60b Bottle / HPV target 37° C annealing time-course (2-fold molar excess of target)

Because of its pronounced secondary structure, the 'bottle' oligo (arrows) migrates significantly faster than non-structured 60-mers on non-denaturing gels.

When the bottle oligo anneals with HPV, it no longer migrates at the same position. This was used in a time-course to test the rate of hybridization.
(See gel lanes)

Figure 14

EBNA1 coding sequence - with approximate boundaries of repeat region

ATGTCTGACGAGGGGCCAGGTACAGGACCTGGAAATGGCCTAGGAGAGAAGGGAGACAC
ATCTGGACCAGAAGGCTCCGGCGGCAGTGGACCTCAAAGAAGAGGGGGTGATAACCATG
GACGAGGACGGGGAAGAGGACGAGGACGAGGAGGCGGAAGACCAGGAGCCCCGGGCGGC
TCAGGATCAGGGCCAAGACATAGAGATGGTGTCCGGAGACCCCAAAAACGTCCAAGTTG
CATTGGCTGCAAAGGGACCCACGGTGGAACAGGAGCAGGAGCAGGAGCGGGAGGGGCAG
} 5'-region GAGCAGGAGGGGCAGGAGCAGGAGGAGGGGCAGGAGCAGGAGGAGGGGCAGGAGGGGCA
GGAGGGGCAGGAGGGGCAGGAGCAGGAGGAGGGGCA<u>GGAGCAGGAGGAGGGGCAGGA</u>GG
GGCAGGAGGGGCAGGAGCAGGAGGAGGGGCA<u>GGAGCAGGAGGAGGGGCAGGA</u>GGGGCAG
GAGCAGGAGGAGGGGCAGGAGGGGCAGGAGGGGCAGGAGCAGGAGGAGGGGCA<u>GGAGCA</u>
<u>GGAGGAGGGGCAGGA</u>GGGGCAGGAGCAGGAGGAGGGGCAGGAGGGGCAGGAGGGGCAGG
AGCAGGAGGAGGGGCAGGAGCAGGAGGGGCAGGAGGGGCAGGAGGGGCAGGAGCAGGAG
GGGCAGGAGCAGGAGGAGGGGCAGGAGGGGCAGGAGGGGCAGGAGCAGGAGGGGCAGGA
GCAGGAGGGGCAGGAGCAGGAGGGGCAGGAGCAGGAGGGGCAGGAGGGGCAGGAGCAGG
AGGGGCAGGAGGGGCAGGAGCAGGAGGGGCAGGAGGGGCA**GGAGCAGGAGGAGGGGCAG
GAGGGGCAGGAGCAGGAGGAGGGGCAGGA**GGGGCAGGAGCAGGAGGGGCAGGAGGGGCA
GGAGCAGGAGGGGCAGGAGGGGCAGGAGCAGGAGGGGCAGGAGGGGCA**GGAGCAGGAGG
AGGGGCAGGA**GCAGGAGGGGCAGGAGCAGGAGGTGGAGGCCGGGGTCGAGGAGGCAGTG
} Repeat segment GAGGCCGGGGTCGAGGAGGTAGTGGAGGCCGGGGTCGAGGAGGTAGTGGAGGCCGCCGG
GGTAGAGGACGTCAAAGAGCCAGGGGGGGAAGTCGTGAAAGAGCCAGGGGGAGAGGTCG
TGGACGTGGAGAAAAGAGGCCCAGGAGTCCCAGTAGTCAGTCATCATCATCCGGGTCTC
CACCGCGCAGGCCCCCTCCAGGTAGAAGGCCATTTTTCCACCCTGTAGGGGAAGCCGAT
TATTTTGAATACCACCAAGAAGGTGGCCCAGCTGGTGAGCCTGACGTGCCCCCGGGAGC
GATAGAGCAGGGCCCCGCAGATGACCCAGGAGAAGGCCCAAGCACTGGACCCCGGGGTC
AGGGTGATGGAGGCAGGCGCAAAAAAGGAGGGTGGTTTGGAAAGCATCGTGGTCAAGGA
GGTTCCAACCCGAAATTTGAGAACATTGCAGAAGGTTTAAGAGCTCTCCTGGCTAGGAG
TCACGTAGAAAGGACTACCGACGAAGGAACTTGGGTCGCCGGTGTGTTCGTATATGGAG
GTAGTAAGACCTCCCTTTACAACCTAAGGCGAGGAACTGCCCTTGCTATTCCACAATGT
CGTCTTACACCATTGAGTCGTCTCCCCTTTGGAATGGCCCCTGGACCCGGCCCACAACC
TGGCCCGCTAAGGGAGTCCATTGTCTGTTATTTCATGGTCTTTTTACAAACTCATATAT
TTGCTGAGGTTTTGAAGGATGCGATTAAGGACCTTGTTATGACAAAGCCCGCTCCTACC
TGCAATATCAGGGTGACTGTGTGCAGCTTTGACGATGGAGTAGATTTGCCTCCCTGGTT
TCCACCTATGGTGGAAGGGGCTGCCGCGGAGGGTGATGACGGAGATGACGGAGATGAAG
GAGGTGATGGAGATGAGGGTGAGGAAGGGCAGGAGTGA
} 3'-region Bold text =
Repeat region target copies
Underlined text =
Overlapping repeat targets

Figure 15

AGTTCCAGGAGCAGGAGGAGGGGCAGGAGCAGGAG

EBNA1 first haplomer bottle hybridized with model target

AGTTCCA                    GCAGGAG
                GGAGCAGGAGGAGGGGCAGGA
TGAGCTCTGCAGAG ‎‎‎‎‎‎‎‎‎‎‎‎‎‎‎‎‎‎‎‎‎‎‎‎‎‎ CTCTGCAGAGCTCA-GCT-HEX -5'
                                          GACGTCTCGAGT-  AE - 3'
                                                     TCTT

EBNA1 Second haplomer

METHODS FOR PREVENTING TITRATION OF BIMOLECULAR TEMPLATED ASSEMBLY REACTIONS BY STRUCTURALLY-DETERMINED DIFFERENTIAL HYBRIDIZATIONS

FIELD

The present disclosure is directed, in part, to nucleic acid molecules, and kits comprising the same, for producing templated assembly products for a cell.

BACKGROUND

A goal of drug development is delivering potent bio-therapeutic interventions to pathogenic cells, such as virus infected cells, neoplastic cells, cells producing an autoimmune response, and other dysregulated or dysfunctional cells. Examples of potent bio-therapeutic interventions capable of combating pathogenic cells include toxins, pro-apoptotic agents, and immunotherapy approaches that re-direct immune cells to eliminate pathogenic cells. Unfortunately, developing these agents is extremely difficult because of the high risk of toxicity to adjacent normal cells or the overall health of the patient.

A method that has emerged to allow delivery of potent interventions to pathogenic cells while mitigating toxicity to normal cells is targeting of therapeutics by directing them against molecular markers specific for pathogenic cells. Targeted therapeutics have shown extraordinary clinical results in restricted cases, but are currently limited in their applicability due to a lack of accessible markers for targeted therapy. It is extremely difficult, and often impossible, to discover protein markers for many pathogenic cell types.

More recently, therapies targeted to nucleic acid targets specific to pathogenic cells have been developed. Existing nucleic acid-targeted therapies, such as siRNA, are able to down-modulate expression of potentially dangerous genes, but do not deliver potent cytotoxic or cytostatic interventions and thus are not particularly efficient at eliminating the dangerous cells themselves.

Hence, there exists a need to combat the poor efficacy and/or severe side effects of existing bio-therapeutic interventions. As described herein, novel structures can be assembled on cellular nucleic acid templates which define pathogenic or otherwise undesirable cell classes. Such templated assembly processes can be used to target the cell types of interest for destruction. Pairs of modified oligonucleotides carrying specially tailored and mutually reactive groups can assemble molecules with predetermined functions following co-annealing in spatial proximity on a target cellular template. In the conventional bimolecular approach (i.e., Template Assembly by Proximity-Enhanced Reactivity (TAPER)), a titration issue emerges when target templates are present in large amounts, in excess of levels of oligonucleotides that can practically be obtained intracellularly. This template titration effect reduces the functional assembly signal in inverse proportion to the increase in the template:oligonucleotide ratio. In this application, a means for circumventing this issue is described, which also has certain other advantages for the general TAPER process.

SUMMARY

The present disclosure provides nucleic acid molecules comprising: a) a first stem portion comprising from about 10 to about 20 nucleotide bases; b) an anti-target loop portion comprising from about 16 to about 40 nucleotide bases and having a first end to which the first stem portion is linked, wherein the anti-target loop portion is substantially complementary to a target nucleic acid molecule; c) a second stem portion comprising from about 10 to about 20 nucleotide bases linked to a second end of the anti-target loop portion, wherein the first stem portion is substantially complementary to the second stem portion; and d) a reactive effector moiety linked to either the first stem portion or the second stem portion. The $T_m$ of the anti-target loop portion:target nucleic acid molecule is greater than the $T_m$ of the first stem portion:second stem portion.

The present disclosure also provides kits comprising: a) a first nucleic acid molecule according to any one of claims 1 to 18; and b) a second nucleic acid molecule comprising from about 6 nucleotide bases to about 20 nucleotide bases, which comprises: i) a nucleotide portion that is substantially complementary to the stem portion of the first nucleic acid molecule that is linked to the reactive effector moiety: and ii) a reactive effector moiety which can chemically interact with the reactive effector molecule of the first nucleic acid molecule. The $T_m$ of the second nucleic acid molecule:first or second stem portion linked to the reactive effector moiety is less than or equal to the $T_m$ of the first stem portion:second stem portion.

The present disclosure also provides methods of producing a templated assembly product for a cell comprising: a) contacting a target nucleic acid molecule of the cell with a first nucleic acid molecule of any one of claims 1 to 18; and b) contacting the first nucleic acid molecule with a second nucleic acid molecule, wherein the second nucleic acid molecule comprises: i) a nucleotide portion that is substantially complementary to the stem portion of the first nucleic acid molecule that is linked to the reactive effector moiety; and ii) a reactive effector moiety which can chemically interact with the reactive effector molecule of the first nucleic acid molecule; resulting in the combination of the respective reactive effector moieties thereby producing the templated assembly product. The $T_m$ of the second nucleic acid molecule:first or second stem portion linked to the reactive effector moiety is less than or equal to the $T_m$ of the first stem portion:second stem portion.

BRIEF DESCRIPTION OF THE DRAWINGS

FIG. 2 shows a representative demonstration of template titration effect with an in vitro model using pyrene excimer-induced fluorescence (with SEQ ID NO:1, SEQ ID NO:2, and SEQ ID NO:3, as shown above).

FIG. 13 (panels A and B) shows a representative locked TAPER dose response with HPV oligonucleotide RNA template; panel A shows plus and minus click reactions from a test series, where varying amounts of RNA template were used as shown (NT=no template); where RNA amounts were greater than or equal to a five-fold molar excess of the haplomers (lanes 9-14), the RNA was removed by alkaline hydrolysis to avoid its interference with gel migration patterns; panel B shows samples from the same experiment, but here only the (+) click reactions are shown for ease of comparison.

FIG. 14 shows the kinetics of a representative annealing between target-complementary sequence of a bottle first effector structure, and the target itself.

FIG. 15 shows the EBNA1 coding sequence (SEQ ID NO:9), showing the repeat region between non-repetitive 5' and 3' regions, and the target specific repetitive sequence within the repeat region itself.

FIG. 17 shows a structure of a representative "unlocked" TAPER EBNA1 repeat-region oligonucleotide (5'-hexynyl-TTCGACTCGAGACGTCTCCTTCCTGCCCCTCCTCC TGCTCCGAGACGTCTCGAGT-3'; SEQ ID NO:10) in the presence of specific target (5'-AGTTGCAGGAGCAG-GAGGAGGGGCAGGAGCAGGAG-3'; SEQ ID NO:12) and hybridized to a second haplomer (5'-GACGTCTCGAGTTCTT-azide-3'; SEQ ID NO:11).

DESCRIPTION OF EMBODIMENTS

Figure 1:
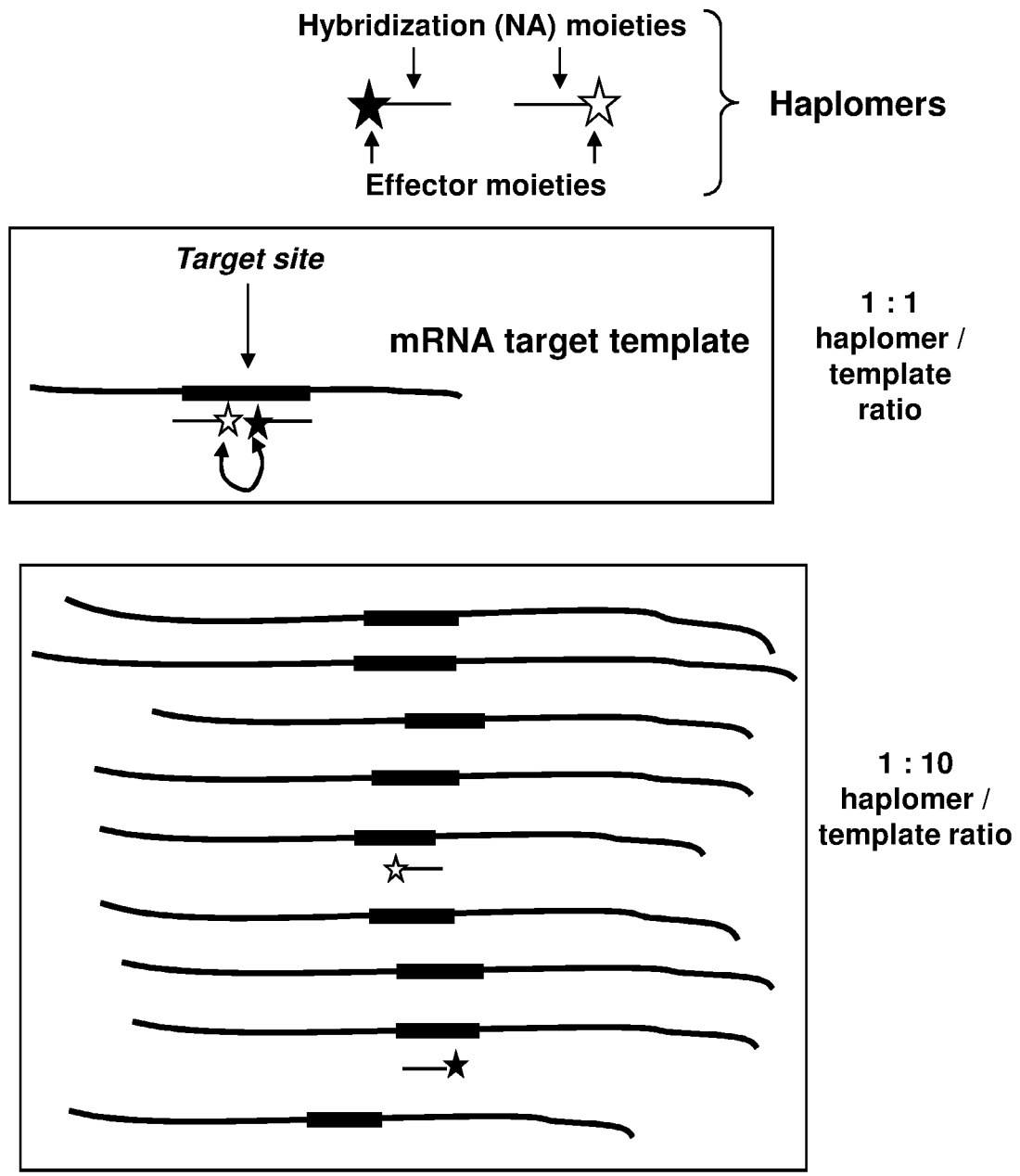
FIG. 1 shows a representative schematic depiction of how template titration occurs with excess target mRNA (for example, HPV DNA target nucleic acid molecule; 5'-TAACT GTCAAAAGCCACTGTGTCCT-GAAGAAAAGCAAAGACATCTGGACAAAAAGC-3'; SEQ ID NO:1) (5'-UAACUGUCAAAAGCCACUGUGU-CCUGAAGAAAAGCAAAGACAU CUGGACAAAAAGC-3' RNA sequence produced therefrom; SEQ ID NO:23) for bimolecular templated assembly by the TAPER process; curved line with arrows denotes proximity-induced reaction between the reactive components of the indicated haplomers (for example 5'-UCCAG AUGUCUUUGC-3' (SEQ ID NO:2) and 5'-UUUC-UUCAGGACACAG-3' (SEQ ID NO:3)).

Certain exemplary embodiments will now be described to provide an overall understanding of the principles of the structure, function, manufacture, and use of the compositions and methods disclosed herein. One or more examples of these embodiments are illustrated in the accompanying drawings. Those skilled in the art will understand that the compositions and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

As used herein, the singular forms "a," "an," and "the" include plural references unless the content clearly dictates otherwise. The terms used in this disclosure adhere to standard definitions generally accepted by those having ordinary skill in the art. In case any further explanation might be needed, some terms have been further elucidated below.

As used herein, the phrases "active effector structure" and "effector structure" are used interchangeably to refer to the active portion of a templated assembly product produced upon the combination of reactive effector moieties that triggers a desired effect.

As used herein, the phrase "anti-target loop portion" refers to a portion of a haplomer that facilitates sequence-specific binding to a target nucleic acid molecule.

As used herein, the term "base" refers to a molecule containing a purine or pyrimidine group, or an artificial analogue, that forms a binding pair with another corresponding base via Watson-Crick or Hoogsteen bonding interactions. Bases further contain groups that facilitate covalently joining multiple bases together in a polymer, such as an oligomer. Non-limiting examples include nucleotides, nucleosides, peptide nucleic acid residues, or morpholino residues.

As used herein, the terms "bind," "binds," "binding," and "bound" refer to a stable interaction between two molecules that are close to one another. The terms include physical interactions, such as chemical bonds (either directly linked or through intermediate structures), as well as non-physical interactions and attractive forces, such as electrostatic attraction, hydrogen bonding, and van der Waals/dispersion forces.

As used herein, the phrase "bioconjugation chemistry" refers to the chemical synthesis strategies and reagents that ligate common functional groups together under mild conditions, facilitating the modular construction of multi-moiety compounds.

As used herein, the phrase "chemical linker" refers to a molecule that binds one haplomer to another haplomer or one moiety to another moiety on different compounds. A linker may be comprised of branched or unbranched covalently bonded molecular chains.

As used herein, the phrase "dosage unit form" refers to physically discrete units suited as unitary dosages for the subjects to be treated.

As used herein, the phrase "effector structure-triggered agent" refers to an exogenously-produced compound or cell capable of initiating a desired activity upon binding to an effector structure.

As used herein, the phrase "effector structure-triggered agent" refers to an exogenously produced compound or cell capable of initiating a desired activity upon binding to an effector structure.

As used herein, the term "haplomer" refers to the nucleic acid recognition moiety that binds to a target nucleic acid template in a sequence-specific manner and participates in product formation during nucleic acid templated assembly. Also included herein are "derivatives" or "analogs" such as salts, hydrates, solvates thereof, or other molecules that have been subjected to chemical modification and maintain the same biological activity or lack of biological activity, and/or ability to act as a haplomer, or function in a manner consistent with a haplomer.

As used herein, the phrase "non-traceless bio-orthogonal chemistry" refers to a reaction involving selectively-reactive moieties in which part or all of the structure of the selectively-reactive moieties is retained in the product structure.

As used herein, the phrase "nucleic acid templated assembly" refers to the synthesis of a effector structure or structures on a target nucleic acid molecule, such that the effector structure formation can be facilitated by haplomers being assembled in proximity when bound to the target nucleic acid molecule.

As used herein, the terms "oligomer" and "oligo" refer to a molecule comprised of multiple units where some or all of the units are bases capable of forming Watson-Crick or Hoogsteen base-pairing interactions, allowing sequence-specific binding to nucleic acid molecules in a duplex or multiplex structure. Non-limiting examples include, but are not limited to, oligonucleotides, peptide nucleic acid oligomers, and morpholino oligomers.

As used herein, the phrase "pathogenic cell" can refer to a cell that is capable of causing or promoting a diseased or an abnormal condition, such as a cell infected with a virus, a tumor cell, and a cell infected with a microbe, or a cell that produces a molecule that induces or mediates diseases that include, but are not limited to allergy, anaphylaxis, inflammation and autoimmunity.

As used herein, the phrase "pharmaceutically acceptable" refers to a material that is not biologically or otherwise unacceptable, that can be incorporated into a composition and administered to a patient without causing unacceptable biological effects or interacting in an unacceptable manner with other components of the composition.

As used herein, the phrase "pharmaceutically acceptable salt" means a salt prepared from a base or an acid which is acceptable for administration to a patient, such as a mammal (e.g., salts having acceptable mammalian safety for a given dosage regime).

As used herein, the phrase "reactive effector moiety" refers to a portion of a haplomer that enables formation of effector structure, such as through a chemical reaction with a corresponding haplomer, on an adjacent templated assembly. For example, a reactive effector moiety can react readily with a corresponding reactive effector moiety, but does not readily react with natural biomolecules.

As used herein, the term "salt" can include salts derived from pharmaceutically acceptable inorganic acids and bases and salts derived from pharmaceutically acceptable organic acids and bases and their derivatives and variants thereof.

As used herein, the term "sample" refers to any system that haplomers can be administered into, where nucleic acid templated assembly may occur. Examples of samples include, but are not limited to, fixed or preserved cells, whole organisms, tissues, tumors, lysates, or in vitro assay systems.

As used herein, the phrases "set of corresponding reactants" or "corresponding haplomers" refer to haplomers that come together on a single target nucleic acid molecule to take part in a templated assembly reaction.

As used herein, the term "superantigen" refers to an antigen that binds to a broad subset of T cells that express a particular variable (V) region.

As used herein, the phrase "target compartment" refers to a cell, virus, tissue, tumor, lysate, other biological structure, spatial region, or sample that contains target nucleic acid molecule(s), or a different amount of target nucleic acid molecules than a non-target compartment.

As used herein, the phrases "target nucleic acid sequence" and "target nucleic acid molecule" are used interchangeably and refer to a sequence of units or nucleic acids which are intended to act as a template for nucleic acid templated assembly.

As used herein, the phrase "templated assembly product," refers to the effector structure or structures formed by interaction, binding or reaction of one or more nucleic acid haplomers.

As used herein, the phrase "traceless bio-orthogonal chemistry" refers to a reaction involving reactive effector moieties in which a naturally occurring bond, such as an amide, is formed by elimination of part or all of the reactive effector moieties from the effector structure thus produced.

Nucleic acid molecules that are specific to designated cells of interest (whether these are represented by pathological tumor cells, abnormal immune cells, or any other cellular types) can be used as templates for the generation of novel structures (e.g., effector structures) by means of proximity-induced enhancement of molecular interactions (see, for example, PCT Publication No. WO 2014/197547). Such templated products can be designed to trigger cell death in various ways, or to modulate cellular activities. Cell-type specific nucleic acids can be sourced from specific transcribed mRNAs, or via nucleic acid aptamers which can serve to adapt non-nucleic acid targets for the provision of a defined template sequence.

The process by which nucleic acid molecules may permit templated assembly typically is bimolecular with respect to the template-complementary effector molecules bearing the relevant reactive effector moieties. Each functional molecule in these circumstances is called a "haplomer." While this process is highly effective under many circumstances, an inherent issue exists with such assembly systems simply by virtue of their haplomeric bimolecularity. Since two separate participants are involved, a molar excess of a target template (irrespective of its source) can titrate out copies of each haplomer, decreasing the probability that two haplomers will anneal to the same template (as required for proximity-induced induction of reactivity). The theoretical basis of this template-derived titration effect is depicted in FIG. 1. Hence, the conventional bimolecular TAPER process is potentially restricted by amounts of target template in excess of an optimal concentration range. In the case of tumors, there are numerous precedents for over-expression of many transcripts, some of which act as drivers of tumor proliferation. Consequently, the TAPER process could be effectively improved against such targets.

Figure 3:
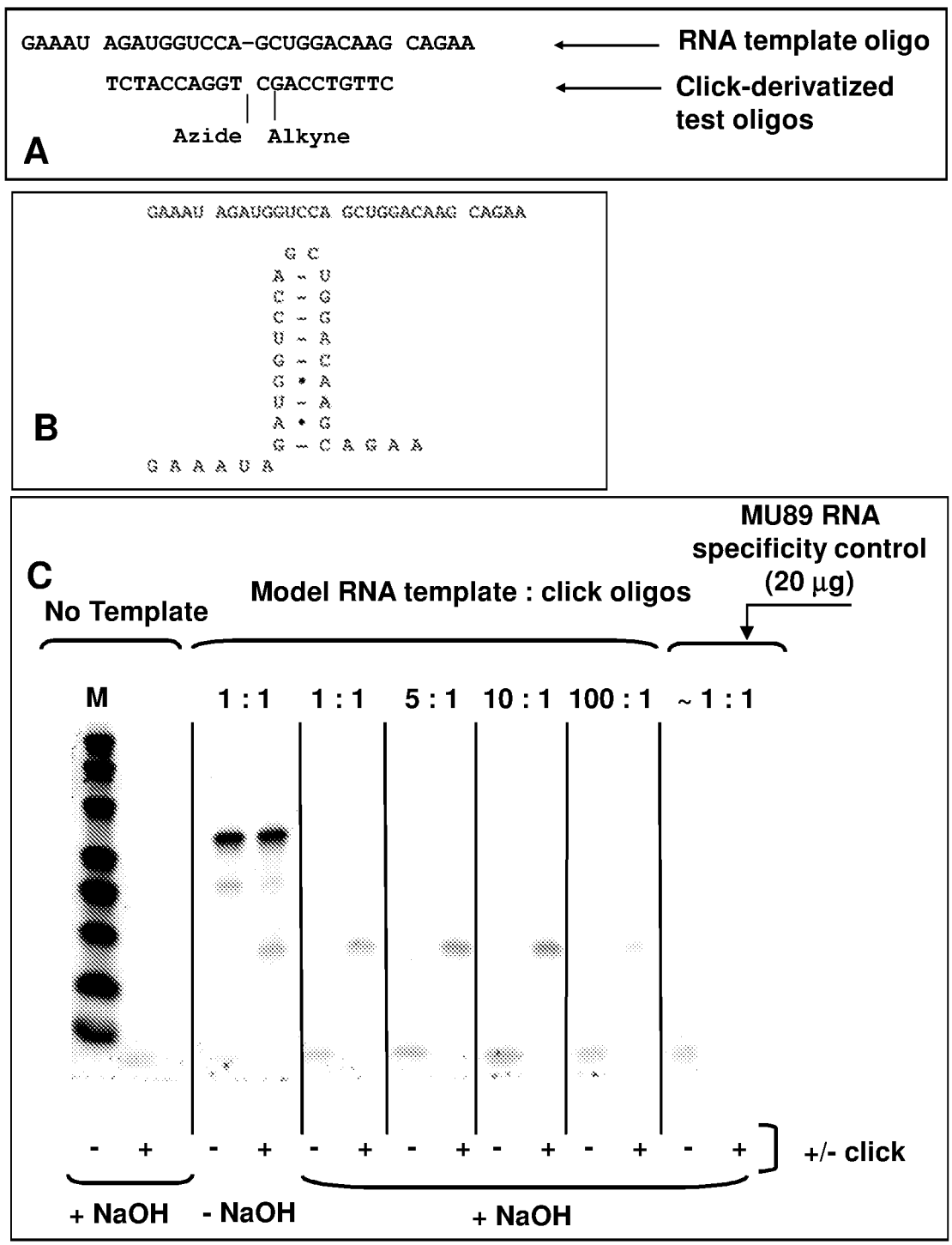
FIG. 3 (panels A, B, and C) shows a representative demonstration of template titration with model oligonucleotide-based click reactions; panel A shows a sequence of click oligonucleotides (5'-CTTGTCCAGC-alkyne-3' (SEQ ID NO:4); and 5'-azide-TGGACCATCT-3' (SEQ ID NO:5)) and RNA oligonucleotide template (5'-GAAAUAGAUG-GUCCAGCUGGA CAAGCAGAA-3' (SEQ ID NO:6)); panel B shows possible secondary structure with the same RNA template; panel C shows+/−click reactions with varying ratios of template to click oligonucleotides; excess template was removed with NaOH treatments where shown; MU89 melanoma cell RNA specificity control ratio based on assuming average size of mammalian mRNA=1500 bases; M=marker lane.

In addition, experimental evidence also suggests that titration effects can effect templated bimolecular reactions. In one such approach, pyrene fluorescence was used as a measure of template-induced molecular proximity. When planar pyrene molecules are closely juxtaposed on a molecular scale, excimer-based fluorescent emissions are known to be observable. Covalent appending of pyrene moieties to 5' and 3' ends of short oligonucleotides can be used to gauge bimolecular interactions based on hybridization-induced proximity, as a simple model for pairs of functional haplomers within the TAPER process. In such systems, a peak of fluorescent emission is observed when both model target template and pyrene-labeled complementary oligonucleotide pairs are at a mutual equimolar ratio, declining thereafter as the relative template amount rises (see, FIG. 2). In an alternate test model for template titration, DNA oligonucleotides equipped at their 5' or 3' ends with mutually-reactive click groups were used (5'-azide and 3'-linear alkyne), where the click reaction is catalyzed by univalent copper. Also, the model template in this scenario was an RNA oligonucleotide, which not only has the advantage of better representing an actual mRNA target, but also is readily removable after the click reaction by sodium hydroxide treatment. The latter feature is important when the products are analyzed by gel electrophoresis, since large amounts of template (as when excess template quantities are tested) can interfere with product band visualization. When the click oligonucleotide pairs were examined for Cu(I)-catalyzed activity in the presence of the RNA template, it was observed that the highest amount of product was seen with greater than 1:1 oligonucleotide:template molar ratios. However, at higher template levels, formation of product was almost obliterated (see, FIG. 3). The desire for increased target nucleic acid template levels for maximal product formation is interpreted as being due to the potential for significant secondary structure within the model RNA oligonucleotide target (see, FIG. 3). Where an equilibrium exists between the folded and linear (accessible) RNA forms, increased target nucleic acid template levels concomitantly increase the available amount of accessible target nucleic acid template. Nevertheless, at very high target nucleic acid template concentrations, the titration effect still occurs, and product formation decreases. These observations reinforce the target nucleic acid template titration effect, while at the same time showing that prediction of the extent of product formation impedance simply by target nucleic acid template concentration alone is not sufficient.

Figure 4:
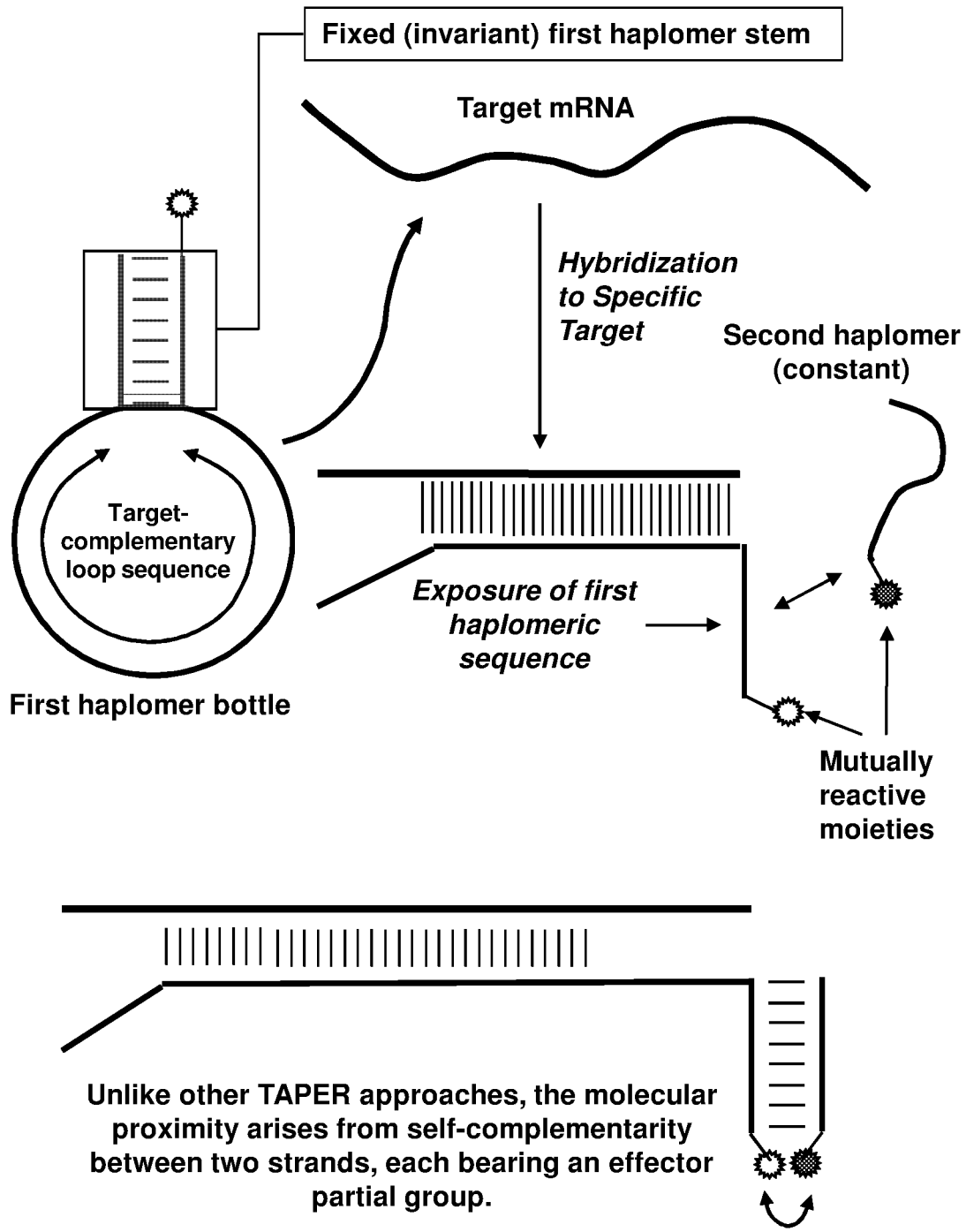
FIG. 4 shows a representative bimolecular "locked" approach for circumventing template titration effect.

In general, one solution to the target nucleic acid template titration effect for TAPER is devised by means of structurally-determined differential hybridizations. A distinction in this case from conventional TAPER is that the target nucleic acid sequence for haplomer binding does not correspond to a cellular nucleic acid. Here, the haplomer sequences are fixed and complementary to each other, where the first haplomer is "locked" by hybridization to a complementary sequence within the same longer oligonucleotide (see, FIG. 4). An internal anti-target loop portion sequence within this oligonucleotide structure corresponds to the target-complementary sequence. The structure comprising the first haplomer constrained by internal self-hybridization and an anti-target loop portion sequence that is complementary to the target nucleic acid molecule sequence is the "first haplomer" or "first haplomer bottle."

The present disclosure provides nucleic acid molecules comprising: a) a first stem portion comprising from about 10 to about 20 nucleotide bases; b) an anti-target loop portion comprising from about 16 to about 40 nucleotide bases and having a first end to which the first stem portion is linked, wherein the anti-target loop portion is substantially complementary to a target nucleic acid molecule; c) a second stem portion comprising from about 10 to about 20 nucleotide bases linked to a second end of the anti-target loop portion, wherein the first stem portion is substantially complementary to the second stem portion; and d) a reactive effector moiety linked to either the first stem portion or the second stem portion; wherein the $T_m$ of the anti-target loop portion: target nucleic acid molecule is greater than the $T_m$ of the first stem portion:second stem portion. A nucleic acid molecule comprising these features is referred to herein as: "first nucleic acid molecule", "first haplomer bottle", "first haplomer" and "bottle haplomer."

In some embodiments, the first nucleic acid molecule comprises a first stem portion that comprises from about 10 to about 20 nucleotide bases. In some embodiments, the first stem portion comprises from about 12 to about 18 nucleotide bases. In some embodiments, a reactive effector moiety is linked to the first stem portion.

In some embodiments, the first nucleic acid molecule comprises an anti-target loop portion that comprises from about 16 to about 40 nucleotide bases. In some embodiments, the anti-target loop portion comprises from about 18 to about 35 nucleotide bases. The anti-target loop portion has a first end to which the first stem portion is linked. The anti-target loop portion is substantially complementary to a target nucleic acid molecule.

In some embodiments, the anti-target loop portion can further comprise an internal hinge region, wherein the hinge region comprises one or more nucleotides that are not complementary to the target nucleic acid molecule. In some embodiments, the hinge region comprises from about 1 nucleotide to about 6 nucleotides, from about 1 nucleotide to about 5 nucleotides, from about 1 nucleotide to about 4 nucleotides, from about 1 nucleotide to about 3 nucleotides, or 1 or 2 nucleotides.

The target nucleic acid molecule template (complementary to the anti-target loop portion of a general first haplomer bottle) for all locked TAPER embodiments can be comprised of any desired nucleic acid sequence capable of hybridizing with the specific anti-loop region portion itself. Any single-stranded nucleic acid molecule with an accessible sequence is potentially targetable. These include, but are not limited to, cellular RNAs, mRNA, genomic or organellar DNA, episomal or plasmid DNA, viral DNA or RNA, miRNA, rRNA, snRNA, tRNA, short and long non-coding RNAs, and any artificial sequences used for templating purposes, or any other biological or artificial nucleic acid sequence. Artificial sequences include, but are not limited to, aptamers and macromolecular-nucleic acid conjugates. Aptamer templates are also included, where these are designed to convert a non-nucleic acid cellular product into a targetable sequence for any form of TAPER, including locked TAPER. In some embodiments, the target nucleic acid molecule hybridization site is kept as short as possible while: 1) maintaining specificity within a complex transcriptome or other complex targets; and 2) maintaining the locked TAPER design guidelines described herein.

Any cell, virus, tissues, spatial regions, lysate, or other subcomponent of a sample that contains a target nucleic acid can provide the target nucleic acid. Target compartments that contain the target nucleic acid can include, but are not limited to, pathogenic cells, cancer cells, viruses, host cells infected by a virus or other pathogen, or cells of the immune system that are contributing to autoimmunity such as cells of the adaptive or innate immune systems, transplant rejection, or an allergic response. In some embodiments, a target nucleic acid can be present in a virus or cell infected by a virus, but absent in healthy cells. Some non-limiting examples of virus can include DNA viruses, RNA viruses, or reverse transcribing viruses. In some embodiments, a target nucleic acid can be present in a tumor or cancerous cell, but absent in healthy cells. Some non-limiting examples of cancers can include those caused by oncoviruses, such as the human papilloma viruses, Epstein-Barr virus, hepatitis B virus, hepatitis C virus, human T-lymphotropic viruses, Merkel cell polyoma virus, and Kaposi's sarcoma-associated herpesvirus. In some embodiments, a target nucleic acid can be present in an infectious agent or microbe, or a cell infected by an infectious agent or microbe but is absent in healthy cells. Some non-limiting examples of infectious agents or microbes can include viruses, bacteria, fungi, protists, prions, or eukaryotic parasites.

The target nucleic acid sequence can also be a fragment, portion or part of a gene, such as an oncogene, a mutant gene, an oncoviral gene, a viral nucleic acid sequence, a microbial nucleic acid sequence, a differentially expressed gene, and a nucleic acid gene product thereof. Examples of cancer-specific target nucleic acids can include mutant oncogenes, such as mutated ras, HRAS, KRAS, NRAS, BRAF, EGFR, FLT1, FLT4, KDR, PDGFRA, PDGFRB, ABL1, PDGFB, MYC, CCND1, CDK2, CDK4, or SRC genes; mutant tumor suppressor genes, such as TP53, TP63, TP73, MDM1, MDM2, ATM, RB1, RBL1, RBL2, PTEN, APC, DCC, WT1, IRF1, CDK2AP1, CDKN1A, CDKN1B, CDKN2A, TRIM3, BRCA1, or BRCA2 genes; and genes expressed in cancer cells, where the gene may not be mutated or genetically altered, but is not expressed in healthy cells of a sample at the time of administration, such as carcinoembryonic antigen.

In some embodiments, the target nucleic acid can be present in a differential amounts or concentrations in the target compartments as compared to the non-target compartments. Examples include, but are not limited to, genes expressed at a different level in cancer cells than in healthy cells, such as myc, telomerase, HER2, or cyclin-dependent kinases. In some embodiments, the target nucleic acid molecule can be a gene that is at least 1.5x-fold differentially expressed in the target versus the non-target compartments. Some examples of these can include, but are not limited to, genes related to mediating Type I allergic responses, for which target RNA molecules contain immunoglobulin epsilon heavy chain sequences; genes expressed in T cell subsets, such as specific T cell receptors (TCRs) which recognize self-antigens in the context of particular major histocompatibility (MHC) proteins like proinsulin-derived peptide and clonally-specific mRNAs containing a or 13 variable-region sequences, derived from diabetogenic CD8+ T cells; and cytokines whose production may have adverse outcomes through exacerbation of inflammatory responses, including but not limited to TNF-alpha, TNF-beta, IL-1, IL-2, IL-4, IL-6, IL-8, IL-10, IL-12, IL-15, IL-17, IL-18, IL-21, IL-22, IL-27, IL-31, IFN-gamma, OSM, and LIF.

In some embodiments, a target nucleic acid is present in target compartments and an acceptable subgroup of non-target compartments, but not in a different or distinct subgroup of non-target compartments. Some non-limiting examples can include genes expressed in cancer cells and limited to classes of healthy cells, such as cancer-testis antigens, survivin, prostate-specific antigen, carcinoembryonic antigen (CEA), alpha-fetoprotein and other onco-fetal proteins. Also, many tissues and organs are not essential to otherwise healthy life in the face of serious disease. For example, melanocyte antigens, such as Melan-A/MART-1 and gp100 are expressed on many malignant melanomas as well as normal melanocytes, and therapies that target these antigens can destroy both tumors and normal melanocytes, resulting in vitiligo, but major tumor reduction. Likewise, the reproductive organs may be surgically removed, such as testis, ovary and uterus, as well as associated organs such as breast and prostate may be targeted when tumors of these tissues arise, and destruction of normal tissues within these organs may be a tolerable consequence of therapy. Furthermore, some cells that produce hormones, such as thyroxine and insulin can be replaced with the relevant protein, allowing potential targeting of normal cells that may exist in the presence of tumors of these origins.

Target nucleic acid molecules can also include novel sequences, not previously identified. In some embodiments, a sample or samples can be evaluated by sequence analysis, such as next-generation sequencing, whole-transcriptome (RNA-seq) or whole-genome sequencing, microarray profiling, serial analysis of gene expression (SAGE), to determine the genetic makeup of the sample. Target nucleic acid molecules can be identified as those present in target compartments, but not present in non-target compartments, or present in differential amounts or concentrations in target compartments as compared to non-target compartments. Sequences identified by these methods can then serve as target nucleic acid molecules.

In some embodiments, the first nucleic acid molecule comprises a second stem portion that comprises from about 10 to about 20 nucleotide bases. In some embodiments, the second stem portion comprises from about 12 to about 18 nucleotide bases. The second stem portion is linked to a second end of the anti-target loop portion. The first stem portion is substantially complementary to the second stem portion. In some embodiments, a reactive effector moiety is linked to the second stem portion.

In some embodiments, the first nucleic acid molecule comprises the nucleotide sequence 5'-ACTCGA-GACGTCTCCTTGTCTTTGCTTTTCTTCAGGACACA-GTGGCGA GACGTCTCGAGT-3' (SEQ ID NO:13) or 5'-ACTCGAGACGTCTCCTTCCTGCCCCTC CTCCTGCTCCGAGACGTCTCGAGT-3' (SEQ ID NO:14).

The present disclosure also provides nucleic acid molecules comprising from about 6 nucleotide bases to about 20 nucleotide bases, which comprises: a nucleotide portion that is substantially complementary to the stem portion (either the first stem portion or the second stem portion) of the first nucleic acid molecule that is linked to the reactive effector moiety; and a reactive effector moiety which can chemically interact with the reactive effector molecule of the first nucleic acid molecule; wherein the $T_m$ of the second nucleic acid molecule:first or second stem portion linked to the reactive effector moiety is less than or equal to the $T_m$ of the first stem portion:second stem portion. A nucleic acid molecule comprising these features is referred to herein as: "second nucleic acid molecule" and "second haplomer."

In some embodiments, the second nucleic acid molecule comprises from about 6 to about 20 nucleotide bases. In some embodiments, the second nucleic acid molecule comprises from about 8 to about 15 nucleotide bases.

In some embodiments, the second nucleic acid molecule comprises the nucleotide sequence 5'-AGCTCTCGAGT-3' (SEQ ID NO:15), or 5'-GACGTCTCGAGT-3' (SEQ ID NO:16).

In some embodiments, the first nucleic acid molecule comprises the nucleotide sequence of SEQ ID NO:13, and the second nucleic acid molecule comprises the nucleotide sequence of SEQ ID NO:15; or the first nucleic acid molecule comprises the nucleotide sequence of SEQ ID NO:14, and the second nucleic acid molecule comprises the nucleotide sequence of SEQ ID NO:16.

For the nucleic acid molecules described herein, the length of the particular nucleic acid molecule is less important than the $T_m$ of the duplex formed by the interaction of the nucleic acid molecule, or portion thereof, with another nucleic acid molecule, or portion thereof. For example, the $T_m$ of the duplex formed by the interaction of the anti-target loop portion with the target nucleic acid molecule (e.g., anti-target loop portion:target nucleic acid molecule) is greater than the $T_m$ of the duplex formed by the interaction of the first stem portion of the first nucleic acid molecule with the second stem portion of the first nucleic acid molecule (e.g., first stem portion:second stem portion). In some embodiments, the $T_m$ of the first stem portion:second stem portion subtracted from the $T_m$ of the anti-target loop portion:target nucleic acid molecule is from about 10° C. to about 40° C. In some embodiments, the $T_m$ of the first stem portion:second stem portion subtracted from the $T_m$ of the anti-target loop portion:target nucleic acid molecule is from about 10° C. to about 20° C. In some embodiments, the $T_m$ of the first stem portion:second stem portion is from about 40° C. to about 50° C. In some embodiments, the of the anti-target loop portion:target nucleic acid molecule is from about 60° C. to about 80° C. In some embodiments, the $T_m$ of the duplex formed by the interaction of the second nucleic acid molecule with either the first stem portion or the second stem portion, whichever stem portion is linked to the reactive effector moiety (e.g., second nucleic acid molecule:first or second stem portion linked to the reactive effector moiety), is less than or equal to the $T_m$ of the first stem portion:second stem portion. In some embodiments, the $T_m$ of the duplex formed by the second nucleic acid molecule and the first or second stem portion linked to the reactive effector moiety subtracted from the $T_m$ of the first stem portion:second stem portion is from about 0° C. to about 20° C. In some embodiments, the $T_m$ of the duplex formed by the nucleic acid molecule and the first or second stem portion linked to the reactive effector moiety subtracted from the $T_m$ of the first stem portion:second stem portion is from about 5° C. to about 10° C. In some embodiments, the $T_m$ of the duplex formed by the second nucleic acid molecule and the first or second stem portion linked to the reactive effector moiety is from about 30° C. to about 40° C.

In addition, translating the $T_m$ information above into specific lengths of the nucleic acid molecules described herein also depends on the GC content of each nucleic acid molecule. For example, the length of a suitable HPV model target nucleic acid molecule is 30 bases (having a $T_m$ of 70° C.), while that for the EBV model target nucleic acid molecule is only 21 bases (having a $T_m$ of 69° C.), owing to its greater % GC.

This structural arrangement is designed such that in the absence of target nucleic acid molecule template, the locked first haplomer bottle (e.g., the first nucleic acid molecule) does not significantly hybridize to its complementary second haplomer (e.g., the second nucleic acid molecule), and thus template-directed product assembly is not promoted under such conditions. When the specific target template is present, on the other hand, the first haplomer bottle is "unlocked" by the formation of a more stable hybrid between the anti-target loop region of the bottle haplomer and the target nucleic acid molecule itself (see, FIG. 4). Once this occurs, the first stem portion of the bottle haplomer that is linked to the reactive moiety is free to hybridize to the available second haplomer, with resulting proximity between the mutually reactive effector moieties on both, and generation of a specific assembly reaction (see, FIG. 4). It is the exposure of the accessible first haplomer bottle that renders the process resistant to the template titration effect, since there is a 1:1 correspondence between the binding of anti-target loop portion to the corresponding target nucleic acid molecule and generation of first haplomer accessibility for the second haplomer. This can be expressed as:

(1)

Figure 5:
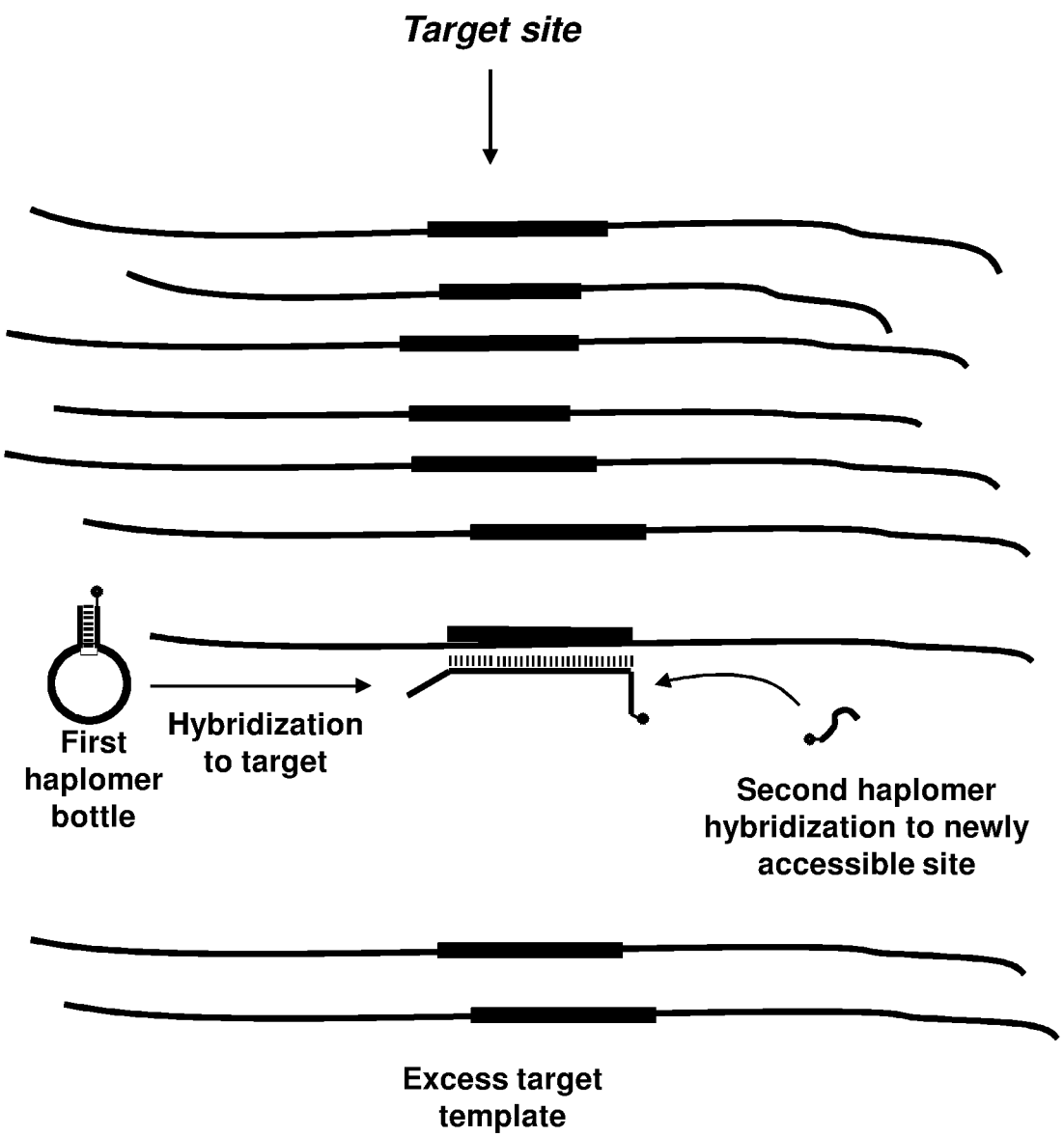
FIG. 5 shows a representative schematic depiction of the operation of a locked haplomer in the presence of excess target template; the locked haplomer bottle loop sequence hybridizes to the target more strongly than the self-complementarity that prevents access by the second effector in the absence of template; subsequently, the target site for the second effector is rendered accessible following the target-specific hybridization event.

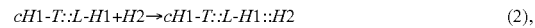
(2), where B[L]cH1::H1 is the first haplomer bottle with the anti-target loop region (L); T is the target nucleic acid molecule; cH1 is the complement to the first haplomer sequence H1; T::L-H1 is the anti-target loop region duplex with the exposed first haplomer sequence; and H2 is the second haplomer. Since the second haplomer (H2) can only hybridize to the first haplomer (H1) after the latter has been exposed through the presence of the specific nucleic acid molecule template, a template excess cannot have a titration effect, and indeed is beneficial through shifting equation (1) further to the right, thus providing more available HE The unlocking of a single copy of the first haplomer bottle in the presence of excess target nucleic acid molecule template is depicted schematically in FIG. 5. Since the exposed first haplomer sequence H1 is unique and designed to be absent from the target expressed genome, spurious hybridization between H1 and an off-target sequence is minimal. This applies also to the designed complement to H1, the second haplomer H2.

Figure 6:
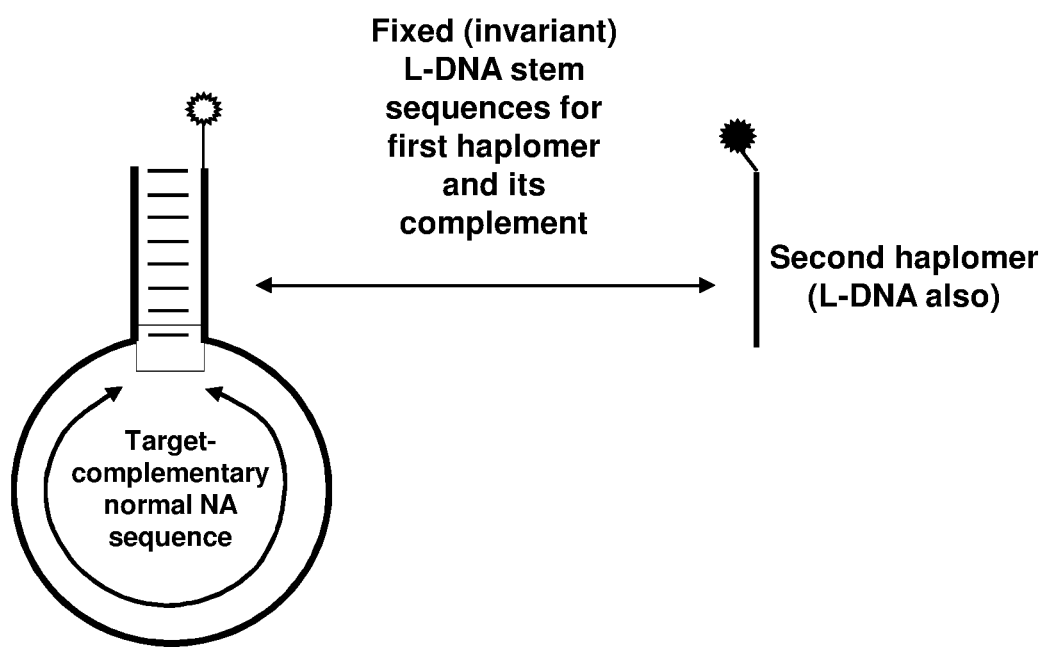
FIG. 6 shows a representative use of hybrid nucleic acids for locked TAPER, consisting of a bottle structure where the anti-target loop region sequence is composed of normal nucleic acids (bearing D-ribose), and the stem portion comprising the reactive effector moiety and its complement are composed of DNA with L-ribose (L-DNA).

As described above, the specificity of the H1::H2 interaction can be enhanced by rendering the hybridization bio-orthogonal. This can be achieved by, for example, synthesizing a hybrid first haplomer bottle where the H1 and H1-complementary (cH1) sequences are comprised of DNA bearing L-ribose, or L-DNA (see, FIG. 6). Since DNA can only form duplexes between homochiral complementary single strands, when the H1 sequence is exposed following hybridization of the (normal) anti-target loop sequence with cellular target, it follows that H1 can only form a duplex with a corresponding H2 L-DNA sequence.

In all locked TAPER embodiments, one can modulate the hybridization $T_m$ values of each component in line with the desired differential hybridization effects. Thus, the designed thermal stabilities of relevant components should be: T::L>>cH1::H1>H1::H2. It is notable that the sequences of cH1::H1 and H1::H2 are similar but not identical, in order to ensure that the sequestration of the H1 haplomer sequence within the first haplomer bottle is marginally more stable than the H1::H2 inter-haplomer duplex. By this means, mixtures of the first haplomer bottle and the second haplomer H2 in the absence of target will favor retention of the cH1::H1 configuration rather than formation of H1::H2.

Figure 7:
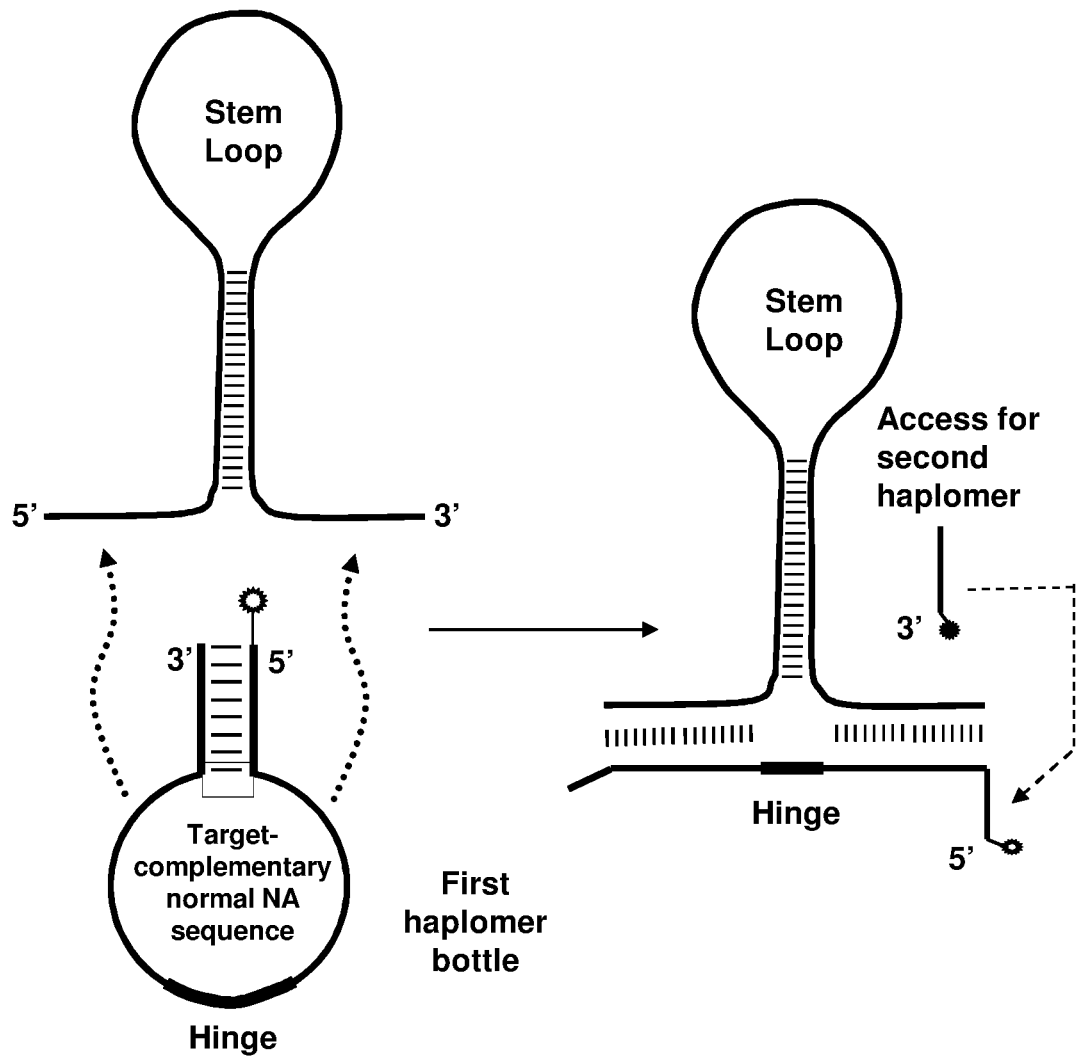
FIG. 7 shows a representative locked TAPER having an alternative template architecture, where the template-mediated first haplomer bottle opening occurs via discontinuous sites brought into spatial proximity on the exterior of a stem-loop structure.
Figure 8:
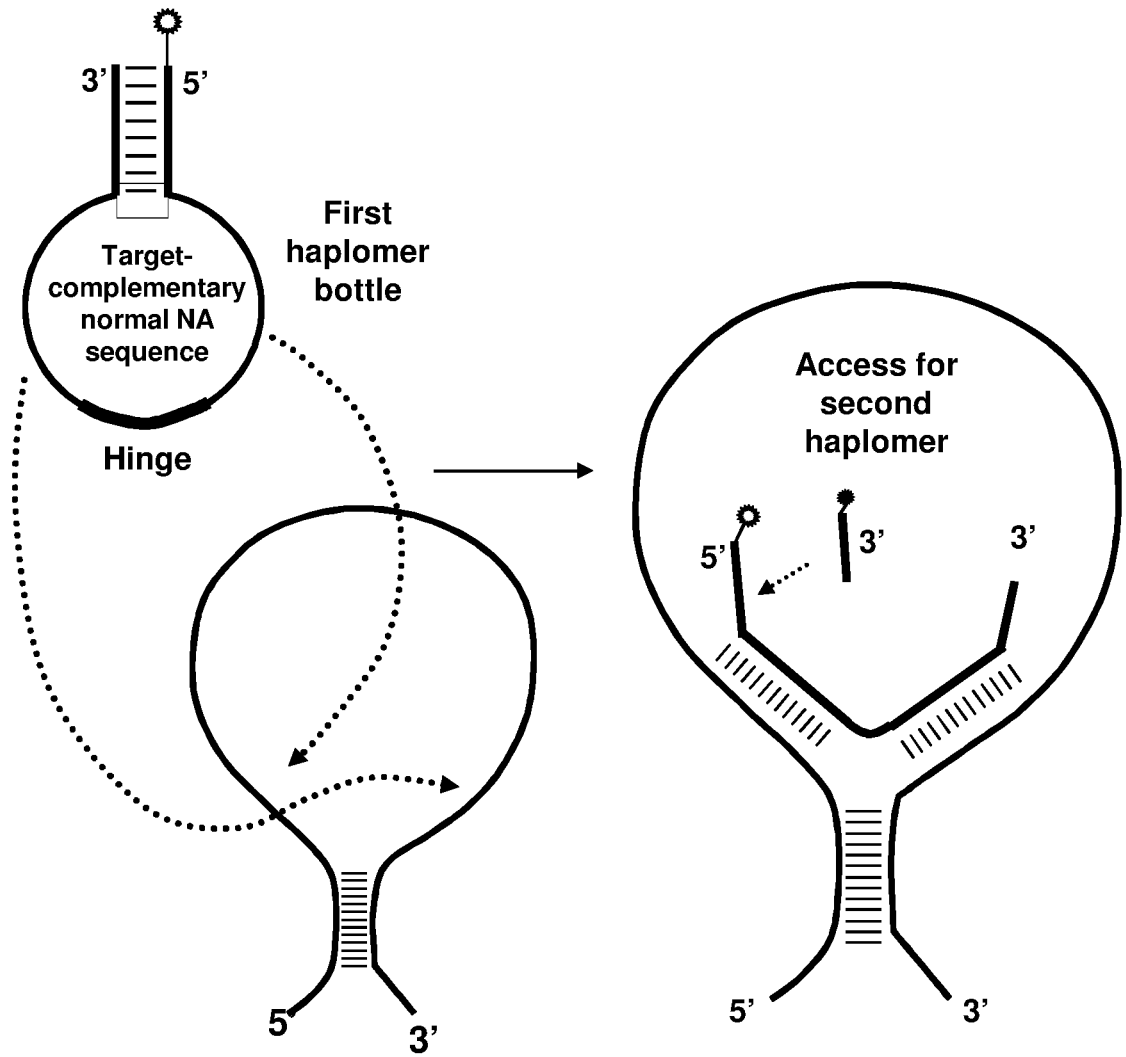
FIG. 8 shows a representative locked TAPER having an alternative template architecture, where the template-mediated first haplomer bottle opening occurs via discontinuous sites brought into spatial proximity in the interior loop of a stem-loop structure.

Within a locked TAPER system, when the two haplomers bearing click chemical groups (e.g., reactive effector moiety linked to a bio-orthogonal reactive molecule) or other modifications are in hybridization-mediated spatial proximity (see, FIG. 4), it is by virtue of their possessing mutual complementarity. This is quite distinct from conventional TAPER, where the spatial proximity is achieved by haplomer complementarity to a third-party template strand. Nevertheless, since the anti-target loop portion of a locked-TAPER first haplomer bottle hybridizes to a target nucleic acid molecule sequence in order to expose the recognition site for the second haplomer, the anti-target loop-target binding itself can occur via different architectures. These alternative structural arrangements can include hybridizations to discontinuous sites. Thus, the target hybridization of the locked TAPER oligonucleotide schematically depicted in FIG. 7 is achieved with discontinuous sites brought into spatial proximity in the exterior arms of a stem loop structure. Alternately, equivalent spatial proximity can be engendered by hybridization sites juxtaposed within a loop formed by a template secondary structure (see, FIG. 8). In both of these embodiments, the regions within the first haplomer loops that hybridize to discontinuous targets may be separated by an additional "hinge" sequence of $d(T)_N$, where N is from 1 to about 6 bases. The provision of such a hinge sequence is designed to confer flexibility between the two hybridizing segments, and minimize torsional strain on these regions.

In these alternative architectures for Locked TAPER, it is important to maintain the differential rules of hybridization stabilities for T::L>>cH1::H1>H1::H2 as described above. Locked TAPER accordingly has the unique feature whereby the TAPER assembly is always constant through haplomer mutual complementarity, but target hybridization can assume variable architectures. In other words, for conventional TAPER, the target hybridization and assembly-directing hybridizations coincide, but for locked TAPER they are distinct and separable.

In these embodiments, locked TAPER affords considerable advantages compared to conventional TAPER. These advantages include, for example, evasion of template titration, boosting of signal strength with high copy-number template, provision of bio-orthogonal hybridization, and the use of fixed haplomeric sequences. In the latter case, a single pair of specific haplomers (bearing bio-orthogonal reactive molecules) can be used for an indefinite number of targets, where the loop region of first haplomer bottles can be varied according to the desired target sequence complement. In addition, solving the template titration problem enables the targeting of repeat sequence motifs. Where N copies of a specific motif occurs in M steady-state copies of a transcript of interest, the total number of theoretically targetable motifs is N×M. In practice, not all such motifs may be accessible, and the targetable motif number per cell becomes <N×M, owing to secondary structural constraints. Nevertheless, attempting to target a repeated motif with conventional TAPER is very likely to suffer restrictions from template titration, when accessible N×M copy number becomes greater than the molar quantities of each separate haplomer achievable after delivery into a target cellular environment. No such restriction exists for locked-TAPER, and indeed, increased copy number from a repeat motif is an advantage in terms of the potential increase in read-out product assembly levels. In addition, the above observation that repeat motifs within a single transcript may vary in their accessibilities for TAPER purposes may be another inherent advantage of repeat motifs. In a dynamic cellular environment, where some single-copy mRNA motifs may have variable accessibility, multiple repeat motifs may increase the likelihood of access.

The locked TAPER process also uses a single segment for the hybridization that enables specific RNA targeting, in contrast to conventional TAPER, where two such sequences are used for each haplomer. Clearly, the length of these segment is a significant issue in terms of achieving the necessary specificity towards a target template. In the locked TAPER strategy, the length of the target-complementary loop sequence can be varied as desired, subject to the requirement that the Tm of loop::target is>>the bottle stem $T_m$. But in specific targeting circumstances, the length of the target sequence with locked TAPER could achieve the necessary specificity and still be less than the total sequence required for conventional bimolecular effector partials. Thus, targeting by locked TAPER approach may be less demanding than the conventional TAPER strategy.

In any of the nucleic acid molecules described herein, or any portion thereof, the nucleotide bases are selected from the group consisting of DNA nucleotides, RNA nucleotides, phosphorothioate-modified nucleotides, 2-O-alkylated RNA nucleotides, halogenated nucleotides, locked nucleic acid nucleotides (LNA), peptide nucleic acids (PNA), morpholino nucleic acid analogues (morpholinos), pseudouridine nucleotides, xanthine nucleotides, hypoxanthine nucleotides, 2-deoxyinosine nucleotides, DNA analogs with L-ribose (L-DNA), Xeno nucleic acid (XNA) analogues, or other nucleic acid analogues capable of base-pair formation, or artificial nucleic acid analogues with altered backbones, or any combination or mixture thereof.

For any of the nucleic acid molecules described herein, the complementarity with another nucleic acid molecule can be 100%. In some embodiments, one particular nucleic acid molecule can be substantially complementary to another nucleic acid molecule. As used herein, the phrase "substantially complementary" means from 1 to 10 mismatched base positions, from 1 to 9 mismatched base positions, from 1 to 8 mismatched base positions, from 1 to 7 mismatched base positions, from 1 to 6 mismatched base positions, from 1 to 5 mismatched base positions, from 1 to 4 mismatched base positions, from 1 to 3 mismatched base positions, and 1 or 2 mismatched base positions. In some embodiments, it is desirable to avoid reducing the $T_m$ of the anti-target loop portion:target nucleic acid molecule by more than 10% via mismatched base positions. The first haplomer bottle stem is designed with respect to second haplomer, and its structure is deliberately arranged to be somewhat more stable than the formation of the second haplomer duplex.

Any of the nucleic acid molecules described herein, or any portion thereof, can further comprise a linker between any one or more of the first stem portion and the anti-target loop portion, between the anti-target loop portion and the second stem portion, and between the second stem portion and the reactive effector moiety of the first nucleic acid molecule or between the second nucleic acid molecule and its reactive effector moiety. In some embodiments, the linker is selected from the group consisting of an alkyl group, an alkenyl group, an amide, an ester, a thioester, a ketone, an ether, a thioether, a disulfide, an ethylene glycol, a cycloalkyl group, a benzyl group, a heterocyclic group, a maleimidyl group, a hydrazone, a urethane, azoles, an imine, a haloalkyl, and a carbamate, or any combination thereof.

Each of the first nucleic acid molecule (e.g., first haplomer) and the second nucleic acid molecule (e.g., second haplomer) is linked to a reactive effector moiety. In some embodiments, the reactive effector moiety is selected from the group consisting of a peptide, a non-active portion of a peptidomimetic structure, a non-active portion of a drug, and a bioactive compound. In some embodiments, the reactive effector moiety is less than about 20 kDa. In some embodiments, the reactive effector moiety is less than about 10 kDa.

The effector structure generated by the processes described herein (via two reactive effector moieties) is the trigger that drives a desired action in a sample. Some examples of desired effector activity can include, but are not limited to, inducing an immune response, programmed cell death, apoptosis, non-specific or programmed necrosis, lysis, growth inhibition, inhibition of viral infection, inhibition of viral replication, inhibition of oncogene expression, modification of gene expression, inhibition of microbial infection, and inhibition of microbe replication, as well as combinations of these biological activities. In some embodiments, the effector structure can serve as a ligand for an antibody to induce an immune response at the site of the pathogenic cells, or to localize antibody-directed therapies, such as an antibody bearing a therapeutic payload, to the site of the pathogenic cells. In some embodiments, the effector structure can modulate expression of a target gene. In some embodiments, the effector structure can regulate enzyme activity, gene/protein expression, molecular signaling, and molecular interactions.

An effector structure is a product of a combination of reactive effector moieties that produces a desired activity in a sample. The active effector structure can possess a targeted activity or an elevated level of activity as compared to either or both of the reactive effector moieties individually. In some embodiments, the active effector structure can possess a new or substantially different activity than the individual reactive effector moieties, as compared to either or both of the reactive effector moieties individually.

A diverse array of effector structures may be produced by nucleic acid templated assembly. Any active product may serve as an effector structure as long as such a structure can be produced by the templated assembly by the reaction of corresponding reactive effector moieties. Thus, any compound that may be reconstituted from separate portions (e.g., reactive effector moieties) by formation of an amide bond, triazole linkage, phosphine oxide linkage, or other bio-orthogonal ligation products, as described herein, may serve as an active effector structure. In addition, such compounds can be assembled on virtually any accessible target nucleic acid molecule template, thus allowing assembly in a very diverse set of samples.

General forms of effector structures include but are not limited to: Amide-linked Effector Structure created by a non-traceless bio-orthogonal reaction, such as:

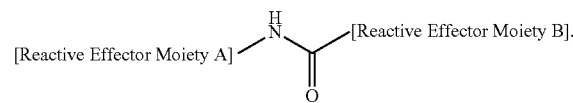

Triazole-linked effector structure produced by an azide-alkyne bio-orthogonal reaction, such as:

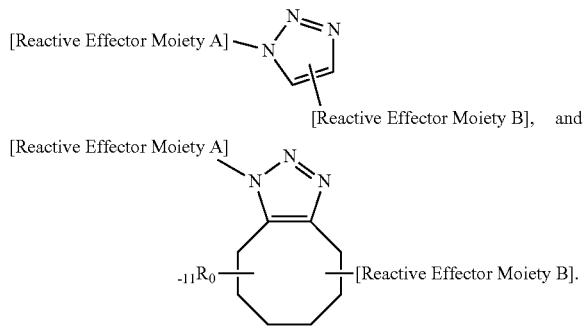

Phosphine oxide-linked effector structures produced by non-traceless Staudinger ligation bio-orthogonal reactions, such as:

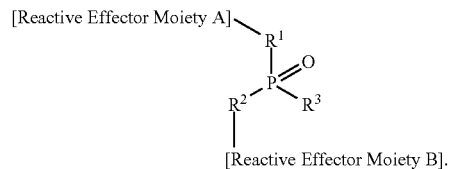

Active effector structures can also include proteins, peptides containing standard or non-standard amino acids, peptidomimetic structures, and drugs or other bioactive compounds.

In some embodiments, effector structures may be liberated from the other moieties in the templated assembly product by cleavage of the bonds connecting the effector structure to the remainder of the product. Cleavage may be achieved by, for example, hydrolysis of the connecting bonds, or by enzymatic cleavage by proteins or other compounds endogenous to the sample. Examples of these cleavable bonds include, but are not limited to, esters, thioesters, imines, hydrazones, cleavage motifs of cellular proteases, or substrates of cellular enzymes. Cleavable groups may be introduced by their incorporation into a haplomer moiety, linker, or accessory group during synthesis, or may be generated during the ligation reaction. In some embodiments, post-ligation cleavage or other in situ chemical modification of the effector structure may be required for the effector structure to trigger a desired activity.

An effector structure may also trigger activity by acting within a target compartment (for example, within a cell), at the surface of a target compartment (for example, at the cell surface), in the vicinity of the target compartment (for example, when the effector structure is actively exported from the cell, leaks from the cell, or released upon cell death), or diffuse or be carried to a distant region of the sample to trigger a response. In some embodiments, effector structures can be targeted to their active sites by incorporation of targeting groups in the templated assembly product. Examples of targeting groups include, but are not limited to, endoplasmic reticulum transport signals, golgi apparatus transport signals, nuclear transport signals, mitochondrial transport signals, ubiquitination motifs, other proteosome targeting motifs, or glycosylphosphatidylinositol anchor motifs. Targeting groups may be introduced by their incorporation into a haplomer moiety, chemical linker, or accessory group during synthesis, or may be generated during the ligation reaction.

In some embodiments, the effector structure can be presented on the surface of a target compartment. In some embodiments, the effector structure can be presented on the surface of a cell as a ligand bound to a major histocompatibility complex molecule.

In some embodiments, the effectors can be endogenous peptides, and their analogue, or completely synthetic structures which are targets for effector structure-triggered agents such as antibodies. Because the availability of target nucleic acid molecules can limit production of active effectors, it may be desirable to have effector structures that exert activity when present at low levels.

In some embodiments, killing or growth inhibition of target cells can be induced by direct interaction with cytotoxic, microbicidal, or virucidal effector structures. Numerous toxic molecules known in the art can be produced. In some embodiments, traceless bio-orthogonal reactive chemistry may produce toxic peptides. Examples of toxic peptides include, but are not limited to, bee melittin, conotoxins, cathelicidins, defensins, protegrins, and NK-lysin.

In some embodiments, killing or growth inhibition of target cells can be induced by pro-apoptotic effector structures. For example, effector peptides produced using traceless bio-orthogonal chemistry include pro-apoptotic peptides, including but not limited to, prion protein fragment 106-126 (PrP 106-126), Bax-derived minimum poropeptides associated with the caspase cascade including Bax 106-134, and pro-apoptotic peptide (KLAKLAK)$_2$.

In some embodiments, the effector molecule produced can be thrombogenic, in that it induces activation of various components of the clotting cascade of proteins, or activation of proteins, or activation and/or aggregation of platelets, or endothelial damage that can lead to a biologically active process in which a region containing pathogenic cells can be selectively thrombosed to limit the blood supply to a tumor or other pathogenic cell. These types of effectors can also induce clotting, or prevent clotting, or prevent platelet activation and aggregation in and around targeted pathogenic cells.

In some embodiments, effector structures can mediate killing or growth inhibition of target cells or viruses by activating molecules, pathways, or cells associated with the immune system. Effector structures may engage the innate immune system, the adaptive immune system, and/or both.

In some embodiments, effector structures can mediate killing or growth inhibition of cells or viruses by stimulation of the innate immune system. In some embodiments, effector structures can include pathogen-associated molecular patterns (PAMPs), damage-associated molecular patterns (DAMPs), and synthetic analogues thereof.

In some embodiments, the innate immune system can be engaged by effector structures that activate the complement system. A non-limiting example of a complement activating effector structures can be the C3a fragment of complement protein C3.

In some embodiments, effector structures can be agonists of formylated peptide receptors. In some embodiments, the formylated tripeptide formyl-Met-Leu-Phe can be produced using traceless bio-orthogonal chemistry. A specific example scheme for generating fMLF peptides using traceless haplomers can include:

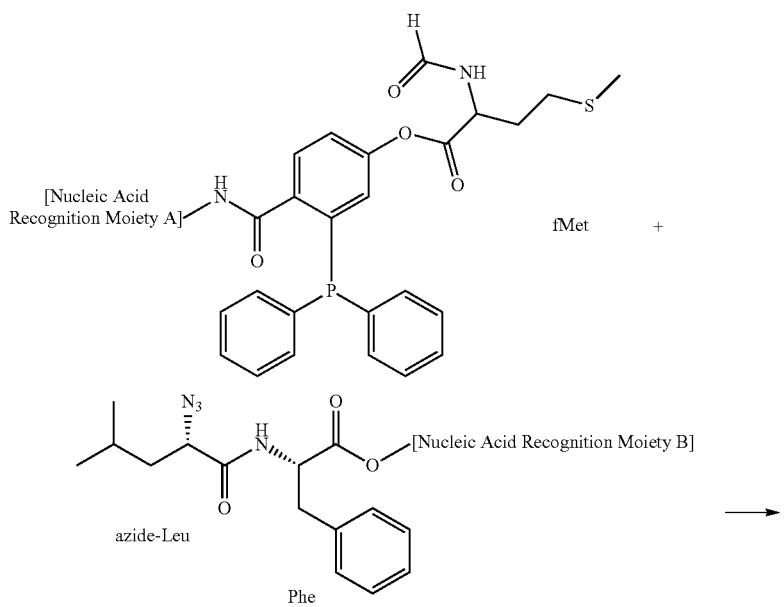

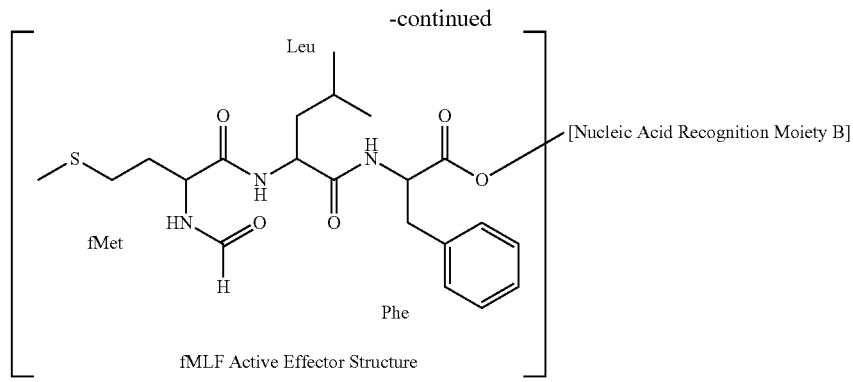

In some embodiments, small peptide agonists of the formylated peptide receptor such as the peptide Trp-Lys-Tyr-Met-Val-(D-Met) (SEQ ID NO:24) can be produced.

In some embodiments, effector structures with natural or synthetic ligands of Toll-Like Receptors (TLR) can be produced. In a non-limiting example, an effector structure can include peptide fragments of heat shock proteins (hsp) known to be TLR agonists.

In some embodiments, traceless bio-orthogonal chemistry may be used to produce the muramyl dipeptide agonist of the NOD2 receptor to activate an inflammatory response.

In some embodiments, effector structures can mediate killing or growth inhibition of cells or viruses by activating molecules or cells of the adaptive immune system. Unique to the adaptive immune system, molecules or cells can be engineered to recognize an extraordinary variety of structures, thus removing the constraint that the effector structure must be intrinsically active or bind to an endogenous protein.

Because of the modularity of the present system, a single engineered molecule or cell of the adaptive immune system can be utilized for therapy of any target compartments or target nucleic acids, since the same effector structure can be produced in the presence of any target nucleic acid molecule. This is an advantage over the current state of the art, where new molecules or cells must be engineered to treat any new target, involving significant time, difficulty, and cost.

In some embodiments, an effector structure can be a ligand for an antibody or antibody fragment (including but not limited to Fab, Fv, and scFv). Traceless bio-orthogonal approaches can be used to produce a peptide or other epitope that is bound by an existing antibody, or an antibody can be developed to recognize an effector structure created by any selectively reactive or bio-orthogonal approach.

For therapeutic intervention in conjunction with haplomers, manufactured antibodies can be administered as effector structure-triggered agents. The agent may be administered to a sample before, during, or after administration of haplomers. An example includes, but is not limited to, reporter antibodies. In some embodiments, unmodified antibodies can be utilized to mediate therapeutic effects. In some embodiments, an effector structure specific antibody can be manufactured with a payload attached designed to enhance the therapeutic effect. Examples of therapeutic antibody payloads include, but are not limited to, cytotoxins, radioisotopes, radiosensitizers used in conjunction with radiation therapy, enzymes for the conversion of a co-administered prodrug to an active drug, or any other antibody-directed therapy.

In some embodiments, an antibody may be used for detection of an effector structure in vivo, thus localizing a target compartment within a subject.

In some embodiments, effector structures can activate T-cells. Activation of T-cells can be achieved by an effector structure binding to a T-cell receptor (TCR). In some embodiments, an effector structure can be presented on the surface of a target cell bound to an MHC molecule, facilitating binding of a T-cell receptor. An effector structure may be bound by MHC class I or MHC class II molecules. In an exemplary embodiment, an effector structure is bound by MHC class I molecules. The structure that binds to the TCR can be a conventional peptide antigen, or a superantigen that binds to a broad subset of T cells that express a particular variable (V) region. As opposed to a TCR that is selected to interact with specific antigen, a superantigen can activate a large number of T cell populations that have receptors capable of binding to different antigen-MHC complexes, and induce a strong inflammatory response to set off a cascade of inflammatory mediators. Thus, a superantigen or superantigen mimetic can be produced as an active effector structure that can recruit large numbers of T cells to a pathogenic cell, and lead to destruction or limitation in the growth of such cells.

Natural ligands bound to MHC class I molecules are typically peptides of 8 to 10 amino acids in length, though other lengths are permissible. Natural ligands bound to MHC class II molecules are typically peptides of 15 to 24 amino acids in length, though other lengths are permissible. Effector structures can be produced using traceless bio-orthogonal chemistry. A peptide that is a known MHC ligand can be utilized as an effector structure, or a novel peptide can be produced. Assays for evaluating binding of peptides to MHC molecules are known in the art, and may be used to evaluate candidate effector structures for MHC binding.

MHC molecules are also known to bind non-peptide structures and peptidomimetics. Non-traceless bio-orthogonal templated assembly approaches may be utilized to create peptidomimetic MHC-binding antigens for activation of T-cell receptors. In some embodiments, the peptidomimetic can be a peptide of 6 to 40 amino acids or non-standard amino acids, where between 1 to 4 residues are replaced by a non-traceless bio-orthogonal ligation structure, such as:

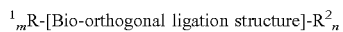

where $R^1$ and $R^2$ are covalently bonded standard or non-standard amino acids, m=0 to 40, n=0 to 40, and m+n=2 to 39. In some embodiments, m+n=3 to 11, producing structures suitable for binding to MHC class I molecules.

Examples of effector structures using the MART-1 immunodominant tumor associated antigen as a design scaffold include, but are not limited to:

An example of peptidomimetic effector structure based on Staudinger ligation chemistry is:

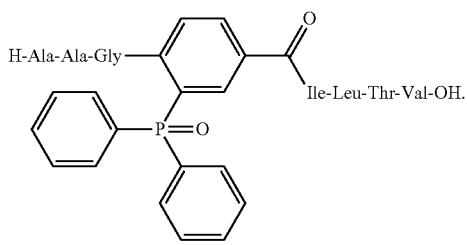

An example of peptidomimetic effector structure based on azide-alkyne ligation chemistry is:

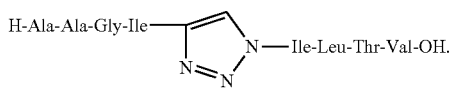

Example of peptidomimetic effector structure based on azide-cyclooctyl alkyne ligation chemistry is:

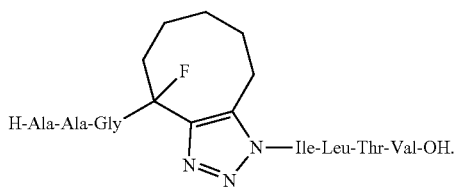

Peptidomimetic effector structures may be designed based on a natural ligand known to bind MHC molecules and activate a T-cell receptor (as in the examples above.) Alternately, the peptidomimetic effector structure may be an entirely new structure, and a new T-cell clone or antibody-TCR chimera (T-body) may be developed for use as an effector structure-triggered agent. This approach offers the benefit of using highly non-self, non-cross-reactive effector structures which may increase activity while reducing undesired side-effects during therapy.

In some embodiments, natural peptide or peptidomimetic MHC-binding effector structures can be utilized in conjunction with adoptive T-cell therapy, where the adoptive T-cell serves as an effector structure-triggered agent. An adoptive T cell therapy provides a patient with exogenous T cells which can accomplish a therapeutically desirable immunoreaction. However, allogenic T cells can be potentially problematic either from host rejection, or the risk of graft-vs.-host disease.

Recently developed techniques have enabled the use of autologous T cells for various therapeutic applications, where host genetic incompatibility is avoided. Clinically relevant T cell subsets (including clonally-derived cells with specific TCRs) can be expanded in vitro and returned to autologous patients. Greater selectivity can be achieved by means of autologous T cells transfected in vitro with vectors enabling the expression of TCRs of known specificity against target antigens (such as those known to be expressed on tumors), or engineered chimeric antigen receptors with equivalent desired specificities.

Once an active effector structure has been selected, appropriate selectively-reactive moieties and reactive effector moieties can be designed for incorporation into the haplomer(s). These moieties are designed such that they can reconstitute the active effector moiety when a templated assembly reaction occurs.

In some embodiments, the reactive effector moiety further comprises a bio-orthogonal reactive molecule. In some embodiments, the bio-orthogonal reactive molecule is selected from the group consisting of an azide, an alkyne, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, and a quadricyclane, or any derivative thereof. In some embodiments, the reactive effector moiety of the second nucleic acid molecule is linked to a bio-orthogonal reactive molecule, and the reactive effector moiety of the first nucleic acid molecule is linked to a bio-orthogonal reactive molecule, wherein the bio-orthogonal reactive molecule of the second nucleic acid molecule can chemically interact with the bio-orthogonal reactive molecule of the first nucleic acid molecule. In some embodiments, the bio-orthogonal reactive molecule of the first nucleic acid molecule is hexynyl and the bio-orthogonal reactive molecule of the second nucleic acid molecule is azide. In some embodiments, the bio-orthogonal reactive molecule of the first nucleic acid molecule is azide and the bio-orthogonal reactive molecule of the second nucleic acid molecule is hexynyl.

An example of selectively-reactive moiety can include a bio-orthogonal reactive moiety. The bio-orthogonal reactive moiety includes those groups that can undergo "click" reactions between azides and alkynes, traceless or non-traceless Staudinger reactions between azides and phosphines, and native chemical ligation reactions between thioesters and thiols. Additionally, the bio-orthogonal moiety can be any of an azide, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, a quadricyclane, and derivatives thereof. Selectively reactive moieties of members of a set of corresponding haplomers are selected such that they will react with each other to produce an active effector structure.

Multiple selectively-reactive moieties can be used with the methods and compositions disclosed herein, some non-limiting examples include:

Azide-Alkyne "Click Chemistry"

Click chemistry is highly selective as neither azides nor alkynes react with common biomolecules under typical conditions. Azides of the form $R-N_3$ and terminal alkynes of the form $R-C\equiv CH$ or internal alkynes of the form $R-C\equiv C-R$ react readily with each other to produce Huisgen cycloaddition products in the form of 1,2,3-triazoles.

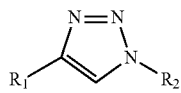

Azide-based haplomers have the substructure: $R-N_3$, where R is a chemical linker, nucleic acid recognition moiety (e.g. a portion of an oligonucleotide that is complementary to another portion of a nucleic acid molecule), or reactive effector moiety. Azides and azide derivatives may be readily prepared from commercially available reagents.

Azides can also be introduced to a reactive effector moiety during synthesis of the reactive effector moiety. In some embodiments, an azide group is introduced into a reactive effector moiety comprised of a peptide by incorporation of a commercially available azide-derivatized standard amino acid or amino acid analogue during synthesis of the reactive effector moiety peptide using standard peptide synthesis methods Amino acids may be derivatized with an azide replacing the α-amino group, affording a structure of the form:

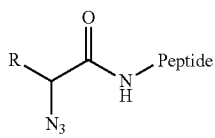

where R is a side chain of a standard amino acid or non-standard amino acid analogue.

Commercially available products can introduce azide functionality as amino acid side chains, resulting in a structure of the form:

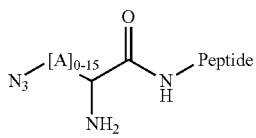

where A is any atom and its substituents in a side chain of a standard amino acid or non-standard amino acid analogue.

An azide may also be introduced into a reactive effector moiety peptide after synthesis by conversion of an amine group on the peptide to an azide by diazotransfer methods. Bioconjugate chemistry can also be used to join commercially available derivatized azides to chemical linkers, nucleic acid recognition moieties, or reactive effector moieties that contain suitable reactive groups.

Standard alkynes can be incorporated into a haplomer by methods similar to azide incorporation. Alkyne-functionalized nucleotide analogues are commercially available, allowing alkyne groups to be directly incorporated at the time of nucleic acid recognition moiety synthesis. Similarly, alkyne-deriviatized amino acid analogues may be incorporated into a reactive effector moiety by standard peptide synthesis methods. Additionally, diverse functionalized alkynes compatible with bioconjugate chemistry approaches may be used to facilitate the incorporation of alkynes to other moieties through suitable functional or side groups.

Azide-Activated Alkyne "Click Chemistry"

Standard azide-alkyne chemistry reactions typically require a catalyst, such as copper(I). Since copper(I) at catalytic concentrations is toxic to many biological systems, standard azide-alkyne chemistry reactions have limited uses in living cells. Copper-free click chemistry systems based on activated alkynes circumvent toxic catalysts.

Activated alkynes often take the form of cyclooctynes, where incorporation into the cyclooctyl group introduces ring strain to the alkyne.

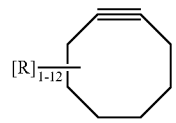

Heteroatoms or substituents may be introduced at various locations in the cyclooctyl ring, which may alter the reactivity of the alkyne or afford other alternative chemical properties in the compound. Various locations on the ring may also serve as attachment points for linking the cyclooctyne to a nucleic acid templated assembly moiety or linker. These locations on the ring or its substituents may optionally be further derivatized with accessory groups.

Multiple cyclooctynes are commercially available, including several derivatized versions suitable for use with standard bioconjugation chemistry protocols. Commercially available cyclooctyne derivatized nucleotides can aid in facilitating convenient incorporation of the reactive effector moiety during nucleic acid recognition moiety synthesis.

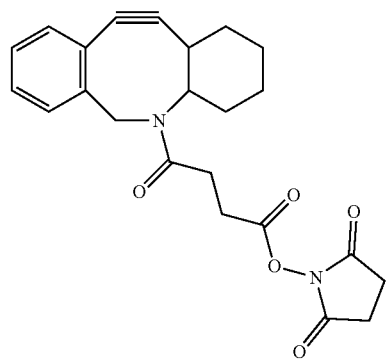 [SMILES: O=C(CCC(=O)N1Cc2ccccc2C#CC2CCCCC21)ON1C(=O)CCC1=O]

Cyclooctyne-azide based bio-orthogonal chemistry may produce templated assembly products of the general structure:

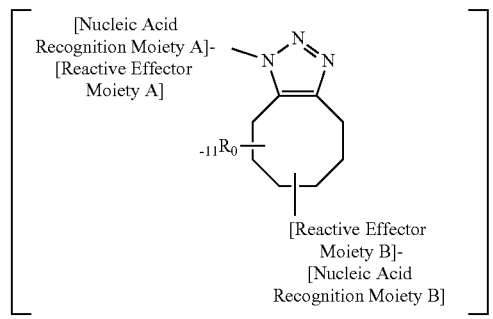

Effector Structure

Another example:

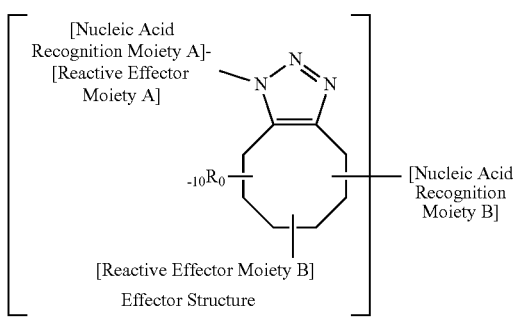

Azide-Phosphine Staudinger Chemistry

The Staudinger reduction, based on the rapid reaction between an azide and a phosphine or phosphite with loss of $N_2$, also represents a bio-orthogonal reaction. The Staudinger ligation, in which covalent links are formed between the reactants in a Staudinger reaction, is suited for use in nucleic acid templated assembly. Both non-traceless and traceless forms of the Staudinger ligation allow for a diversity of options in the chemical structure of products formed in these reactions.

Non-Traceless Staudinger Ligation

The standard Staudinger ligation is a non-traceless reaction between an azide and a phenyl-substituted phosphine such as triphenylphosphine, where an electrophilic trap substituent on the phosphine, such as a methyl ester, rearranges with the aza-ylide intermediate of the reaction to produce a ligation product linked by a phosphine oxide. An example of a Staudinger ligation product formed by haplomers A and B may have the structure:

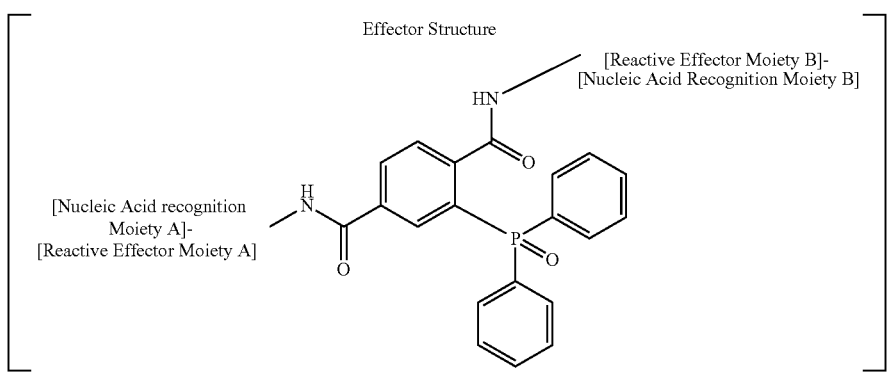

Phenyl-substituted phosphines carrying electrophilic traps can also be readily synthesized. Derivatized versions are available commercially and suitable for incorporation into haplomers:

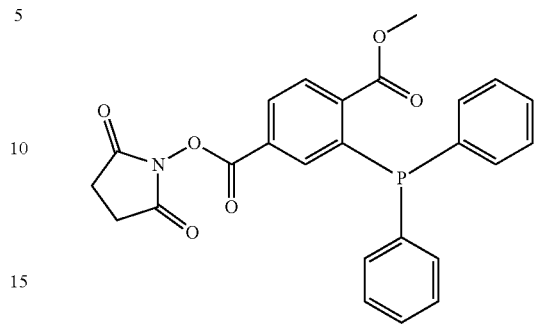

Traceless Staudinger Ligation

In some embodiments, phosphines capable of traceless Staudinger ligations may be utilized as reactive effector moieties. In a traceless reaction, the phosphine serves as a leaving group during rearrangement of the aza-ylide intermediate, creating a ligation typically in the form of a native amide bond. Compounds capable of traceless Staudinger ligation generally take the form of a thioester derivatized phosphine or an ester derivatized phosphine:

An exemplary ester-derivatized phosphine for traceless Staudinger ligation is:

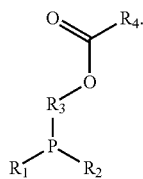

An exemplary thioester-derivatized phosphine for traceless Staudinger ligations is:

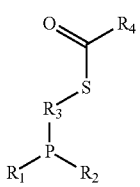

Chemical linkers or accessory groups may optionally be appended as substituents to the R groups in the above structures, providing attachment points for nucleic acid recognition moieties or for the introduction of additional functionality to the reactant.

Traceless Phosphinophenol Staudinger Ligation

Compared to the non-traceless Staudinger phenylphosphine compounds, the orientation of the electrophilic trap ester on a traceless phosphinophenol is reversed relative to the phenyl group. This enables traceless Staudinger ligations to occur in reactions with azides, generating a native amide bond in the product without inclusion of the phosphine oxide.

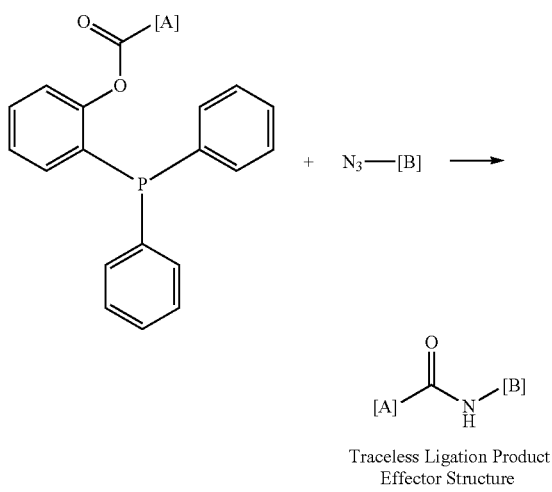

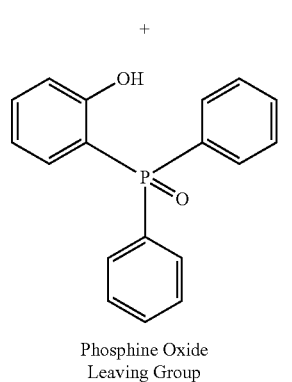

Phosphine Oxide
Leaving Group

The traceless Staudinger ligation may be performed in aqueous media without organic co-solvents if suitable hydrophilic groups, such as tertiary amines, are appended to the phenylphosphine. Weisbrod and Marx describe preparation of water-soluble phosphinophenol, which may be loaded with a desired reactive effector moiety containing a carboxylic acid (such as the C-terminus of a peptide) via the mild Steglich esterification using a carbodiimide such as dicyclohexylcarbodiimide (DCC) or N,N'-diisopropylcarbodiimide (DIC) and an ester-activating agent such as 1-hydroxybenzotriazole (HOBT) (Synlett, 2010, 5, 787-789). This approach facilitates synthesis of haplomers of the form:

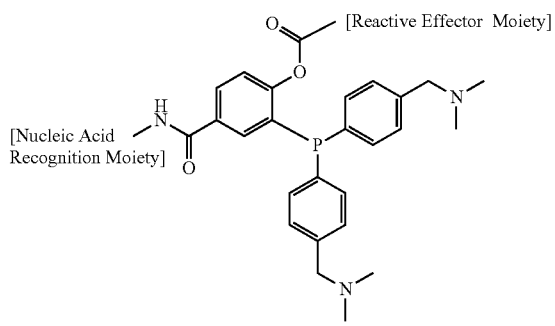

Water-soluble phosphinophenol-based traceless haplomer structure.

Traceless Phosphinomethanethiol Staudinger Ligation

Phosphinomethanethiols represent an alternative to phosphinophenols for mediating traceless Staudinger ligation reactions. In general, phosphinomethanethiols possess favorable reaction kinetics compared with phosphinophenols in mediating traceless Staudinger reaction. U.S. patent application 2010/0048866 and an article to Tam et al. describe preparation of water-soluble phosphinomethanethiols of the form:

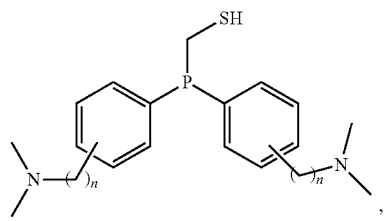

(J. Am. Chem. Soc., 2007, 129, 11421-30).

These compounds may be loaded with a peptide or other payload, in the form of an activated ester, to form a thioester suitable for use as a traceless bio-orthogonal reactive group:

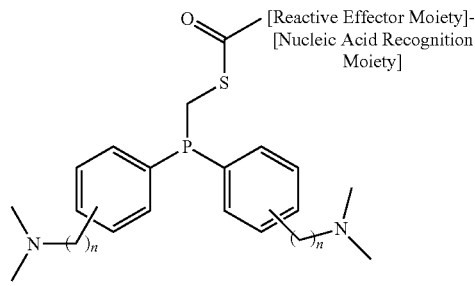

Haplomer structure based on water-soluble phosphinomethanethiol traceless Staudinger bio-orthogonal chemistry.

Native Chemical Ligation

Native chemical ligation is a bio-orthogonal approach based on the reaction between a thioester and a compound bearing a thiol and an amine. The classic native chemical ligation is between a peptide bearing a C-terminal thioester and another bearing an N-terminal cysteine, as seen below:

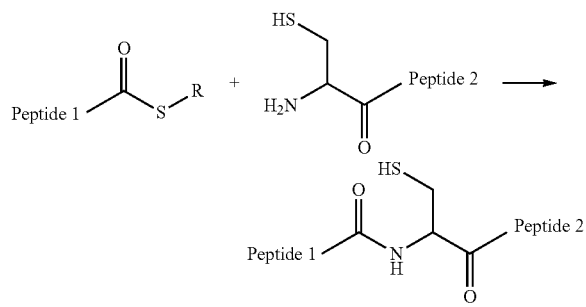

Native chemical ligation may be utilized to mediate traceless reactions producing a peptide or peptidomimetic containing an internal cysteine residue, or other thiol-containing residue if non-standard amino acids are utilized.

N-terminal cysteines may be incorporated by standard amino acid synthesis methods. Terminal thioesters may be generated by several methods known in the art, including condensation of activated esters with thiols using agents such as dicyclohexylcarbodiimide (DCC), or introduction during peptide synthesis via the use of "Safety-Catch" support resins.

Other Selectively Reactive Moieties

Any suitable bio-orthogonal reaction chemistry may be utilized for synthesis of haplomers, as long as it efficiently mediates a reaction in a highly selective manner in complex biologic environments. A recently developed non-limiting example of an alternative bio-orthogonal chemistry that may be suitable is reaction between tetrazine and various alkenes such as norbornene and trans-cyclooctene, which efficiently mediates bio-orthogonal reactions in aqueous media.

Chemical linkers or accessory groups may optionally be appended as substituents to the above structures, providing attachment points for nucleic acid recognition moieties or reactive effector moieties, or for the introduction of additional functionality to the reactant.

The configurations involving the reactive effector moieties depicted in the Examples and Figures could be reversed. In other words, the reactive effector moiety could be linked to the 3' end of the first haplomer bottle, as long as the second haplomer accordingly had its reactive effector moiety linked to its 5' end. The Examples provided below have the first haplomer bottles with a 5'-linked reactive effector moiety, and the second haplomers with a 3'-lined reactive effector moiety. Likewise, in this system the reactive effector moieties can be switched around. For example, instead of using the first haplomer bottle with a 5'-hexynyl and the second haplomer with a 3'-azide (as in the provided Examples), the first haplomer bottle could bear the azide, and the second haplomer the hexynyl group.

In some embodiments, the portion of the first nucleic acid molecule that is not linked to a reactive effector moiety can have additional nucleotide bases that overhang and do not form a part of the stem structure. In some embodiments, the end of the second nucleic acid molecule that is not linked to a reactive effector moiety can have additional nucleotide bases that overhang and do not form a complementary part of the structure with the stem portion of the first nucleic acid molecule. In addition, in some embodiments, the portion of the stem that is linked to the reactive effector moiety can also have nucleotide bases that are not base paired with the first stem portion. Such an extension of the stem with a non-hybridized "arm" places the two reactive effectors at a greater spatial distance, thus, tending to reduce their mutual reactivity. So, for a few nucleotide bases (less than 10 or less than 5), enforced reactivity is still likely to occur, but will tend to diminish as the non-base paired segment grows in length.

In some embodiments, added nucleotide bases can be of indefinite length, as long as they did not: 1) have significant homologies with any of the other regions of the locked TAPER oligonucleotides, and thus tend to cross-hybridize and interfere; or 2) interfere non-specifically with any other features of the system. For example, a long appended sequence might reduce transformation efficiencies of locked TAPER oligonucleotides used in a therapeutic context. Also, appended sequences should be designed to avoid spurious hybridizations with other cellular transcripts. Appended non-homologous sequences of 20-30 nucleotide bases are suitable. The appended nucleic acid sequences may contain primer sequences commonly used in the art. Such examples may include, but are not limited to, M13, T3, T7, SP6, VF2, VR, modified versions thereof, complementary sequences thereof, and reverse sequences thereof. In addition, custom primer sequences are also included. Such primer sequences can be used, for example, the possible application of chemically-ligated oligonucleotides spatially elicited (CLOSE) to the locked TAPER strategy, (see, PCT Publication WO 2016/89958; which is incorporated herein by reference in its entirety).

The reactive effector moiety can also be conjugated to other moieties on a haplomer such that the effector structure produced may be cleaved from the templated assembly ligation product after the reaction has occurred. Cleavage may occur via hydrolysis of a bond, or be catalyzed by enzymes or other molecules within a cell. Non-limiting examples of cleavage linkages include: esters, thioesters, imines, hydrazones, cleavage motifs of cellular proteases, or substrates of cellular enzymes.

In embodiments in which a traceless bio-orthogonal reactive group forms a native amide bond in the effector structure, the reactive effector moiety may include a non-active portion of an active peptide, or a non-active portion of a non-peptide drug or endogenous bioactive compound that can be reconstituted via an amide bond to a corresponding portion.

In embodiments in which a non-traceless bio-orthogonal reactive group incorporates a phosphine oxide, triazole, or other bio-orthogonal ligation residue, reactive effector moieties may include a non-active portion of a peptidomimetic structure or non-active portion of a drug or other bioactive compound. In these embodiments, the ligated residue from the bio-orthogonal reaction can be integrated into the effector structure.

Due to the diverse nature of reactive effector moieties, various methods may be necessary for synthesis. In some embodiments, peptides are used, and reactive effector moieties may be synthesized using standard Merrifield solid-phase synthesis. Synthesis approaches for other reactive effector moieties are dictated by the specific chemical structure of the particular moiety.

The present disclosure also provides kits. In some embodiments, the kit comprises any one or more of the first nucleic acid molecules described herein. In some embodiments, the kit comprises any one or more of the second nucleic acid molecules described herein.

The present disclosure also provides methods of producing a templated assembly product for a cell comprising: a)

contacting a target nucleic acid molecule of the cell with a first nucleic acid molecule described herein; and contacting the first nucleic acid molecule with a second nucleic acid molecule, wherein the second nucleic acid molecule comprises: i) a nucleotide portion that is substantially complementary to the stem portion of the first nucleic acid molecule that is linked to the reactive effector moiety; and ii) a reactive effector moiety which can chemically interact with the reactive effector molecule of the first nucleic acid molecule; wherein the $T_m$ of the second nucleic acid molecule:first or second stem portion linked to the reactive effector moiety is less than or equal to the $T_m$ of the first stem portion:second stem portion, thereby resulting in the combination of the respective reactive effector moieties thereby producing the templated assembly product.

In some embodiments, the first nucleic acid molecule comprises the nucleotide sequence of SEQ ID NO:13, and the second nucleic acid molecule comprises the nucleotide sequence of SEQ ID NO:15; or the first nucleic acid molecule comprises the nucleotide sequence of SEQ ID NO:14, and the second nucleic acid molecule comprises the nucleotide sequence of SEQ ID NO:16. In some embodiments, the bio-orthogonal reactive molecule of the first nucleic acid molecule is hexynyl and the bio-orthogonal reactive molecule of the second nucleic acid molecule is azide. In some embodiments, the bio-orthogonal reactive molecule of the first nucleic acid molecule is azide and the bio-orthogonal reactive molecule of the second nucleic acid molecule is hexynyl.

Administration of sets of corresponding haplomers may vary according to the nature of the sample. In some embodiments, the haplomers can be dispensed into a sample within a suitable vessel or chamber. In some embodiments, the sample may be dispensed into a vessel already containing the haplomers. In some embodiments, the haplomers can be assembled in in vitro or in situ.

In some embodiments, the haplomers can be administered for templated assembly in vivo. To facilitate administration of the haplomers to samples, prepared haplomers may be administered in any suitable buffer or formulation, optionally incorporating a suitable delivery agent, and contacted with the sample. Concentrated forms of a haplomer may be handled separate from its counterpart haplomer, as product-generating reactions may occur in the absence of target nucleic acid molecule template at high concentrations. Table 1 provides guidelines for maximum acceptable concentrations of gymnotic (no delivery agent) haplomers comprised of various reactive effector moieties. If the haplomers are contacted at concentrations above these thresholds, non-templated background reactions may occur.

TABLE 1

Maximum concentrations for contact of haplomers, above which non-templated reaction levels may occur

| Bioorthogonal Reactive Chemistry | Maximum Concentration |
| --- | --- |
| Azide-Alkyne | <50 µM |
| Azide-Phosphine | <50 µM |
| Native Chemical Ligation | <1 mM |

Threshold concentrations of other haplomers may be determined empirically utilizing the templated assembly diagnostic evaluation assay disclosed.

In some embodiments, the likelihood of non-templated reactions may be reduced by administering a set of corresponding haplomers such that one haplomer is administered first, then a time delay is observed before the corresponding haplomer is administered. This time delay may range from one minute to days, depending on the persistence of the haplomers in the system.

Certain delivery agents, such as transfection reagents such as cationic lipids, polyethyleneimine, dextran-based transfectants, or others known in the art, may cause condensation of the haplomers. Under these circumstances, haplomers may be prepared separate from the corresponding reactive haplomers and administered to the sample separately. Haplomers may also be administered gymnotically, dissolved in an appropriate buffer without addition of any additional delivery agent.

The haplomers may also be administered after formulation with a suitable delivery agent. A suitable delivery agent may enhance the stability, bioavailability, biodistribution, cell permeability, or other desirable pharmacologic property of the haplomers, or a combination of these properties. Delivery agents known in the art include, but are not limited to, polycationic transfection reagents, polyethyleneimine and its derivatives, DEAE-Dextran, other transfection reagents, salts, ions, buffers, solubilization agents, various viral vectors, liposomes, targeted liposomes, nanoparticles, carrier polymers, endosome disruptors, permeabilization agents, lipids, steroids, surfactants, dispersants, stabilizers, or any combination thereof.

Delivery of haplomers to target compartments may also be enhanced by covalent attachment of accessory groups to haplomers. Accessory groups that may enhance delivery may include compounds known to enhance the stability and biodistribution of compounds, such as polyethylene glycol (PEG); and enhance cell permeability of haplomers, including, but not limited to, cholesterol derivatives known in the art, endosome-disrupting agents known in the art, and cell-penetrating peptides, such as poly-cations such as poly-arginine or polylysine, peptides derived from the HIV tat protein, transportan, and peptides derived from the antennapedia protein (penetratin).

Administration of effector product-triggered agents, such as an antibody or other effector product-detecting molecule, or effector product-detecting cell, may also be included. The administration can be part of the templated assembly procedure. It may be administered before, during, or after administration of the haplomers, and by any method appropriate to the agent. In some embodiments, the effector structure-triggered agent is administered prior to administration of the haplomers to facilitate triggering of activity by effector structures as soon as they are formed and available for agent binding.

In some embodiments, multiple sets of corresponding haplomers may be administered in parallel. These sets of reactants may bind to multiple hybridization sites on a single target nucleic acid, or bind to different target nucleic acids, or a combination thereof. The different sets of haplomers may produce the same effector structure, thus increasing the level of activity generated by that effector structure by boosting its production, or the different sets of haplomers may produce different effector structures, thus producing multivalent activity in the sample, or a combination thereof. When multiple sets of haplomers are administered in parallel, reactive effector moieties from different sets of haplomers that have the same bio-orthogonal reactive group (or groups that do not react with each other, if different bio-orthogonal chemistries are employed for different sets of haplomers) may be administered together, even at high concentrations, since they will not be reactive with each other. For example, if an azide-alkyne bio-orthogonal reactive system is employed for each set of corresponding haplomers, all of the azide-containing haplomers may be formulated and administered together, and all of the alkyne-containing haplomers may be formulated and administered together after sufficient dilution of the azides in the sample.

In some embodiments, the composition administered can include two or more reactive effector moieties that are each linked to bio-orthogonal reactive molecules, to produce two or more active effector structures. Production of two or more active effector structures can yield two or more effector activities, such as inducing an immune response, programmed cell death, apoptosis, necrosis, lysis, growth inhibition, inhibition of viral infection, inhibition of viral replication, inhibition of oncogene expression, modification of gene expression, inhibition of microbial infection, and inhibition of microbe replication, as well as combinations of these biological activities.

In some embodiments, the composition administered can include two or more sets of corresponding haplomers that include anti-target loop portions capable of binding two or more target nucleic acid molecules. Two or more target nucleic acid molecules may be found within the same gene transcript, or alternatively on distinct and separate transcripts. Two or more sets of corresponding haplomers recognizing distinct nucleic acid target molecules within the same cellular transcript may independently carry the same or distinct reactive effector moieties that react to form additional copies of the same effector products in a template-directed manner. The inclusion of two or more reactive effector moieties can produce two or more active effector structures to yield two or more effector activities, such as inducing an immune response, programmed cell death, apoptosis, non-specific or programmed necrosis, lysis, growth inhibition, inhibition of viral infection, inhibition of viral replication, inhibition of oncogene expression, modification of gene expression, inhibition of microbial infection, and inhibition of microbe replication, as well as combinations of these biological activities.

The abundance of target nucleic acid molecules may also limit the amount of active effector structure produced by templated assembly. In some embodiments, there is an average of at least 5 copies of target nucleic acid molecules per target compartment. The dosage and concentration of the composition administered can take the availability of the target nucleic acid molecules into account.

In some embodiments, methods of delivering a haplomer or haplomers or a composition comprising one or more haplomers to a pathogenic cell is disclosed. The methods can include administering a therapeutically effective amount of a set or multiple sets of corresponding haplomer compositions to the pathogenic cell, binding the haplomer compositions to a target nucleic acid molecule, and generating active effector products. The composition can include any one or more of the first and/or second nucleic acid molecules described herein. In some embodiments, the methods can also include detecting the presence or absence of the target nucleic acid molecule prior to administering the haplomer composition.

Pharmaceutical compositions may be administered by one of the following routes: oral, topical, systemic (e.g. transdermal, intranasal, or by suppository), or parenteral (e.g. intramuscular, subcutaneous, or intravenous injection). Compositions may take the form of tablets, pills, capsules, semisolids, powders, sustained release formulations, solutions, suspensions, elixirs, aerosols, or any other appropriate compositions; and comprise at least one compound in combination with at least one pharmaceutically acceptable excipient. Suitable excipients are well known to persons of ordinary skill in the art, and they, and the methods of formulating the compositions, may be found in such standard references as Remington: The Science and Practice of Pharmacy, A. Gennaro, ed., 20th edition, Lippincott, Williams & Wilkins, Philadelphia, Pa. Suitable liquid carriers, especially for injectable solutions, include water, aqueous saline solution, aqueous dextrose solution, and glycols.

Pharmaceutical compositions suitable for injection may include sterile aqueous solutions (where water soluble) or dispersions and sterile powders for the extemporaneous preparation of sterile injectable solutions or dispersion. In all cases, the composition should be sterile and should be fluid to the extent that easy syringeability exists. The composition should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents. In many cases, isotonic agents can be included, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the composition containing the haplomers in a suitable amount in an appropriate solvent with one or a combination of ingredients enumerated above. Generally, dispersions are prepared by incorporating the composition into a sterile vehicle which contains a basic dispersion medium and the required other ingredients from those enumerated above When the composition containing the haplomers is suitably protected, as described above, the composition can be formulated for oral administration, for example, with an inert diluent or an assimilable edible carrier. The composition and other ingredients can also be enclosed in a hard or soft shell gelatin capsule, compressed into tablets, or incorporated directly into the subject's diet. For oral therapeutic administration, the composition can be incorporated with excipients and used in the form of ingestible tablets, buccal tablets, troches, capsules, elixirs, suspensions, syrups, wafers, and the like. The percentage of the compositions and preparations can, of course, be varied. The amount of haplomers in such therapeutically useful compositions is such that a suitable dosage will be obtained.

It may be advantageous to formulate compositions in dosage unit form for ease of administration and uniformity of dosage. Each dosage unit form contains a predetermined quantity of the haplomers calculated to produce the amount of active effector product in association with a pharmaceutical carrier. The specification for the novel dosage unit forms is dependent on the unique characteristics of the targeted templated assembly composition, and the particular therapeutic effect to be achieved. Dosages are determined by reference to the usual dose and manner of administration of the ingredients.

The haplomer compositions may comprise pharmaceutically acceptable carriers, such that the carrier can be incorporated into the composition and administered to a patient without causing unacceptable biological effects or interacting in an unacceptable manner with other components of the composition. Such pharmaceutically acceptable carriers typically have met the required standards of toxicological and manufacturing testing, and include those materials identified as suitable inactive ingredients by the U.S. Food and Drug Administration.

The haplomers can also be prepared as pharmaceutically acceptable salts Such slats can be, for example, a salt prepared from a base or an acid which is acceptable for administration to a patient, such as a mammal (e.g., salts having acceptable mammalian safety for a given dosage regime). However, it is understood that the salts covered herein are not required to be pharmaceutically acceptable salts, such as salts of the haplomers that are not intended for administration to a patient. Pharmaceutically acceptable salts can be derived from pharmaceutically acceptable inorganic or organic bases and from pharmaceutically acceptable inorganic or organic acids. In addition, when a haplomer contains both a basic moiety, such as an amine, and an acidic moiety such as a carboxylic acid, zwitterions may be formed and are included within the term "salt" as used herein. Salts derived from pharmaceutically acceptable inorganic bases can include ammonium, calcium, copper, ferric, ferrous, lithium, magnesium, manganic, manganous, potassium, sodium, and zinc salts, and the like. Salts derived from pharmaceutically acceptable organic bases can include salts of primary, secondary and tertiary amines, including substituted amines, cyclic amines, naturally-occurring amines and the like, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids can include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids can include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The following representative embodiments are presented:

Embodiment 1

A nucleic acid molecule comprising: a) a first stem portion comprising from about 10 to about 20 nucleotide bases; b) an anti-target loop portion comprising from about 16 to about 40 nucleotide bases and having a first end to which the first stem portion is linked, wherein the anti-target loop portion is substantially complementary to a target nucleic acid molecule; c) a second stem portion comprising from about 10 to about 20 nucleotide bases linked to a second end of the anti-target loop portion, wherein the first stem portion is substantially complementary to the second stem portion; and d) a reactive effector moiety linked to either the first stem portion or the second stem portion; wherein the $T_m$ of the anti-target loop portion:target nucleic acid molecule is greater than the $T_m$ of the first stem portion:second stem portion.

Embodiment 2

The nucleic acid molecule of embodiment 1 wherein the $T_m$ of the first stem portion:second stem portion subtracted from the $T_m$ of the anti-target loop portion:target nucleic acid molecule is from about 10° C. to about 40° C.

Embodiment 3

The nucleic acid molecule of embodiment 1 or embodiment 2 wherein the $T_m$ of the first stem portion:second stem portion is from about 40° C. to about 50° C.

Embodiment 4

The nucleic acid molecule of any one of embodiments 1 to 3 wherein the $T_m$ of the anti-target loop portion:target nucleic acid molecule is from about 60° C. to about 80° C.

Embodiment 5

The nucleic acid molecule of any one of embodiments 1 to 4 wherein the $T_m$ of the first stem portion:second stem portion subtracted from the $T_m$ of the anti-target loop portion:target nucleic acid molecule is from about 10° C. to about 20° C.

Embodiment 6

The nucleic acid molecule of any one of embodiments 1 to 5 wherein the first stem portion comprises from about 12 to about 18 nucleotide bases.

Embodiment 7

The nucleic acid molecule of any one of embodiments 1 to 6 wherein the anti-target loop portion comprises from about 18 to about 35 nucleotide bases.

Embodiment 8

The nucleic acid molecule of any one of embodiments 1 to 7 wherein the second stem portion comprises from about 12 to about 18 nucleotide bases.

Embodiment 9

The nucleic acid molecule of any one of embodiments 1 to 8 wherein the nucleotide bases of any one or more of the first stem portion, anti-target loop portion, and second stem portion are selected from the group consisting of DNA nucleotides, RNA nucleotides, phosphorothioate-modified nucleotides, 2-O-alkylated RNA nucleotides, halogenated nucleotides, locked nucleic acid nucleotides (LNA), peptide nucleic acids (PNA), morpholino nucleic acid analogues (morpholinos), pseudouridine nucleotides, xanthine nucleotides, hypoxanthine nucleotides, 2-deoxyinosine nucleotides, DNA analogs with L-ribose (L-DNA), Xeno nucleic acid (XNA) analogues, or other nucleic acid analogues capable of base-pair formation, or artificial nucleic acid analogues with altered backbones, or any combination thereof.

Embodiment 10

The nucleic acid molecule of any one of embodiments 1 to 9 further comprising a linker between any one or more of the first stem portion and the anti-target loop portion, between the anti-target loop portion and the second stem portion, and between the second stem portion and the reactive effector moiety.

Embodiment 11

The nucleic acid molecule of embodiment 10 wherein the linker is selected from the group consisting of an alkyl group, an alkenyl group, an amide, an ester, a thioester, a ketone, an ether, a thioether, a disulfide, an ethylene glycol, a cycloalkyl group, a benzyl group, a heterocyclic group, a maleimidyl group, a hydrazone, a urethane, azoles, an imine, a haloalkyl, and a carbamate, or any combination thereof.

Embodiment 12

The nucleic acid molecule of any one of embodiments 1 to 11 wherein the reactive effector moiety is selected from the group consisting of a peptide, a non-active portion of a peptidomimetic structure, a non-active portion of a drug, and a bioactive compound.

Embodiment 13

The nucleic acid molecule of any one of embodiments 1 to 12 wherein the reactive effector moiety is less than 20 kDa.

Embodiment 14

The nucleic acid molecule of any one of embodiments 1 to 13 wherein the reactive effector moiety further comprises a bio-orthogonal reactive molecule.

Embodiment 15

The nucleic acid molecule of embodiment 14 wherein the bio-orthogonal reactive molecule is selected from the group consisting of an azide, an alkyne, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, and a quadricyclane, or any derivative thereof.

Embodiment 16

The nucleic acid molecule of any one of embodiments 1 to 15 wherein the anti-target loop portion further comprises an internal hinge region, wherein the hinge region comprises one or more nucleotides that are not complementary to the target nucleic acid molecule.

Embodiment 17

The nucleic acid molecule of embodiment 16 wherein the hinge region comprises from about 1 nucleotide to about 6 nucleotides.

Embodiment 18

The nucleic acid molecule of any one of embodiments 1 to 17 which comprises the nucleotide sequence 5'-ACTCGAGACGTCTCCTTGTCTTTGCTTTTCTTCA GGACACAGTGGCGAGACGTCTCGAGT-3' (SEQ ID NO:13) or 5'-ACTCGAGACGTCT CCTTCCTGCCCCTCCTCCTGCTCCGA-GACGTCTCGAGT-3' (SEQ ID NO:14).

Embodiment 19

A kit comprising: a first nucleic acid molecule according to any one of embodiments 1 to 18; and a second nucleic acid molecule comprising from about 6 nucleotide bases to about 20 nucleotide bases, which comprises: a nucleotide portion that is substantially complementary to the stem portion of the first nucleic acid molecule that is linked to the reactive effector moiety; and a reactive effector moiety which can chemically interact with the reactive effector molecule of the first nucleic acid molecule; wherein the $T_m$ of the second nucleic acid molecule:first or second stem portion linked to the reactive effector moiety is less than or equal to the $T_m$ of the first stem portion:second stem portion.

Embodiment 20

The kit of embodiment 19, wherein: the reactive effector moiety of the second nucleic acid molecule is linked to a bio-orthogonal reactive molecule; the reactive effector moiety of the first nucleic acid molecule is linked to a bio-orthogonal reactive molecule; the bio-orthogonal reactive molecule of the second nucleic acid molecule can chemically interact with the bio-orthogonal reactive molecule of the first nucleic acid molecule.

Embodiment 21

The kit of embodiment 19 or embodiment 20 wherein the $T_m$ of the duplex formed by the second nucleic acid molecule and the first or second stem portion linked to the reactive effector moiety subtracted from the $T_m$ of the first stem portion:second stem portion is from about 0° C. to about 20° C.

Embodiment 22

The kit of any one of embodiments 19 to 21 wherein the $T_m$ of the duplex formed by the second nucleic acid molecule and the first or second stem portion linked to the reactive effector moiety is from about 30° C. to about 40° C.

Embodiment 23

The kit of any one of embodiments 19 to 22 wherein the $T_m$ of the duplex formed by the nucleic acid molecule and the first or second stem portion linked to the reactive effector moiety subtracted from the $T_m$ of the first stem portion: second stem portion is from about 5° C. to about 10° C.

Embodiment 24

The kit of any one of embodiments 19 to 2.3 wherein the second nucleic acid molecule comprises from about 8 to about 15 nucleotide bases.

Embodiment 25

The kit of any one of embodiments 19 to 24 wherein: the first nucleic acid molecule comprises the nucleotide sequence of SEQ ID NO:13, and the second nucleic acid molecule comprises the nucleotide sequence 5'-AGCTCTCGAGT-3' (SEQ ID NO:15); or the first nucleic acid molecule comprises the nucleotide sequence of SEQ ID NO:14, and the second nucleic acid molecule comprises the nucleotide sequence 5'-GACGTCTCGAGT-3' (SEQ ID NO:16).

Embodiment 26

The kit of any one of embodiments 19 to 25 wherein the bio-orthogonal reactive molecule of the first nucleic acid molecule is hexynyl and the bio-orthogonal reactive molecule of the second nucleic acid molecule is azide.

Embodiment 27

A method of producing a templated assembly product for a cell comprising: contacting a target nucleic acid molecule of the cell with a first nucleic acid molecule of any one of embodiments 1 to 18; and contacting the first nucleic acid molecule with a second nucleic acid molecule, wherein the second nucleic acid molecule comprises: a nucleotide portion that is substantially complementary to the stem portion of the first nucleic acid molecule that is linked to the reactive effector moiety: and a reactive effector moiety which can chemically interact with the reactive effector molecule of the first nucleic acid molecule; wherein the $T_m$ of the second nucleic acid molecule:first or second stem portion linked to the reactive effector moiety is less than or equal to the $T_m$ of the first stem portion:second stem portion; resulting in the combination of the respective reactive effector moieties thereby producing the templated assembly product.

Embodiment 28

The method of embodiment 27 wherein: the first nucleic acid molecule comprises the nucleotide sequence of SEQ ID NO:13, and the second nucleic acid molecule comprises the nucleotide sequence 5'-AGCTCTCGAGT-3' (SEQ ID NO:15); or the first nucleic acid molecule comprises the nucleotide sequence of SEQ ID NO:14, and the second nucleic acid molecule comprises the nucleotide sequence 5'-GACGTCTCGAGT-3' (SEQ ID NO:16).

Embodiment 29

The method of embodiment 27 or embodiment 28 wherein the bio-orthogonal reactive molecule of the first nucleic acid molecule is hexynyl and the bio-orthogonal reactive molecule of the second nucleic acid molecule is azide.

In order that the subject matter disclosed herein may be more efficiently understood, examples are provided below. It should be understood that these examples are for illustrative purposes only and are not to be construed as limiting the claimed subject matter in any manner.

EXAMPLES

Example 1: The Locked-Template Assembly by Proximity-Enhanced Reactivity (TAPER) System with an Oligonucleotide Model Target The conditions of these experiments were designed to demonstrate that only in the presence of specific template (e.g., target nucleic acid molecule) would the first nucleic acid molecule (i.e., haplomer bottle) open and render the first stem portion or the second stem portion thereof, whichever is linked to the reactive effector moiety, available for hybridization with the complementary second nucleic acid molecule (e.g., second haplomer).

Figure 9:
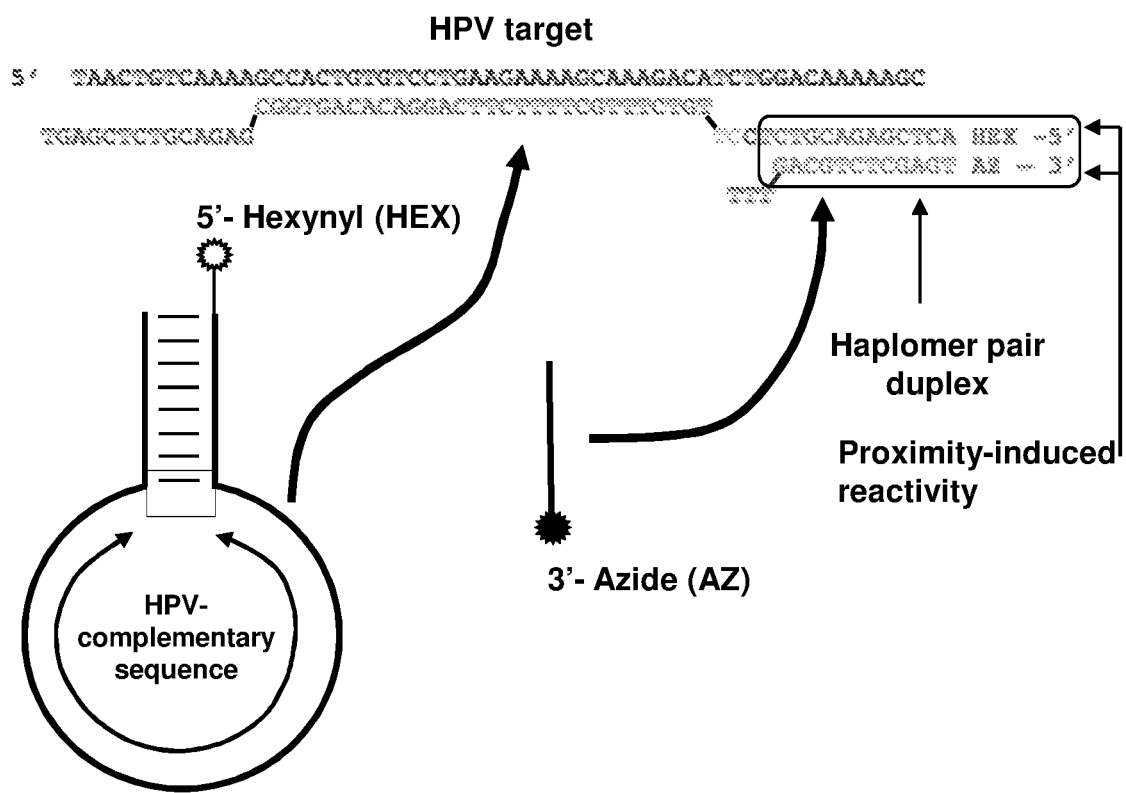
FIG. 9 shows a representative target nucleic acid molecule sequence (5'-TAACTG TCAAAAGCCACTGTGTCCT-GAAGAAAAGCAAAGACATCTGGACAAAAAGC-3'; SEQ ID NO:1) and structures of initial model oligonucleotides (first nucleic acid molecule is 5'-hexynyl-ACTCGA-GACGTCTCTGTCTTTGCTTTTCTTCAGGACACAGTGGCGA-GA CGTCTCGAGT-3' (SEQ ID NO:7); and second nucleic acid molecule is 5'-TTTGACGTCT CGAGT-azide-3' (SEQ ID NO:8)) designed to examine the ability of locked constructs to overcome the template titration effect.

In initial experiments, the first and second nucleic acid molecules comprised the bio-orthogonal reactive molecules hexynyl- and azide-groups appended to their 5' and 3' ends by standard chemistries. The target nucleic acid molecule selected was a DNA single-stranded oligonucleotide copy of a segment of HPV E6/E7 transcript (see, FIG. 9). The general experimental plan used several different incubation conditions with the relevant component molecules. An initial incubation was performed (using varying times and temperatures) of the first nucleic acid molecule with or without the target nucleic acid molecule, followed by a subsequent incubation with the second nucleic acid molecule. After this, all samples were split and treated with or without reagents for catalyzing click reactions between the linear alkyne (hexynyl) and azide moieties appended to the 5' and 3' ends of the first and second nucleic acid molecule, respectively.

The initial incubation was performed at 37° C. in 25 µl of 10 mM Tris-HCl (pH 7.5), 10 mM $MgCl_2$, 50 mM NaCl, and 1 mM dithioerythritol. The HPV DNA target nucleic acid molecule (oligonucleotide code #34) was present at 4 µM, in a two-fold molar excess over the first nucleic acid molecule (oligonucleotide code #249). Before use, the first nucleic acid molecule was subjected to "pre-self-annealing" to ensure maximal intramolecular formation of the bottle structure. For this purpose, 1250 pmol of the first nucleic acid molecule (#249) in 25 µl of 10 mM Tris-HCl (pH 7.5), 10 mM $MgCl_2$, 50 mM NaCl, and 1 mM dithioerythritol was subjected to 5 minutes at 80° C. treatment, followed by rapid chilling at 0° C. for at least 10 minutes. From this, 1 µl (50 pmol) was used for the experimental tests. When the second nucleic acid molecule was added, it was at an equimolar concentration with the first nucleic acid molecule (2 µM). The following incubation conditions were examined:

A) HPV target nucleic acid molecule+first nucleic acid molecule for 2 hours at 37° C.;

B) First nucleic acid molecule alone, for 2 hours at 37° C.;

C) HPV target nucleic acid molecule+first nucleic acid molecule, for 2 hours at 25° C.;

D) HPV target nucleic acid molecule+first nucleic acid molecule, heated for 5 minutes at 80° C., followed by slow cooling to 25° C.; and E) HPV target nucleic acid molecule+first nucleic acid molecule, with no preincubation.

Following the initial incubation, the second nucleic acid molecule was added, and all were incubated for an additional hour at 37° C. All samples were then subjected to +/−click reactions between the respective bio-orthogonal reactive molecules in the following manner Ten (10) µl from each annealing (20 pmol of first and second nucleic acid molecules) were activated for Cu(I) click catalysis with Tris (3-hydroxypropyltriazolyl methyl) amine (THPTA), or in equivalent buffer lacking click catalyst. A premix of the following components was prepared with additions in the following order: 20 µl of 70 mM THPTA in 0.155 M NaCl; 4 µl of 500 mM Na-ascorbate in 0.155 M NaCl; and 2 µl of 100 mM CuSO$_4$ in 0.155 M NaCl. To each of the tubes for the click reaction, 2.6 µl of this premix was added, such that the final volume was 50 µl in 1× phosphate-buffered saline.

Tubes were incubated for 30 minutes at 0° C. (on ice), and then 2 hours at 25° C. At the end of the incubation period, the tube contents were desalted though Bio-Rad P6 (in 10 mM Tris pH 7.4, performed according to the manufacturer's instructions) and precipitated with 20 µg of glycogen (Sigma), 0.3 M sodium acetate, and 3 volumes of ethanol. After centrifugation, the pellets were washed with 1 ml of 70% ethanol, dried, and re-dissolved in 4 µl of TE (5 pmol/µl of first and second nucleic acid molecules). Samples (1 µl) were analyzed on 10% 8 M urea denaturing 10% (19:1) acrylamide gels after denaturation in 98% formamide at 98° C. for 3 minutes and immediate transfer to ice.

Figure 10:
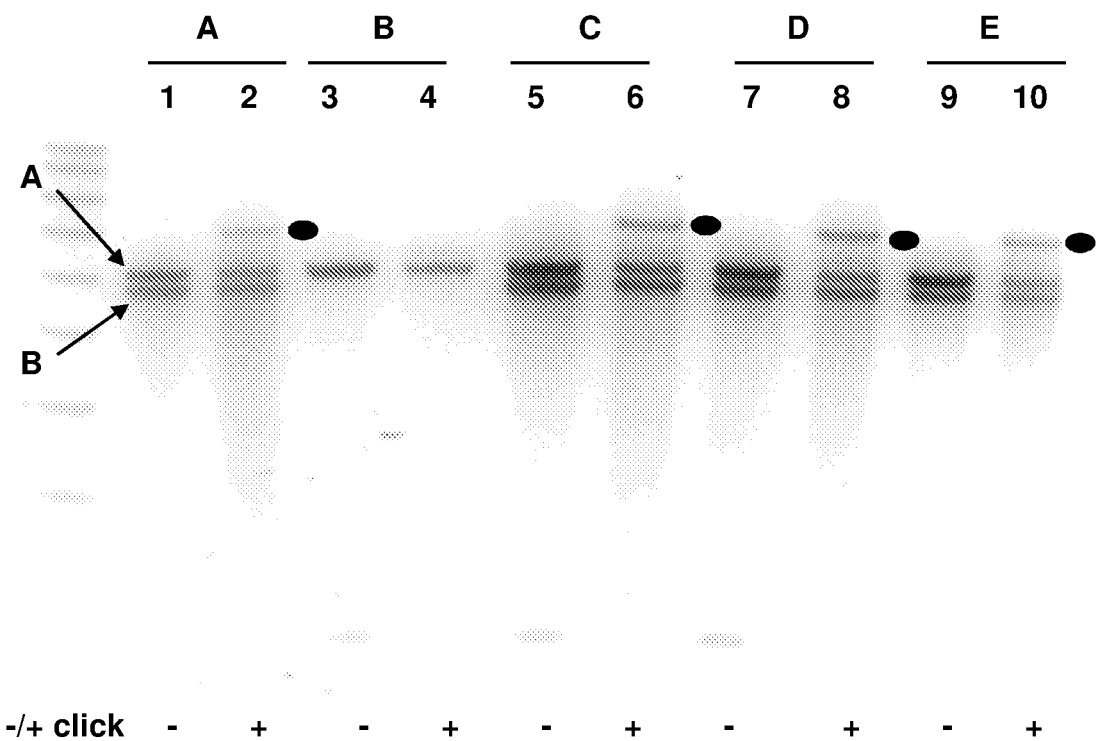
FIG. 10 shows a representative examination of locked TAPER model oligonucleotides (see, FIG. 9 sequences) using various incubation conditions.

Results of this experiment are shown in FIG. 10. No click product was observed in the absence of the target nucleic acid molecule (see, B conditions, Lanes 3 and 4), and product was observed irrespective of whether the incubation temperature was 37° C. or 25° C. (see, A and C conditions, lanes 1, 2, and 5,6 respectively). The treatment where an initial high-temperature denaturation step was used served to control for the role of the bottle structure of the first nucleic acid molecule, by means of its forcible removal prior to the incubation with the target nucleic acid molecule. However, this did not significantly affect the yield of the click product (see, D conditions, lanes 7 and 8). The requirement for a pre-incubation of the target nucleic acid molecule and first nucleic acid molecule with this experimental protocol was tested, and had only a minor impact on click product formation (see, E conditions, lanes 9,10). Thus, comparable results were obtained when both the first nucleic acid molecule, the second nucleic acid molecule, and the target nucleic acid molecule were mixed together from the commencement of the incubation period.

Figure 11:
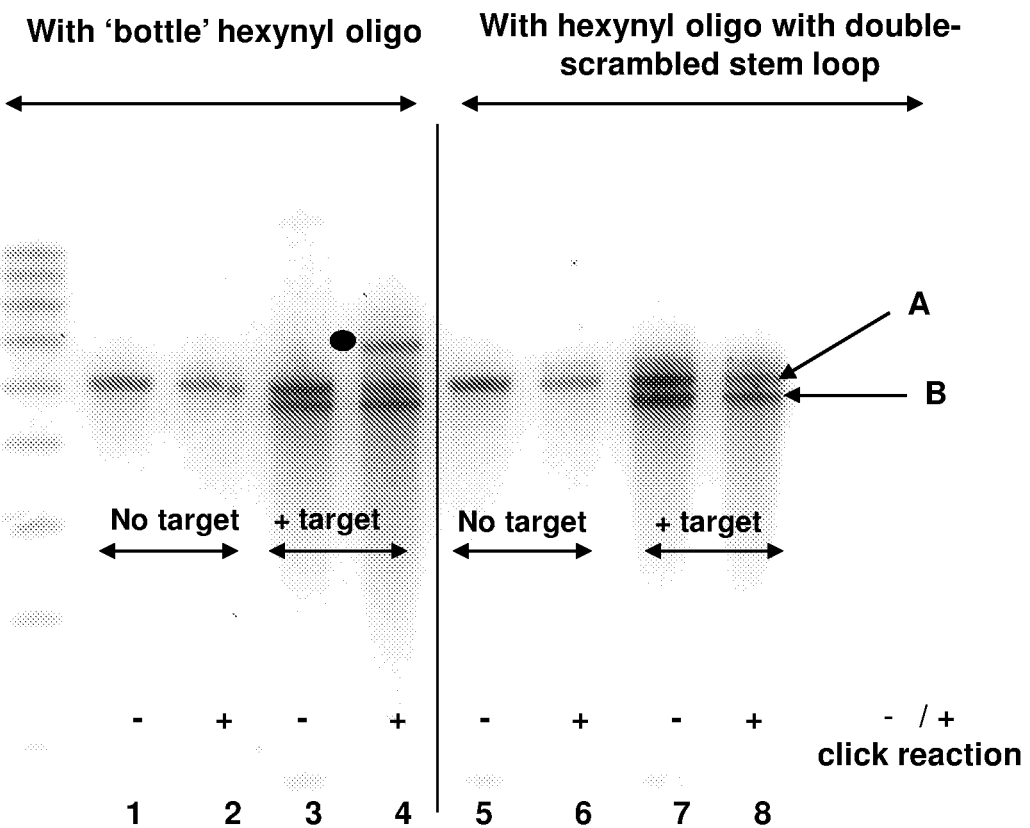
FIG. 11 shows a representative examination of locked TAPER model oligonucleotides (see, FIG. 9 sequences) using a control hexynyl oligonucleotide where both self-complementary ends forming the stem loop are scrambled such that the bottle structure cannot form, and no hybridization site for the second haplomer is present.

The specificity of the click product formation was probed by the use of an oligonucleotide version of the initial first nucleic acid molecule where both the first and second stem portion sequences were randomly scrambled (code #261), in comparison to the original (#249) oligonucleotide. Experimental conditions were as above, except a single combined 30 minute incubation (with no pre-incubation) was used for all components. Following this incubation period, samples were subjected to +/−treatment with agents catalyzing click reactions, as described above (see, Example 1, FIG. 10). Samples were subsequently analyzed on a 10% denaturing gel with 8 M urea, and stained with SYBR-Gold (Thermofisher). Results confirmed that for the (#249) first nucleic acid molecule, click product was only observed in the presence of the target nucleic acid molecule (see, FIG. 11, lanes 1 vs. 2; 3 vs 4). No product was observed with the control (#261) template where both of the stem loops had the same base composition but scrambled sequences, demonstrating the requirement for specific templating in the reaction mediated by the click groups.

Figure 12:
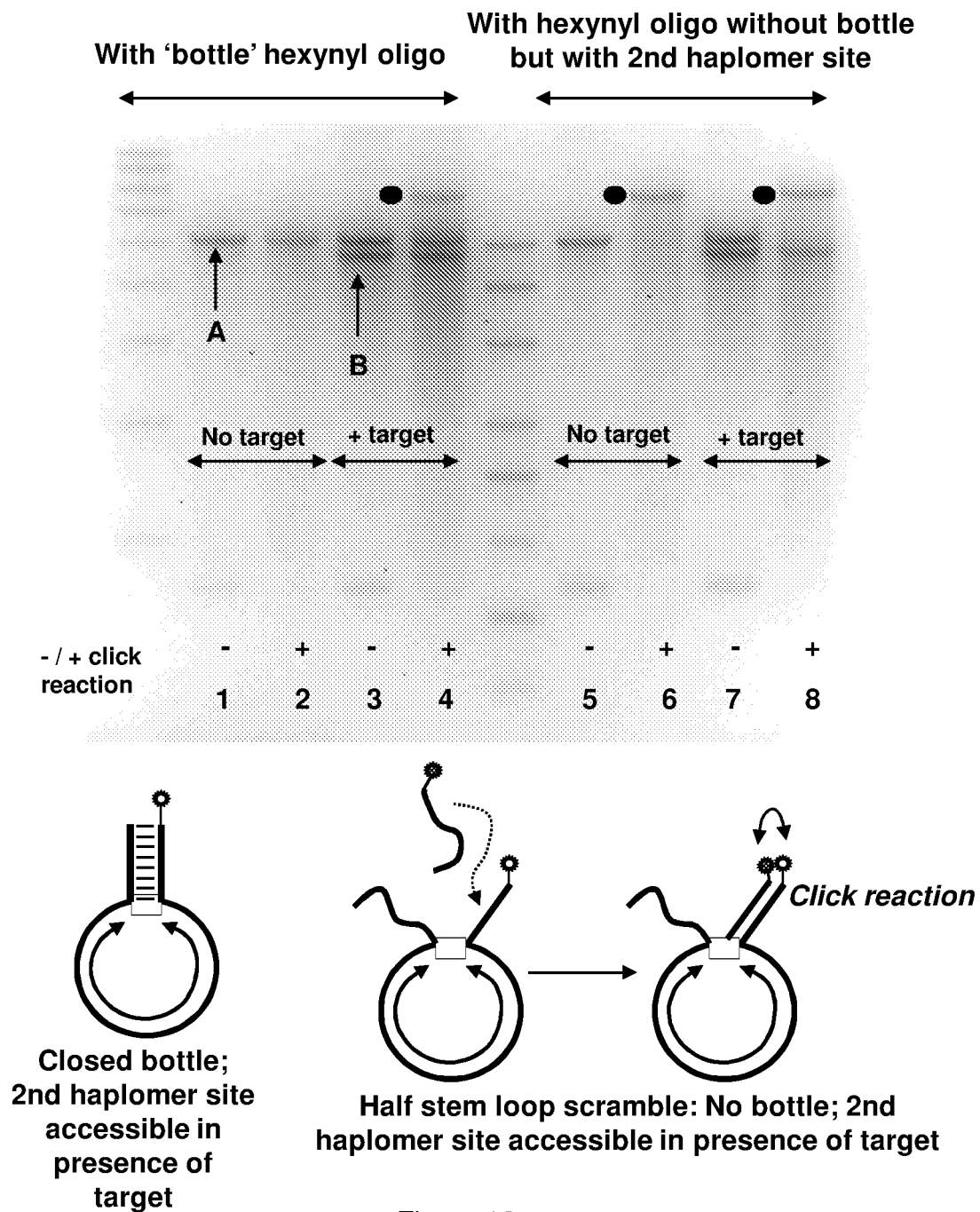
FIG. 12 shows a representative examination of locked TAPER model oligonucleotides (see, FIG. 9 sequences) using a control hexynyl oligonucleotide where a single stem loop segment is scrambled such that the bottle structure could not form, while the hybridization site for the second haplomer is still present.

A further examination of the locked TAPER system used a control 5'-hexynyl oligonucleotide where only one of the two complementary sequences forming the first nucleic acid molecule stem loop was scrambled (as opposed to the above control where both such sequences were scrambled). In this additional control oligonucleotide (code #325), the sequence complementary to the second nucleic acid molecule was maintained, although no loop bottle could form. Both the original HPV first nucleic acid molecule loop bottle (#249) and single-scrambled control (#325) were subjected to a 2 hour pre-incubation with or without a two-fold excess of HPV target nucleic acid molecule, followed by an additional 1 hour incubation with the second nucleic acid molecule (#250), and then standard+/−click reactions as described above. Processed samples were examined on 15% 8 M urea gels (see, FIG. 12). These results clearly demonstrated that in the absence of loop bottle formation (as with the single-scrambled control #325), click product formation was independent of target nucleic acid molecule, even though the target-complementary segment was still present. As before, however, with the first nucleic acid molecule (#249), HPV target nucleic acid molecule sequence was required before click product was observed (see, FIG. 12).

Oligonucleotides used:
1) HPV first nucleic acid molecule sequence (#249; 60-mer; annotations from 5'-3': bold=first nucleic acid molecule sequence (H1); plain CT=additional hinge sequence; underlined=HPV-target nucleic acid molecule complementary sequence; small letters=complement to first nucleic acid molecule sequence (H2)):

(SEQ ID NO: 13)
5' Hexynyl- ACTCGAGACGTCTCCTTGTCTTTGCTTTTCTTCAGGAC

ACAGTGGCgagacgtctcgagt-3'.

2) Second nucleic acid molecule (#250; 15-mer; annotations from 5'-3': TTT=non-specific size extender; bold=second nucleic acid molecule sequence (H2)):

(SEQ ID NO: 8)
5'-TTTGACGTCTCGAGT-azide-3'.

3) HPV DNA target nucleic acid molecule (#34; 56-mer):

(SEQ ID NO: 1)
5'-TAACTGTCAAAAGCCACTGTGTCCTGAAGAAAAGCAAAGACATCTGG

ACAAAAAGC-3'.

4) HPV first nucleic acid molecule with double scrambled stem sequences (#261; 60-mer):

(SEQ ID NO: 17)
5'-Hexynyl-GACAGCACCTTCGTCTTGTCTTTGCTTTTCTTCAGGACA

CAGTGGCGGGCTGCGACAATT.

5) HPV first nucleic acid molecule with single scrambled stem sequence, where the 5' sequence complementary to the second nucleic acid molecule is maintained (#325; 60-mer):

(SEQ ID NO: 18)
5'-Hexynyl-ACTCGAGACGTCTCCTTGTCTTTGCTTTTCTTCAGGACA

CAGTGGCGGGCTGCGACAATT.

Example 2: Locked TAPER Template Dose-Response with an RNA Oligonucleotide

The locked TAPER oligonucleotides used in Example 1 were examined with an RNA target nucleic acid molecule (code #322, corresponding to a truncated version of the HPV target nucleic acid molecule also used in Example 1). Similar conditions as for Example 1 were used with the first nucleic acid molecule (#249) in terms of quantities (50 pmol; 2 pmol/μl during template and second nucleic acid molecule hybridizations; 0.4 pmol/μl during click reactions) and incubation times (2 hour first nucleic acid molecule/ RNA target nucleic acid molecule annealings; 1 hour for subsequent incubations with the second nucleic acid molecule (#250)). The RNA target nucleic acid molecule was used in a range of molar ratios ranging from 0.05:1 (target nucleic acid molecule:first and second nucleic acid molecule) to 100:1. Where the amount of RNA target nucleic acid molecule was equal to or greater than 5:1, it was necessary after the +/−click reactions (performed in an identical manner as for Example 1) to remove the target nucleic acid molecule prior to gel analysis, to avoid interference with band patterns. This was readily performed by means of alkaline hydrolysis, consisting of a treatment of the preparations with 0.2 M NaOH for 20 minutes at 70° C., followed by neutralization with acetic acid/sodium acetate. All preparations were precipitated, washed with 70% ethanol, dried, and reconstituted with 4 μl of TE (10/1.0). Samples (1.0 μl) were run on denaturing 15% 8 M urea gels. It was observed (see, FIG. 13) that click products were promoted by the presence of the RNA target nucleic acid molecule, and were still present even when the target nucleic acid molecule was in a 100-fold molar excess.

Oligonucleotide used in addition to #249 and #250 of Example 1:

6) HPV RNA target nucleic acid molecule (#322; 34-mer):

(SEQ ID NO: 19)
5'-AAGCCACUGUGUCCUGAAGAAAAGCAAAGACAUC.

Example 3: Hybridization Kinetics for Locked TAPER Haplomers in the Presence of Specific Target Since the stem-loop in first nucleic acid molecule enforces a very distinct structural motif compared with a linear oligonucleotide, it was predicted that first nucleic acid molecule would show a readily detectable mobility difference in non-denaturing acrylamide gels relative to unstructured oligonucleotides of the same size. This was in turn used to examine the kinetics of hybridization between the anti-target loop region within the first nucleic acid molecules and specific target nucleic acid molecules (such hybridization should produce a marked change in migration behavior in non-denaturing acrylamide gels).

In 10 μl replicates of the same buffer as used for Example 1 (10 mM Tris-HCl (pH 7.5), 10 mM MgCl$_2$, 50 mM NaCl, and 1 mM dithioerythritol), 50 pmol of the HPV first nucleic acid molecule (#249) was mixed with 100 pmol of the HPV target nucleic acid molecule (#34). These tubes were subjected to incubation at 37° C. for 5, 15, 30, 60, and 120 minutes, with a zero-time point corresponding to mixing of the tube immediately prior to gel loading. After each time point, the relevant tube was snap frozen at −80° C. until loading (1 μl of each; 5 pmol and 10 pmol of the HPV first nucleic acid molecule and HPV target nucleic acid molecule, respectively) on a 10% non-denaturing acrylamide gel (1×TBE). Results are shown in FIG. 14. The HPV first nucleic acid molecule (#249) alone (see, Lane A) had a markedly accelerated mobility in comparison to two arbitrary oligonucleotides of the same lengths (60 bases; see, Lanes 60a and 60b), consistent with its pronounced secondary structure. Oligonucleotides 60a and 60b did not have equivalent mobilities, suggesting sequence-specific mobility effects in the non-denaturing gel, but nevertheless were easily distinguishable from the HPV first nucleic acid molecule (#249)). The HPV target nucleic acid molecule alone (#34, see, Lane B) ran at an approximately similar position as 60a and 60b. However, hybridization between the HPV first nucleic acid molecule and HPV target nucleic acid molecule was evidently rapid, with the bottle band completely removed after 5 minutes incubation. Concomitant with this, slower-moving forms were observed on the gel, including discrete bands and unresolved (smeared) material. (Under the conditions used, even the "time zero" point had reduced amounts of the unhybridized bottle, and evidence of slower-migrating products, suggesting that observable hybridization occurred during sample mixing and transfer to a gel lane). This confirms that the HPV first nucleic acid molecule exists in a discrete structural state under normal temperatures, and that hybridization between the HPV first nucleic acid molecule and HPV target nucleic acid molecule occurs readily, with concomitant removal of the "bottle" structure.

Oligonucleotides used in addition to #249 and #34 of Example 1:

7) Unrelated 60-mers:

60a (code #11):
(SEQ ID NO: 20)
5' p-CCTTTTTTTAGGAGAAGGAGACTTAGAGGCCATCTCCACCTCCAT AACCCATTTTTTTCC-3';
and 60b (code #71):
(SEQ ID NO: 21)
5'-GGAAAAAAATGGGTTATGGAGGTGGAGATGGCCTCTAAGTCTCCTTC

TCCTAAAAAAAGG-3'.

Example 4: Locked-TAPER System with a Cellular RNA Bearing a Repeat Motif

An independent examination of the locked TAPER technology was chosen in the form of a repeat region found in Epstein-Barr Virus (EBV) transcripts containing a coding sequence for the EBNA1 gene. The ability to target a multiply-repeated motif confers distinct benefits (some of which are described herein). In this examination, both a DNA single copy of the repeat region was used as the target nucleic acid molecule, as well as whole cellular RNA from an EBV-transformed lymphoblastoid cell line.

Figure 16:
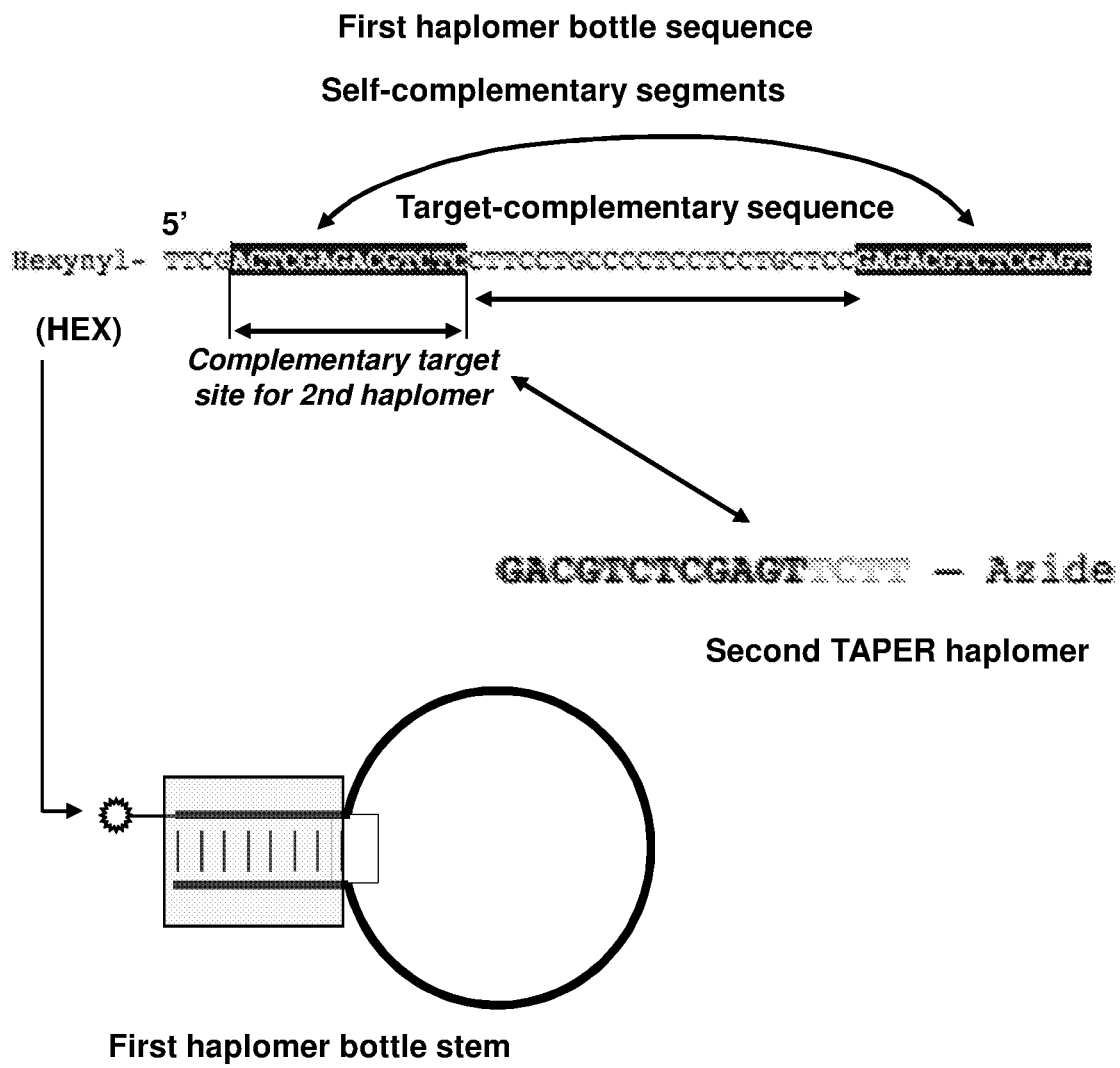
FIG. 16 shows sequence and structural arrangements for representative oligonucleotides (the first nucleic acid molecule is 5'-hexynyl-TTCGACTCGAGACGTCTC CTTCCTGCCCCTCCTCCTGCTCCGA-GACGTCTCGAGT-3' (SEQ ID NO:10); and second nucleic acid mole is 5'-GACGTCTCGAGTTCTT-azide-3' (SEQ ID NO:11)) for the locked TAPER using an EBNA1 repeat motif (5'AGTTGCAGGAGCAGGAGGAGGGGCAG-GAGCA GGAG-3'; SEQ ID NO:12).

The EBNA1 gene consists of 5' and 3' unique regions, between which is located a highly repetitive tract (REF). For this examination, a specific 21-base segment was chosen as the target nucleic acid molecule, of which there are 14 identifiable copies within the boundaries of the whole EBNA1 repeat region (see, FIG. 15). An EBNA1-specific first nucleic acid molecule was designed (see, FIG. 16) with the complement to the 21-base target nucleic acid molecule as the loop sequence, and with the same nucleic acid molecule/nucleic acid molecule—complement sequences as for the HPV first nucleic acid molecule of Example 1. An additional 4-base 5' sequence was included as a flexible spacer. The structure of the EBNA1-specific first nucleic acid molecule hybridized with both the model EBNA1 target nucleic acid molecule and the second nucleic acid molecule are shown in FIG. 17. The second nucleic acid molecule sequence complementary to the first nucleic acid molecule was identical to that used in Example 1; in this case, the second nucleic acid molecule bears an additional 4-base spacer sequence.

Figure 18:
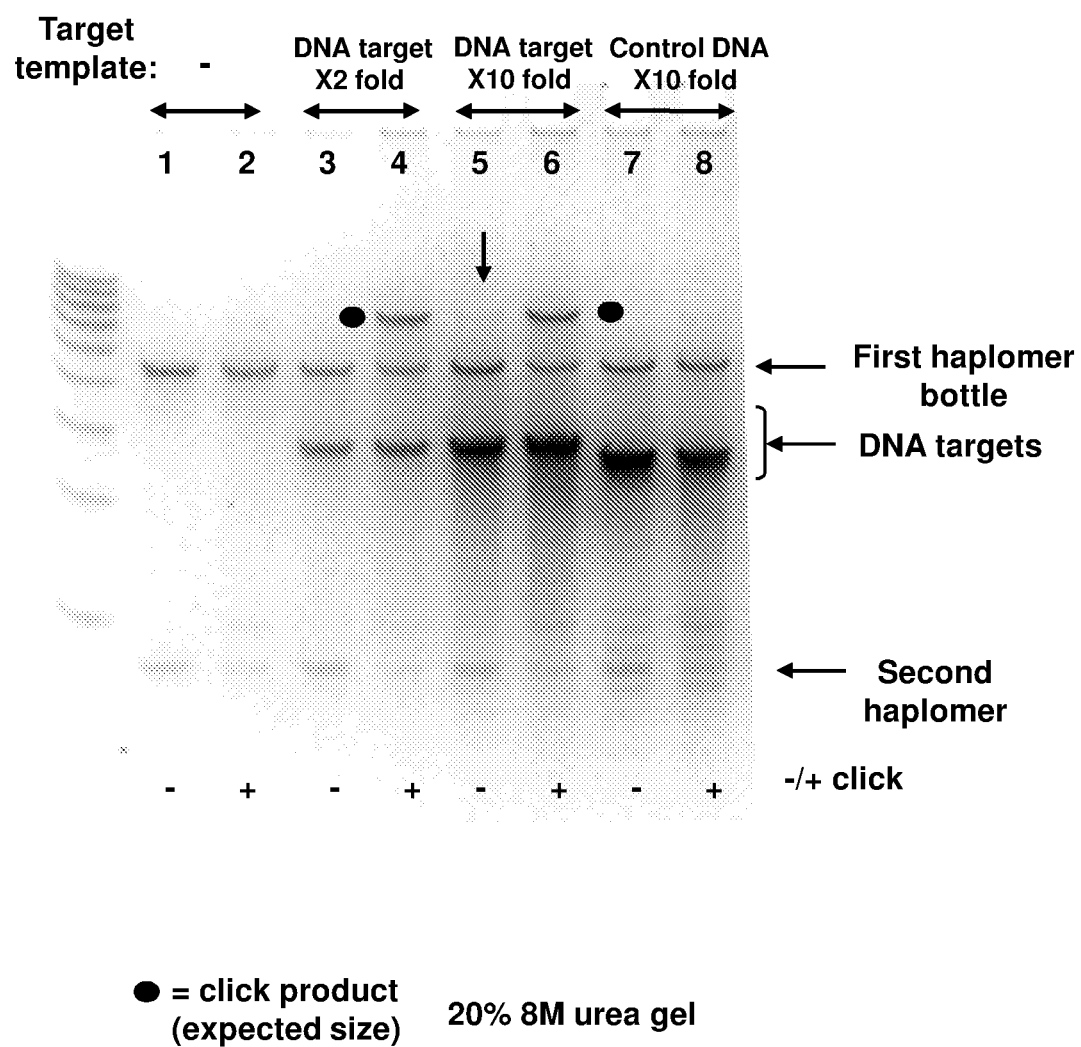
FIG. 18 shows results of a representative locked TAPER model EBNA1 oligonucleotides (see, FIG. 12 sequences) using an oligonucleotide target.

Studies were performed with the EBNA1 first nucleic acid molecule and second nucleic acid molecule with the DNA oligonucleotide nucleic acid molecule corresponding to the EBNA1 repeat sequence. The EBNA1 first nucleic acid molecule was initially pre-self-annealed in the same manner as for the first nucleic acid molecule in Example 1. Samples of the self-annealed first nucleic acid molecule were then incubated in 10 mM Tris-HCl (pH 7.5), 10 mM MgCl$_2$, 50 mM NaCl, and 1 mM dithioerythritol at a final concentration of 2 µM, along with the DNA target nucleic acid molecule at both 2-fold and 10-fold excess concentrations. In addition, a control non-specific DNA oligonucleotide was used, also at a 10-fold excess concentration. After a 2 hour incubation at 37° C., the second nucleic acid molecule was added to a final concentration of 2 µM, and the incubation continued for a final 1 hour at 37° C. Following this, 10 µl samples from each examination were subjected to +/−click reactions in the same manner as for Example 1. Samples (1 µl) were analyzed on 10% 8 M urea denaturing 10% (19:1) acrylamide gels after denaturation in 98% formamide at 98° C. for 3 minutes and immediate transfer to ice. Results (see, FIG. 18) showed that in the absence of target nucleic acid molecule, no click product was observed (see, Lanes 1 and 2). Product was observed when the specific EBNA1 target nucleic acid molecule sequence was present (see, Lanes 3-6), but not with the non-specific control oligonucleotide (see, Lanes 7 and 8). A sequence-dependent mobility difference was observed for the EBNA1-specific target nucleic acid molecule and non-specific control oligonucleotides, despite their being of identical lengths (35-mers). Moreover, the click product yield was increased with the greater (10-fold) molar excess of specific target nucleic acid molecule (see, Lanes 5 and 6) as predicted if the titration effect was absent. It was notable that with the higher target nucleic acid molecule level, a faint click product band was observed even in the absence of Cu(I) catalyst (see, black arrow, Lane 5), indicative of the increased levels of hexynyl- and azide-linked first and second nucleic acid molecules brought into proximity via concomitant increased levels of "open" first nucleic acid molecule.

Figure 19:
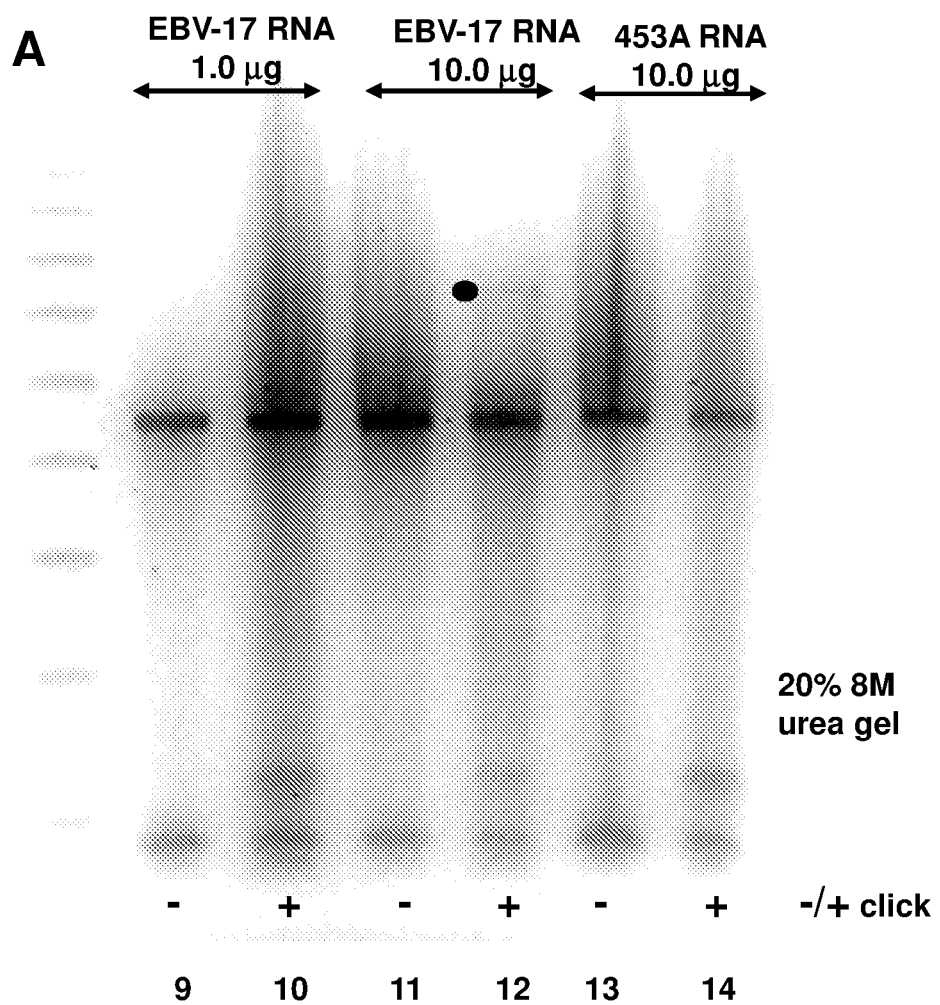
FIG. 19 (panels A and B) shows results of a representative locked TAPER model EBNA1 oligonucleotides (see, FIG. 12 sequences) using RNA targets; panel A shows gel results from two quantities of RNA (1.0 and 10.0 µg) extracted from the EBV-bearing lymphoblastoid cell line EBV-17, along with control RNA from the non-EBV-bearing melanoma line 453A; panel B shows the same gel as Panel B, but at a lighter exposure.
Figure 19:
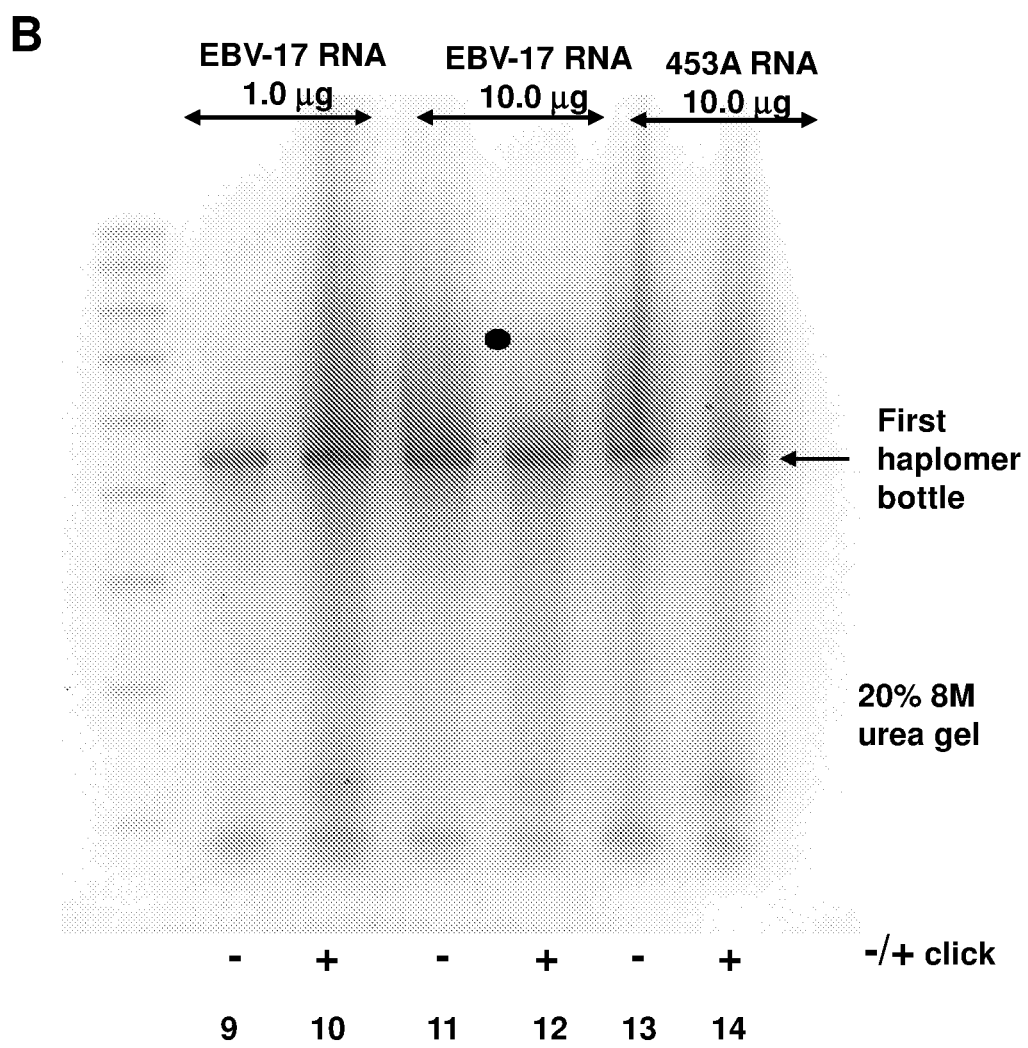

The same EBNA1 locked TAPER oligonucleotides were then used to examine product formation in the presence of cellular RNA nucleic acid molecules with or without EBV sequences. Whole RNA was prepared from the lymphoblastoid cell line EBV-17 (origin details; known to possess EBV genomes and express EBV sequences) and from a control melanoma cell line (453A) negative for EBV. Incubations were set up in an identical manner as for the above EBNA1 locked TAPER examinations with the specific EBNA1 target nucleic acid molecule (as above), except that all preparations were supplemented with 30 units of murine RNase inhibitor (New England Biolabs). Post-incubation+/−click reactions were likewise performed in the same manner as above. Upon gel analysis and staining as before, it was shown that click product was detectable with 10 µg (but not 1 µg) of EBV-17 RNA (see, FIG. 19). No product was detectable with 10 µg control 453A RNA. These results indicate that a specific repetitive cellular target can be used for successful locked TAPER.

Oligonucleotides used:
8) EBNA1 first nucleic acid molecule (55-mer; code #283; annotations from 5'-3': TTCG=spacer tract; bold=first nucleic acid molecule sequence (H1); plain CT=additional hinge sequence; underlined=HPV-target nucleic acid molecule complementary sequence; small letters=complement to first nucleic acid molecule sequence (H2): 5' Hexynyl-TTCGACTCGA-GACGTCTCCTTCCTGCCCCTCCTC CTGCTCCGAGACGTCTCGAGT-3' (SEQ ID NO:10);
9) EBNA1 second nucleic acid molecule (16-mer; code #284; annotations from 5'-3': bold=second nucleic acid molecule sequence (H2); TCTT=spacer sequence):

(SEQ ID NO: 11)
5'-GACGTCTCGAGTTCTT-azide-3';

10) EBNA1 repeat region DNA model target nucleic acid molecule (35-mer; code #282; annotations: bold=DNA copy of repeat sequence target nucleic acid molecule; remainder=flanking sequence): 5'-AGTTGCAG-GAGCAGGAGGAGGGGCAGGA GCAGGAG-3' (SEQ ID NO:12); and
11) Control non-specific oligonucleotide for EBNA1 (35-mer; code #217):

(SEQ ID NO: 22)
5'-GACTAGACGGCCAGGGAGACGAATACATATTCAAT-3'.

Various modifications of the described subject matter, in addition to those described herein, will be apparent to those skilled in the art from the foregoing description. Such modifications are also intended to fall within the scope of the appended claims Each reference (including, but not limited to, journal articles, U.S. and non-U.S. patents, patent applications, patent application publications, international patent application publications, gene bank accession numbers, and the like) cited in the present application is incorporated herein by reference in its entirety.

What is claimed is:

1. A nucleic acid molecule comprising:
   a) a first stem portion comprising from about 10 to about 20 nucleotide bases;
   b) an anti-target loop portion comprising from about 16 to about 40 nucleotide bases and having a first end to which the first stem portion is linked, wherein the anti-target loop portion is substantially complementary to a target nucleic acid molecule;
   c) a second stem portion comprising from about 10 to about 20 nucleotide bases linked to a second end of the anti-target loop portion, wherein the first stem portion is substantially complementary to the second stem portion; and
   d) a reactive effector moiety linked to either the first stem portion or the second stem portion;
   wherein the Tm of the anti-target loop portion:target nucleic acid molecule is greater than the Tm of the first stem portion:second stem portion; and
   wherein the nucleic acid molecule comprises the nucleotide sequence 5'-ACTCGAGACGTCTCCTTGTCTTTGCTTTTCTTCAGGACACAGTGGCGAGACGTCTCGAGT-3' (SEQ ID NO:13) or 5'-ACTCGAGACGTCTCCTTCCTGCCCCTCCTCCTGCTCCGAGACGTCTCGAGT-3' (SEQ ID NO:14).

2. A kit comprising:
   a first nucleic acid molecule comprising:
   a) a first stem portion comprising from about 10 to about 20 nucleotide bases;
   b) an anti-target loop portion comprising from about 16 to about 40 nucleotide bases and having a first end to which the first stem portion is linked, wherein the anti-target loop portion is substantially complementary to a target nucleic acid molecule;
   c) a second stem portion comprising from about 10 to about 20 nucleotide bases linked to a second end of the anti-target loop portion, wherein the first stem portion is substantially complementary to the second stem portion; and
   d) a reactive effector moiety linked to either the first stem portion or the second stem portion;
   wherein the Tm of the anti-target loop portion:target nucleic acid molecule is greater than the Tm of the first stem portion:second stem portion; and
   a second nucleic acid molecule comprising from about 6 nucleotide bases to about 20 nucleotide bases, which comprises:
   a nucleotide portion that is substantially complementary to the stem portion of the first nucleic acid molecule that is linked to the reactive effector moiety; and
   a reactive effector moiety which can chemically interact with the reactive effector molecule of the first nucleic acid molecule;
   wherein the Tm of the second nucleic acid molecule:first or second stem portion linked to the reactive effector moiety is less than or equal to the Tm of the first stem portion:second stem portion.

3. The kit of claim 2, wherein:
   the reactive effector moiety of the second nucleic acid molecule is linked to a bio-orthogonal reactive molecule;
   the reactive effector moiety of the first nucleic acid molecule is linked to a bio-orthogonal reactive molecule;
   the bio-orthogonal reactive molecule of the second nucleic acid molecule can chemically interact with the bio-orthogonal reactive molecule of the first nucleic acid molecule.

4. The kit of claim 2 wherein:
   the Tm of the duplex formed by the second nucleic acid molecule and the first or second stem portion linked to the reactive effector moiety subtracted from the Tm of the first stem portion:second stem portion is from about 0° C. to about 20° C.; and/or the Tm of the duplex formed by the second nucleic acid molecule and the first or second stem portion linked to the reactive effector moiety is from about 30° C. to about 40° C.; and/or the Tm of the duplex formed by the nucleic acid molecule and the first or second stem portion linked to the reactive effector moiety subtracted from the Tm of the first stem portion:second stem portion is from about 5° C. to about 10° C.

5. The kit of claim 2 wherein the second nucleic acid molecule comprises from about 8 to about 15 nucleotide bases.

6. The kit of claim 2 wherein:
the first nucleic acid molecule comprises the nucleotide sequence of SEQ ID NO:13, and the second nucleic acid molecule comprises the nucleotide sequence 5'-AGCTCTCGAGT-3' (SEQ ID NO:15); or
the first nucleic acid molecule comprises the nucleotide sequence of SEQ ID NO:14, and the second nucleic acid molecule comprises the nucleotide sequence 5'-GACGTCTCGAGT-3' (SEQ ID NO:16).

7. The kit of claim 3 wherein the bio-orthogonal reactive molecule of the first nucleic acid molecule is hexynyl and the bio-orthogonal reactive molecule of the second nucleic acid molecule is azide.

8. A method of producing a templated assembly product for a cell comprising:
contacting a target nucleic acid molecule of the cell with a first nucleic acid molecule, wherein the first nucleic acid molecule comprises:
a) a first stem portion comprising from about 10 to about 20 nucleotide bases;
b) an anti-target loop portion comprising from about 16 to about 40 nucleotide bases and having a first end to which the first stem portion is linked, wherein the anti-target loop portion is substantially complementary to a target nucleic acid molecule;
c) a second stem portion comprising from about 10 to about 20 nucleotide bases linked to a second end of the anti-target loop portion, wherein the first stem portion is substantially complementary to the second stem portion; and
d) a reactive effector moiety linked to either the first stem portion or the second stem portion;

wherein the Tm of the anti-target loop portion:target nucleic acid molecule is greater than the Tm of the first stem portion:second stem portion; and
contacting the first nucleic acid molecule with a second nucleic acid molecule, wherein the second nucleic acid molecule comprises:
a nucleotide portion that is substantially complementary to the stem portion of the first nucleic acid molecule that is linked to the reactive effector moiety; and
a reactive effector moiety which can chemically interact with the reactive effector molecule of the first nucleic acid molecule;
wherein the Tm of the second nucleic acid molecule:first or second stem portion linked to the reactive effector moiety is less than or equal to the Tm of the first stem portion:second stem portion;
resulting in the combination of the respective reactive effector moieties thereby producing the templated assembly product.

9. The method of claim 8 wherein:
the first nucleic acid molecule comprises the nucleotide sequence of SEQ ID NO:13, and the second nucleic acid molecule comprises the nucleotide sequence 5'-AGCTCTCGAGT-3' (SEQ ID NO:15); or
the first nucleic acid molecule comprises the nucleotide sequence of SEQ ID NO:14, and the second nucleic acid molecule comprises the nucleotide sequence 5'-GACGTCTCGAGT-3' (SEQ ID NO:16).

10. The method of claim 8, wherein:
the reactive effector moiety of the second nucleic acid molecule is linked to a bio-orthogonal reactive molecule;
the reactive effector moiety of the first nucleic acid molecule is linked to a bio-orthogonal reactive molecule; and
the bio-orthogonal reactive molecule of the second nucleic acid molecule can chemically interact with the bio-orthogonal reactive molecule of the first nucleic acid molecule.

11. The method of claim 10 wherein the bio-orthogonal reactive molecule of the first nucleic acid molecule is hexynyl and the bio-orthogonal reactive molecule of the second nucleic acid molecule is azide.

* * * * *

SEQUENCE LISTING

```
<160> NUMBER OF SEQ ID NOS: 24

<210> SEQ ID NO 1
<211> LENGTH: 56
<212> TYPE: DNA
<213> ORGANISM: artificial sequence
<220> FEATURE:
<223> OTHER INFORMATION: HPV DNA target nucleic acid molecule

<400> SEQUENCE: 1
```

```
taactgtcaa aagccactgt gtcctgaaga aaagcaaaga catctggaca aaaagc        56

<210> SEQ ID NO 2
<211> LENGTH: 15
<212> TYPE: DNA
<213> ORGANISM: artificial sequence
<220> FEATURE:
<223> OTHER INFORMATION: haplomer

<400> SEQUENCE: 2
uccagauguc uuugc                                                    15

<210> SEQ ID NO 3
<211> LENGTH: 16
<212> TYPE: DNA
<213> ORGANISM: artificial sequence
<220> FEATURE:
<223> OTHER INFORMATION: haplomer

<400> SEQUENCE: 3
uuucuucagg acacag                                                   16

<210> SEQ ID NO 4
<211> LENGTH: 10
<212> TYPE: DNA
<213> ORGANISM: artificial sequence
<220> FEATURE:
<223> OTHER INFORMATION: click oligonucleotide

<400> SEQUENCE: 4
cttgtccagc                                                          10

<210> SEQ ID NO 5
<211> LENGTH: 10
<212> TYPE: DNA
<213> ORGANISM: artificial sequence
<220> FEATURE:
<223> OTHER INFORMATION: click oligonucleotide

<400> SEQUENCE: 5
tggaccatct                                                          10

<210> SEQ ID NO 6
<211> LENGTH: 30
<212> TYPE: DNA
<213> ORGANISM: artificial sequence
<220> FEATURE:
<223> OTHER INFORMATION: RNA oligonucleotide template

<400> SEQUENCE: 6
gaaauagaug guccagcugg acaagcagaa                                    30

<210> SEQ ID NO 7
<211> LENGTH: 58
<212> TYPE: DNA
<213> ORGANISM: artificial sequence
<220> FEATURE:
<223> OTHER INFORMATION: model oligonucleotide

<400> SEQUENCE: 7
actcgagacg tctctgtctt tgcttttctt caggacacag tggcgagacg tctcgagt    58

<210> SEQ ID NO 8
<211> LENGTH: 15
<212> TYPE: DNA
<213> ORGANISM: artificial sequence
```

```
<220> FEATURE:
<223> OTHER INFORMATION: model oligonucleotide

<400> SEQUENCE: 8
tttgacgtct cgagt                                                    15

<210> SEQ ID NO 9
<211> LENGTH: 1926
<212> TYPE: DNA
<213> ORGANISM: artificial sequence
<220> FEATURE:
<223> OTHER INFORMATION: EBNA1 coding sequence

<400> SEQUENCE: 9
atgtctgacg aggggccagg tacaggacct ggaaatggcc taggagagaa gggagacaca      60
tctggaccag aaggctccgg cggcagtgga cctcaaagaa gaggggtga taaccatgga     120 cgaggacggg gaagaggacg aggacgagga ggcggaagac caggagcccc gggcggctca     180
ggatcagggc caagacatag agatggtgtc cggagacccc aaaaacgtcc aagttgcatt     240
ggctgcaaag ggacccacgg tggaacagga gcaggagcag gagcgggagg ggcaggagca     300
ggaggggcag gagcaggagg aggggcagga gcaggaggag gggcaggagg ggcaggaggg     360
gcaggagggg caggagcagg aggaggggca ggagcaggag gaggggcagg aggggcagga     420
ggggcaggag caggaggagg ggcaggagca ggaggagggg caggagggc aggagcagga     480 ggaggggcag gaggggcagg aggggcagga gcaggaggag gggcaggagc aggaggaggg     540
gcaggagggg caggagcagg aggaggggca ggaggggcag gaggggcagg agcaggagga     600
ggggcaggag caggaggggc aggaggggca ggaggggcag gagcaggagg ggcaggagca     660
ggaggagggg caggaggggc aggaggggca ggagcaggag gggcaggagc aggagggca     720 ggagcaggag gggcaggagc aggaggggca ggaggggcag gagcaggagg ggcaggaggg     780
gcaggagcag gaggggcagg aggggcagga gcaggaggag gggcaggagg ggcaggagca     840
ggaggagggg caggaggggc aggagcagga ggggcaggag gggcaggagc aggaggggca     900
ggaggggcag gagcaggagg ggcaggaggg gcaggagcag gaggagggc aggagcagga     960 ggggcaggag caggaggtgg aggccggggt cgaggaggca gtggaggccg gggtcgagga    1020
ggtagtggag gccggggtcg aggaggtagt ggaggccgcc ggggtagagg acgtcaaaga    1080 gccaggggg gaagtcgtga aagagccagg gggagaggtc gtggacgtgg agaaaagagg    1140
cccaggagtc ccagtagtca gtcatcatca tccgggtctc caccgcgcag gccccctcca    1200
ggtagaaggc catttttcca ccctgtaggg gaagccgatt atttgaata ccaccaagaa    1260 ggtggcccag ctggtgagcc tgacgtgccc ccgggagcga tagagcaggg ccccgcagat    1320
gacccaggag aaggcccaag cactggaccc cggggtcagg gtgatggagg caggcgcaaa    1380
aaaggagggt ggtttggaaa gcatcgtggt caaggaggtt ccaacccgaa atttgagaac    1440
attgcagaag gttaagagc tctcctggct aggagtcacg tagaaaggac taccgacgaa    1500
ggaacttggg tcgccggtgt gttcgtatat ggaggtagta agacctccct ttacaaccta    1560
aggcgaggaa ctgcccttgc tattccacaa tgtcgtctta caccattgag tcgtctcccc    1620
tttggaatgg cccctggacc cggcccacaa cctggcccgc taagggagtc cattgtctgt    1680
tatttcatgg tctttttaca aactcatata tttgctgagg ttttgaagga tgcgattaag    1740
gaccttgtta tgacaaagcc cgctcctacc tgcaatatca gggtgactgt gtgcagcttt    1800
gacgatggag tagatttgcc tcctggtttt ccacctatgg tggaagggc tgccgcggag    1860
```

-continued

```
ggtgatgacg gagatgacgg agatgaagga ggtgatggag atgagggtga ggaagggcag    1920
gagtga                                                               1926

<210> SEQ ID NO 10
<211> LENGTH: 55
<212> TYPE: DNA
<213> ORGANISM: artificial sequence
<220> FEATURE:
<223> OTHER INFORMATION: representative oligonucleotide

<400> SEQUENCE: 10
ttcgactcga gacgtctcct tcctgcccct cctcctgctc cgagacgtct cgagt          55

<210> SEQ ID NO 11
<211> LENGTH: 16
<212> TYPE: DNA
<213> ORGANISM: artificial sequence
<220> FEATURE:
<223> OTHER INFORMATION: representative oligonucleotide

<400> SEQUENCE: 11
gacgtctcga gttctt                                                    16

<210> SEQ ID NO 12
<211> LENGTH: 35
<212> TYPE: DNA
<213> ORGANISM: artificial sequence
<220> FEATURE:
<223> OTHER INFORMATION: specific target

<400> SEQUENCE: 12
agttgcagga gcaggaggag gggcaggagc aggag                               35

<210> SEQ ID NO 13
<211> LENGTH: 60
<212> TYPE: DNA
<213> ORGANISM: artificial sequence
<220> FEATURE:
<223> OTHER INFORMATION: first nucleic acid molecule

<400> SEQUENCE: 13
actcgagacg tctccttgtc tttgcttttc ttcaggacac agtggcgaga cgtctcgagt    60

<210> SEQ ID NO 14
<211> LENGTH: 51
<212> TYPE: DNA
<213> ORGANISM: artificial sequence
<220> FEATURE:
<223> OTHER INFORMATION: first nucleic acid molecule

<400> SEQUENCE: 14
actcgagacg tctccttcct gcccctcctc ctgctccgag acgtctcgag t              51

<210> SEQ ID NO 15
<211> LENGTH: 11
<212> TYPE: DNA
<213> ORGANISM: artificial sequence
<220> FEATURE:
<223> OTHER INFORMATION: second nucleic acid molecule

<400> SEQUENCE: 15
agctctcgag t                                                         11

<210> SEQ ID NO 16
<211> LENGTH: 12
```

```
<212> TYPE: DNA
<213> ORGANISM: artificial sequence
<220> FEATURE:
<223> OTHER INFORMATION: second nucleic acid molecule

<400> SEQUENCE: 16
gacgtctcga gt                                                         12

<210> SEQ ID NO 17
<211> LENGTH: 60
<212> TYPE: DNA
<213> ORGANISM: artificial sequence
<220> FEATURE:
<223> OTHER INFORMATION: HPV first nucleic acid molecule with double
      scrambled stem sequences

<400> SEQUENCE: 17
gacagcacct tcgtcttgtc tttgcttttc ttcaggacac agtggcgggc tgcgacaatt      60

<210> SEQ ID NO 18
<211> LENGTH: 60
<212> TYPE: DNA
<213> ORGANISM: artificial sequence
<220> FEATURE:
<223> OTHER INFORMATION: HPV first nucleic acid molecule with single
      scrambled stem sequence

<400> SEQUENCE: 18
actcgagacg tctccttgtc tttgcttttc ttcaggacac agtggcgggc tgcgacaatt      60

<210> SEQ ID NO 19
<211> LENGTH: 34
<212> TYPE: DNA
<213> ORGANISM: artificial sequence
<220> FEATURE:
<223> OTHER INFORMATION: HPV RNA target nucleic acid molcule

<400> SEQUENCE: 19
aagccacugu guccugaaga aaagcaaaga cauc                                 34

<210> SEQ ID NO 20
<211> LENGTH: 60
<212> TYPE: DNA
<213> ORGANISM: artificial sequence
<220> FEATURE:
<223> OTHER INFORMATION: Unrelated 60-mer

<400> SEQUENCE: 20 cctttttta ggagaaggag acttagaggc catctccacc tccataaccc atttttttcc       60

<210> SEQ ID NO 21
<211> LENGTH: 60
<212> TYPE: DNA
<213> ORGANISM: artificial sequence
<220> FEATURE:
<223> OTHER INFORMATION: Unrelated 60-mer

<400> SEQUENCE: 21
ggaaaaaaat gggttatgga ggtggagatg gcctctaagt ctccttctcc taaaaaaagg      60

<210> SEQ ID NO 22
<211> LENGTH: 35
<212> TYPE: DNA
<213> ORGANISM: artificial sequence
<220> FEATURE:
<223> OTHER INFORMATION: Control non-specific oligonucleotide for EBNA1
```

```
<400> SEQUENCE: 22
gactagacgg ccagggagac gaatacatat tcaat                                35

<210> SEQ ID NO 23
<211> LENGTH: 56
<212> TYPE: DNA
<213> ORGANISM: artificial sequence
<220> FEATURE:
<223> OTHER INFORMATION: HPV DNA target nucleic acid molecule

<400> SEQUENCE: 23
uaacugucaa aagccacugu guccugaaga aaagcaaaga caucuggaca aaaagc         56

<210> SEQ ID NO 24
<211> LENGTH: 19
<212> TYPE: PRT
<213> ORGANISM: artificial sequence
<220> FEATURE:
<223> OTHER INFORMATION: small peptide agonist

<400> SEQUENCE: 24

Thr Arg Pro Leu Tyr Ser Thr Tyr Arg Met Glu Thr Val Ala Leu Asp
1               5                   10                  15

Met Glu Thr
```